US009534018B2

(12) United States Patent
Gruber

(10) Patent No.: US 9,534,018 B2
(45) Date of Patent: Jan. 3, 2017

(54) MELANOCORTIN ANALOGS HAVING ENHANCED ACTIVITY AND TRANSPORT

(71) Applicant: Tensive Controls Inc., Columbia, MO (US)

(72) Inventor: Kenneth Allen Gruber, Columbia, MO (US)

(73) Assignee: TENSIVE CONTROLS INC., Columbia, MO (US)

( * ) Notice: Subject to any disclaimer, the term of this patent is extended or adjusted under 35 U.S.C. 154(b) by 0 days.

(21) Appl. No.: 14/384,694

(22) PCT Filed: Mar. 12, 2013

(86) PCT No.: PCT/US2013/030528
§ 371 (c)(1),
(2) Date: Sep. 12, 2014

(87) PCT Pub. No.: WO2013/138340
PCT Pub. Date: Sep. 19, 2013

(65) Prior Publication Data
US 2015/0045293 A1 Feb. 12, 2015

Related U.S. Application Data

(60) Provisional application No. 61/610,149, filed on Mar. 13, 2012.

(51) Int. Cl.
*A61K 38/00* (2006.01)
*C07K 7/64* (2006.01)
*C07K 14/68* (2006.01)
*C07K 7/56* (2006.01)
*A61K 38/12* (2006.01)

(52) U.S. Cl.
CPC . *C07K 7/64* (2013.01); *C07K 7/56* (2013.01); *C07K 14/68* (2013.01); *A61K 38/00* (2013.01); *A61K 38/12* (2013.01)

(58) Field of Classification Search
None
See application file for complete search history.

(56) References Cited

U.S. PATENT DOCUMENTS

| | | | |
|---|---|---|---|
| 4,938,763 | A | 7/1990 | Dunn et al. |
| 5,693,608 | A | 12/1997 | Bechgaard et al. |
| 5,908,825 | A | 6/1999 | Fasano et al. |
| 5,977,070 | A | 11/1999 | Piazza et al. |
| 6,054,556 | A | 4/2000 | Hubby et al. |
| 6,432,438 | B1 | 8/2002 | Shukla |
| 6,673,767 | B1 | 1/2004 | Brodbeck et al. |
| 7,250,399 | B2 | 7/2007 | Bowers et al. |
| 7,342,089 | B2 | 3/2008 | Sharma et al. |
| 7,517,854 | B2 | 4/2009 | Conde-Frieboes et al. |
| 8,263,608 | B2 | 9/2012 | Shi et al. |
| 8,487,073 | B2 | 7/2013 | Shi et al. |
| 8,541,545 | B2 * | 9/2013 | Gruber ............... C07K 5/1024 530/300 |
| 2003/0032791 | A1 | 2/2003 | Alan et al. |
| 2011/0065652 | A1 | 3/2011 | Shi et al. |
| 2012/0220525 | A1 | 8/2012 | Gruber |
| 2012/0225828 | A1 | 9/2012 | Yang et al. |
| 2012/0225831 | A1 | 9/2012 | Yang et al. |

FOREIGN PATENT DOCUMENTS

| | | | |
|---|---|---|---|
| WO | WO2009061411 | A3 | 5/2009 |
| WO | WO2011026015 | A2 | 3/2011 |

OTHER PUBLICATIONS

Han et al, De Novo Design, Synthesis, and Pharmacology of r-Melanocyte Stimulating Hormone Analogues Derived from Somatostatin by a Hybrid Approach (J. Med. Chem. 2004, 47, 1514-1526).*
Grieco et al. "Extensive structure-activity studies of lactam derivatives of MT-II and SHU-9119: their activity and selectivity at human melanocortin receptors 3, 4, and 5," J Pept Res. 2003, 6295):199-206.
Grieco et al., "Preparation of 'side-chain-to-side-chain' cyclic peptides by Allyl and Alloc strategy: potential for library synthesis," J Rept Res. 2001, 57(3):250-256.
Qu et al., "Substitution of arginine with proline and praline derivatives in melanocyte-stimulating hormones leads to selectivity for human melanocortin 4 receptor," J Med Chem. 2009, 52(12):3627-3635.
Powers et al., "Irreversible Inhibitors of Serine, Cysteine, and Threonine Proteases," Chem. Rev. 2002, 102: 4639-4750.
Mayorov et al., "Cyclic lactam hybrid a-MSH/Agouti-related protein (AGRP) analogues with nanomolar range binding affinities at the human melanocortin receptors," Bioorg Med Chem Lett. 2011, 21(10):3099-102.
Mayorov et al., "Structure-activity relationships of cyclic lactam analogues of a-melanocyte—stimulating hormone (alpha-MSH) targeting the human melanocortin-3 receptor," J Med Chem. 2008, 51(2):187-95.
Mayorov, et al., "Development of Cyclic γ-MSH Analogues with Selective hMC3R Agonist and hMC3R/hMC5R Antagonist Activities," J Med Chem. 2006, 49(6):1946-1952.
Fung et al., "Design of cyclic and other templates for potent and selective peptide alpha-MSH analogues," Curr Opin Chem Biol. 2005, 9(4):352-358.
Han et al., "De novo design, synthesis, and pharmacology of alpha-melanocyte stimulating hormone analogues derived from somatostatin by a hybrid approach," J Med Chem. Mar. 11, 2004;47(6):1514-26.
Giuliani et al., "Selective melanocortin MC4 receptor agonists reverse haemorrhagic shock and prevent multiple organ damage," Br J Pharrnacol 2007; 150(5):595-603.
Bednarek et al., "Selective, High Affinity Peptide Antagonists of α-Melanotropin Action at Human Melanocortin Receptor 4: Their Synthesis and Biological Evaluation in Vitro†," J. Med. Chem., 2001, 44 (22), pp. 3665-3672.
Bednarek et al., "Potent and Selective Peptide Agonists of a-Melanotropin Action at Human Melanocortin Receptor 4: Their Synthesis and Biological Evaluation in Vitro," Biochem. Biophysical. Res, Comm. 286, 641-645 (2001).

(Continued)

*Primary Examiner* — Karlheinz R Skowronek
*Assistant Examiner* — Sergio Coffa
(74) *Attorney, Agent, or Firm* — Womble Carlyle Sandridge & Rice, LLP

(57) ABSTRACT

Described herein are melanocortin analogs having enhanced activity and transport.

13 Claims, 15 Drawing Sheets

(56) References Cited

OTHER PUBLICATIONS

Joppa et al., Central administration of peptide and small molecule MC4 receptor antagonists induce hyperphagia in mice and attenuate cytokine-induced anorexia, Peptides 26 (2005) 2294-2301.

Sutton et al., "A derivative of the melanocortin receptor antagonist SHU9119 (PG932) increases food intake when administered peripherally," Peptides 29 (2008) 104-111.

Muceniece et al., "Functional Evaluation of THIQ, a Melancortin 4 Receptor Agonist, in Models of Food Intake and Inflammation," Nordic Pharmacological Society, Basic & Clinical Pharmacology & Toxicology 101, 416-420 (2007).

* cited by examiner

A

B

A

B

SEQUENCE LISTING

<160> NUMBER OF SEQ ID NOS: 201

<210> SEQ ID NO 1
<211> LENGTH: 4
<212> TYPE: PRT
<213> ORGANISM: Artificial Sequence
<220> FEATURE:
<223> OTHER INFORMATION: Synthetic Melanocortin Pharmacophore

<400> SEQUENCE: 1

His Phe Arg Trp
1

<210> SEQ ID NO 2
<211> LENGTH: 6
<212> TYPE: PRT
<213> ORGANISM: Artificial Sequence
<220> FEATURE:
<223> OTHER INFORMATION: Synthetic polypeptide:

```
      Ac-Nle-Asp-His-Phe-Arg-Trp
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle

<400> SEQUENCE: 2

Leu Asp His Pro Arg Trp
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic polypeptide:
      Ac-Nle-Asp-His-D-Phe-Arg-Trp
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe

<400> SEQUENCE: 3

Leu Asp His Pro Arg Trp
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic polypeptide:
      Ac-Nle-c[Asp-His-Phe-Arg-Trp-Lys]
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon;

<400> SEQUENCE: 4

Leu Asp His Phe Arg Trp Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon;
<220> FEATURE:
<221> NAME/KEY: MOD_RES
<222> LOCATION: (4)..(4)
<223> OTHER INFORMATION: D-Phe4

<400> SEQUENCE: 5

Leu Asp His Phe Arg Trp Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa 4 = D-Nal(2'); D-(naphth-2-yl)alanine

<400> SEQUENCE: 6

Leu Asp His Xaa Arg Trp Lys
1               5

<210> SEQ ID NO 7
<211> LENGTH: 12
<212> TYPE: PRT
<213> ORGANISM: Artificial Sequence
<220> FEATURE:
<223> OTHER INFORMATION: Synthetic polypeptide:
      Ac-c[Cys-Glu-His-D-Nal(2')-Arg-Trp-Gly-Cys]-Pro-Pro-Lys-Asp
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(8)
<223> OTHER INFORMATION: disulfide bond between Cys1 and Cys8
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine

<400> SEQUENCE: 7

Cys Glu His Xaa Arg Trp Gly Cys Pro Pro Lys Asp
1               5                   10

<210> SEQ ID NO 8
```

```
<211> LENGTH: 7
<212> TYPE: PRT
<213> ORGANISM: Artificial Sequence
<220> FEATURE:
<223> OTHER INFORMATION: Synthetic polypeptide:
      Ac-Nle-Glu-His-D-Phe-Arg-D-Trp-Gly
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe4
<220> FEATURE:
<221> NAME/KEY: MOD_RES
<222> LOCATION: (6)..(6)
<223> OTHER INFORMATION: D-Trp6

<400> SEQUENCE: 8

Leu Glu His Phe Arg Trp Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic polypeptide:
      His-Phe-Arg-Trp-Gly-Lys-Pro-Val

<400> SEQUENCE: 9

His Phe Arg Trp Gly Lys Pro Val
1               5

<210> SEQ ID NO 10
<211> LENGTH: 12
<212> TYPE: PRT
<213> ORGANISM: Artificial Sequence
<220> FEATURE:
<223> OTHER INFORMATION: Synthetic polypeptide:
      Ac-Ser-Tyr-Nle-Glu-His-D-Phe-Arg-Trp-Gly-Lys-Pro-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: D-Phe6
<220> FEATURE:
<221> NAME/KEY: MOD_RES
<222> LOCATION: (7)..(7)
<223> OTHER INFORMATION: AMIDATION

<400> SEQUENCE: 10

Ser Thr Leu Glu His Phe Arg Trp Gly Lys Pro Val
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic polypeptide:
```

```
        Ac-Nle-c[Asp-His-D-Phe-Arg-Trp-Lys]-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
        10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: AMIDATION

<400> SEQUENCE: 11

Leu Asp His Phe Arg Trp Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic polypeptide:
        Ac-Nle-c[Asp-His-D-Phe-Arg-Trp-Lys]
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
        10-epsilon
<220> FEATURE:
<221> NAME/KEY: MOD_RES
<222> LOCATION: (4)..(4)
<223> OTHER INFORMATION: D-Phe4

<400> SEQUENCE: 12

Leu Asp His Phe Arg Trp Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic polypeptide:
        Ac-Nle-c[Asp-His-D-Nal(2')-Arg-Trp-Lys]-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
```

```
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: AMIDATION

<400> SEQUENCE: 13

Leu Asp His Xaa Arg Trp Lys
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-Pro-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (9)..(9)
<223> OTHER INFORMATION: AMIDATION

<400> SEQUENCE: 14

Leu Asp Pro Xaa Arg Trp Lys Pro Val
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-D-Thr-D-Pro-D-Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Thr8
```

```
<220> FEATURE:
<221> NAME/KEY: MOD_RES
<222> LOCATION: (9)..(9)
<223> OTHER INFORMATION: D-Pro9
<220> FEATURE:
<221> NAME/KEY: MOD_RES
<222> LOCATION: (10)..(10)
<223> OTHER INFORMATION: D-Thr10

<400> SEQUENCE: 15

Leu Asp Pro Xaa Arg Trp Lys Thr Pro Thr
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-D-Pro-D-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Thr9

<400> SEQUENCE: 16

Leu Asp Pro Xaa Arg Trp Lys Pro Val
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-D-Pro-D-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
```

```
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Thr9

<400> SEQUENCE: 17

Leu Asp His Xaa Arg Trp Lys Pro Val
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-D-Pro-D-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Val9

<400> SEQUENCE: 18

Leu Asp Pro Xaa Arg Trp Lys Pro Val
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta3-Pro-beta2-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
```

```
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta3-Pro8
<220> FEATURE:
<221> NAME/KEY: MOD_RES
<222> LOCATION: (8)..(8)
<223> OTHER INFORMATION: AMIDATION; beta2-Val9

<400> SEQUENCE: 19

Leu Asp Pro Xaa Arg Trp Lys Pro Val
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta3-Pro-beta3-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta3-Pro8
<220> FEATURE:
<221> NAME/KEY: MOD_RES
<222> LOCATION: (9)..(9)
<223> OTHER INFORMATION: AMIDATION; beta3-Val9

<400> SEQUENCE: 20

Leu Asp Pro Xaa Arg Trp Lys Pro Val
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-D-Val-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
```

```
            10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Val8
<220> FEATURE:
<221> NAME/KEY: MOD_RES
<222> LOCATION: (9)..(9)
<223> OTHER INFORMATION: AMIDATION; D-Pro9

<400> SEQUENCE: 21

Leu Asp Pro Xaa Arg Trp Lys Val Pro
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-D-Thr-D-Pro-D-Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Thr8
<220> FEATURE:
<221> NAME/KEY: MOD_RES
<222> LOCATION: (9)..(9)
<223> OTHER INFORMATION: D-Pro9
<220> FEATURE:
<221> NAME/KEY: MOD_RES
<222> LOCATION: (10)..(10)
<223> OTHER INFORMATION: D-Thr10

<400> SEQUENCE: 22

Leu Asp Pro Xaa Arg Trp Lys Thr Pro Thr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-D-Thr-D-Pro-D-Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
```

```
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Thr8
<220> FEATURE:
<221> NAME/KEY: MOD_RES
<222> LOCATION: (9)..(9)
<223> OTHER INFORMATION: D-Pro9
<220> FEATURE:
<221> NAME/KEY: MOD_RES
<222> LOCATION: (10)..(10)
<223> OTHER INFORMATION: D-Thr10

<400> SEQUENCE: 23

Leu Asp His Xaa Arg Trp Lys Thr Pro Thr
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-D-Thr-D-Pro-D-Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Thr8
<220> FEATURE:
<221> NAME/KEY: MOD_RES
<222> LOCATION: (9)..(9)
<223> OTHER INFORMATION: D-Pro9
<220> FEATURE:
<221> NAME/KEY: MOD_RES
<222> LOCATION: (10)..(10)
<223> OTHER INFORMATION: D-Thr10

<400> SEQUENCE: 24

Leu Asp Pro Xaa Arg Trp Lys Thr Pro Thr
1               5                   10

<210> SEQ ID NO 25
```

```
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-D-Thr-D-Pro-D-Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Thr8
<220> FEATURE:
<221> NAME/KEY: MOD_RES
<222> LOCATION: (9)..(9)
<223> OTHER INFORMATION: D-Pro9
<220> FEATURE:
<221> NAME/KEY: MOD_RES
<222> LOCATION: (10)..(10)
<223> OTHER INFORMATION: D-Thr10

<400> SEQUENCE: 25

Leu Asp His Xaa Arg Trp Lys Thr Pro Thr
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-D-Pro-D-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Pro8
<220> FEATURE:
```

```
<221> NAME/KEY: MOD_RES
<222> LOCATION: (9)..(9)
<223> OTHER INFORMATION: AMIDATION; D-Val9

<400> SEQUENCE: 26

Leu Asp Pro Xaa Arg Trp Lys Pro Val
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-D-Pro-D-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Val9

<400> SEQUENCE: 27

Leu Asp His Xaa Arg Trp Lys Pro Val
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-D-Pro-D-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
```

```
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Val9

<400> SEQUENCE: 28

Leu Asp Pro Xaa Arg Trp Lys Pro Val
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-D-Pro-D-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Val9

<400> SEQUENCE: 29

Leu Asp His Xaa Arg Trp Lys Pro Val
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-D-Val-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
```

-continued

```
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Val8
<220> FEATURE:
<221> NAME/KEY: MOD_RES
<222> LOCATION: (9)..(9)
<223> OTHER INFORMATION: AMIDATION; D-Pro9

<400> SEQUENCE: 30

Leu Asp Pro Xaa Arg Trp Lys Val Pro
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-D-Val-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Val8
<220> FEATURE:
<221> NAME/KEY: MOD_RES
<222> LOCATION: (9)..(9)
<223> OTHER INFORMATION: AMIDATION; D-Pro9

<400> SEQUENCE: 31

Leu Asp His Xaa Arg Trp Lys Val Pro
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-D-Val-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
```

```
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Val8
<220> FEATURE:
<221> NAME/KEY: MOD_RES
<222> LOCATION: (9)..(9)
<223> OTHER INFORMATION: AMIDATION; D-Pro9

<400> SEQUENCE: 32

Leu Asp Pro Xaa Arg Trp Lys Val Pro
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-D-Val-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Val8
<220> FEATURE:
<221> NAME/KEY: MOD_RES
<222> LOCATION: (9)..(9)
<223> OTHER INFORMATION: AMIDATION; D-Pro9

<400> SEQUENCE: 33

Leu Asp His Xaa Arg Trp Lys Val Pro
1               5

<210> SEQ ID NO 34
```

```
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta-Pro-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Val9

<400> SEQUENCE: 34

Leu Asp Pro Xaa Arg Trp Lys Pro Val
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-beta-Pro-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Val9

<400> SEQUENCE: 35

Leu Asp His Xaa Arg Trp Lys Pro Val
1               5

<210> SEQ ID NO 36
<211> LENGTH: 9
```

```
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-beta-Pro-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Val9

<400> SEQUENCE: 36

Leu Asp Pro Xaa Arg Trp Lys Pro Val
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-beta-Pro-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
```

```
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Val9

<400> SEQUENCE: 37

Leu Asp His Xaa Arg Trp Lys Pro Val
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta-Val-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 38

Leu Asp Pro Xaa Arg Trp Lys Val Pro
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-beta-Val-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
```

```
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 39

Leu Asp His Xaa Arg Trp Lys Val Pro
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-beta-Val-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 40

Leu Asp Pro Xaa Arg Trp Lys Val Pro
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-beta-Val-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
```

```
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 41

Leu Asp His Xaa Arg Trp Lys Val Pro
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta-Pro-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Pro9

<400> SEQUENCE: 42

Leu Asp Pro Xaa Arg Trp Lys Pro Pro
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-beta-Pro-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
```

```
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Pro9

<400> SEQUENCE: 43

Leu Asp His Xaa Arg Trp Lys Pro Pro
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-beta-Pro-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Pro9

<400> SEQUENCE: 44

Leu Asp Pro Xaa Arg Trp Lys Pro Pro
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic polypeptide:
```

```
      Ac-Nle-c[D-Asp-His-D-Nal(2')-Arg-Trp-D-Lys]-beta-Pro-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Pro9

<400> SEQUENCE: 45

Leu Asp His Xaa Arg Trp Lys Pro Pro
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta-Val-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 46

Leu Asp Pro Xaa Arg Trp Lys Val Val
1               5
```

```
<210> SEQ ID NO 47
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-beta-Val-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 47

Leu Asp His Xaa Arg Trp Lys Val Val
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-beta-Val-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
```

<223> OTHER INFORMATION: AMIDATION; beta-Val9

<400> SEQUENCE: 48

Leu Asp Pro Xaa Arg Trp Lys Val Val
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-beta-Val-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 49

Leu Asp His Xaa Arg Trp Lys Val Val
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-(3-methyl)-beta-Val-beta-
      Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)

```
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 50

Leu Asp Pro Xaa Arg Trp Lys Val Val
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-(3-methyl)-beta-Val-beta-
      Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 51

Leu Asp His Xaa Arg Trp Lys Val Val
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-(3-methyl)-beta-Val-
      beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
```

```
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 52

Leu Asp Pro Xaa Arg Trp Lys Val Val
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-(3-methyl)-beta-Val-
      beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 53

Leu Asp His Xaa Arg Trp Lys Val Val
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic polypeptide:
```

```
      Ac-Nle-c[Asp-Pro-D-Nal(2')-Arg-Trp-Lys]-(3-methyl)-beta-Val-beta-
      Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 54

Leu Asp Pro Xaa Arg Trp Lys Val Pro
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-(3-methyl)-beta-Val-beta-
      Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 55

Leu Asp His Xaa Arg Trp Lys Val Pro
1               5

<210> SEQ ID NO 56
<211> LENGTH: 9
<212> TYPE: PRT
<213> ORGANISM: Artificial Sequence
<220> FEATURE:
```

```
<223> OTHER INFORMATION: Synthetic polypeptide:
      Ac-Nle-c[D-Asp-Pro-D-Nal(2')-Arg-Trp-D-Lys]-(3-methyl)-beta-Val-
      beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 56

Leu Asp Pro Xaa Arg Trp Lys Val Pro
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-(3-methyl)-beta-Val-
      beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
```

```
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 57

Leu Asp His Xaa Arg Trp Lys Val Pro
1               5

<210> SEQ ID NO 58
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta-Thr-beta-Pro-beta-Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Thr8
<220> FEATURE:
<221> NAME/KEY: MOD_RES
<222> LOCATION: (9)..(9)
<223> OTHER INFORMATION: beta-Pro9
<220> FEATURE:
<221> NAME/KEY: MOD_RES
<222> LOCATION: (10)..(10)
<223> OTHER INFORMATION: beta-Thr10

<400> SEQUENCE: 58

Leu Asp Pro Xaa Arg Trp Lys Thr Pro Thr
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-beta-Thr-beta-Pro-beta-Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
```

-continued

```
<220> FEATURE:
<221> NAME/KEY: MOD_RES
<222> LOCATION: (8)..(8)
<223> OTHER INFORMATION: beta-Thr8
<220> FEATURE:
<221> NAME/KEY: MOD_RES
<222> LOCATION: (9)..(9)
<223> OTHER INFORMATION: beta-Pro9
<220> FEATURE:
<221> NAME/KEY: MOD_RES
<222> LOCATION: (10)..(10)
<223> OTHER INFORMATION: beta-Thr10

<400> SEQUENCE: 59

Leu Asp His Xaa Arg Trp Lys Thr Pro Thr
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-beta-Thr-beta-Pro-
      beta-Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Thr8
<220> FEATURE:
<221> NAME/KEY: MOD_RES
<222> LOCATION: (9)..(9)
<223> OTHER INFORMATION: beta-Pro9
<220> FEATURE:
<221> NAME/KEY: MOD_RES
<222> LOCATION: (10)..(10)
<223> OTHER INFORMATION: beta-Thr10

<400> SEQUENCE: 60

Leu Asp Pro Xaa Arg Trp Lys Thr Pro Thr
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-beta-Thr-beta-Pro-
      beta-Thr
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Thr8
<220> FEATURE:
<221> NAME/KEY: MOD_RES
<222> LOCATION: (9)..(9)
<223> OTHER INFORMATION: beta-Pro9
<220> FEATURE:
<221> NAME/KEY: MOD_RES
<222> LOCATION: (10)..(10)
<223> OTHER INFORMATION: beta-Thr10

<400> SEQUENCE: 61

Leu Asp His Xaa Arg Trp Lys Thr Pro Thr
1               5                   10

<210> SEQ ID NO 62
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-D-Pro-D-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Ala9

<400> SEQUENCE: 62
```

-continued

```
Leu Asp Pro Xaa Arg Trp Lys Pro Ala
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-D-Pro-D-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Ala9

<400> SEQUENCE: 63

Leu Asp His Xaa Arg Trp Lys Pro Ala
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-D-Pro-D-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Pro8
```

```
<220> FEATURE:
<221> NAME/KEY: MOD_RES
<222> LOCATION: (9)..(9)
<223> OTHER INFORMATION: AMIDATION; D-Ala9

<400> SEQUENCE: 64

Leu Asp Pro Xaa Arg Trp Lys Pro Ala
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-D-Pro-D-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Ala9

<400> SEQUENCE: 65

Leu Asp His Xaa Arg Trp Lys Pro Ala
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-D-Ala-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
```

```
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Ala8
<220> FEATURE:
<221> NAME/KEY: MOD_RES
<222> LOCATION: (9)..(9)
<223> OTHER INFORMATION: AMIDATION; D-Pro9

<400> SEQUENCE: 66

Leu Asp Pro Xaa Arg Trp Lys Ala Pro
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-D-Ala-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Ala8
<220> FEATURE:
<221> NAME/KEY: MOD_RES
<222> LOCATION: (9)..(9)
<223> OTHER INFORMATION: AMIDATION; D-Pro9

<400> SEQUENCE: 67

Leu Asp His Xaa Arg Trp Lys Ala Pro
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-D-Ala-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
```

```
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Ala8
<220> FEATURE:
<221> NAME/KEY: MOD_RES
<222> LOCATION: (9)..(9)
<223> OTHER INFORMATION: AMIDATION; D-Pro9

<400> SEQUENCE: 68

Leu Asp Pro Xaa Arg Trp Lys Ala Pro
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-D-Ala-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Ala8
<220> FEATURE:
<221> NAME/KEY: MOD_RES
<222> LOCATION: (9)..(9)
<223> OTHER INFORMATION: AMIDATION; D-Pro9

<400> SEQUENCE: 69

Leu Asp His Xaa Arg Trp Lys Ala Pro
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta-Pro-beta-Ala-NH2
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Ala9

<400> SEQUENCE: 70

Leu Asp Pro Xaa Arg Trp Lys Pro Ala
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-beta-Pro-beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Ala9

<400> SEQUENCE: 71

Leu Asp His Xaa Arg Trp Lys Pro Ala
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-beta-Pro-beta-Ala-NH2
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Ala9

<400> SEQUENCE: 72

Leu Asp Pro Xaa Arg Trp Lys Pro Ala
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-beta-Pro-beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Ala9
```

```
<400> SEQUENCE: 73

Leu Asp His Xaa Arg Trp Lys Pro Ala
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta-Ala-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Ala8
<220> FEATURE:
<221> NAME/KEY: MOD_RES
<222> LOCATION: (9)..(9)
<223> OTHER INFORMATION: AMIDATION; beta-Pro9

<400> SEQUENCE: 74

Leu Asp Pro Xaa Arg Trp Lys Ala Pro
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-beta-Ala-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Ala8
<220> FEATURE:
<221> NAME/KEY: MOD_RES
<222> LOCATION: (9)..(9)
<223> OTHER INFORMATION: AMIDATION; beta-Pro9
```

```
<400> SEQUENCE: 75

Leu Asp His Xaa Arg Trp Lys Ala Pro
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-beta-Ala-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Ala8
<220> FEATURE:
<221> NAME/KEY: MOD_RES
<222> LOCATION: (9)..(9)
<223> OTHER INFORMATION: AMIDATION; beta-Pro9

<400> SEQUENCE: 76

Leu Asp Pro Xaa Arg Trp Lys Ala Pro
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-beta-Ala-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
```

```
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Ala8
<220> FEATURE:
<221> NAME/KEY: MOD_RES
<222> LOCATION: (9)..(9)
<223> OTHER INFORMATION: AMIDATION; beta-Pro9

<400> SEQUENCE: 77

Leu Asp His Xaa Arg Trp Lys Ala Pro
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta-Val-beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 78

Leu Asp Pro Xaa Arg Trp Lys Val Ala
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-beta-Val-beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
```

```
                10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 79

Leu Asp His Xaa Arg Trp Lys Val Ala
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-beta-Val-beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 80

Leu Asp Pro Xaa Arg Trp Lys Val Ala
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-beta-Val-beta-Ala-NH2
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 81

Leu Asp His Xaa Arg Trp Lys Val Ala
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-(3-methyl)-beta-Val-beta-
      Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 82

Leu Asp Pro Xaa Arg Trp Lys Val Ala
1               5

<210> SEQ ID NO 83
<211> LENGTH: 9
<212> TYPE: PRT
<213> ORGANISM: Artificial Sequence
```

```
<220> FEATURE:
<223> OTHER INFORMATION: Synthetic polypeptide:
      Ac-Nle-c[Asp-His-D-Nal(2')-Arg-Trp-Lys]-(3-methyl)-beta-Val-beta-
      Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 83

Leu Asp His Xaa Arg Trp Lys Val Ala
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-(3-methyl)-beta-Val-
      beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 84
```

```
Leu Asp Pro Xaa Arg Trp Lys Val Ala
1               5
```

<210> SEQ ID NO 85
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-(3-methyl)-beta-Val-
      beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 85

```
Leu Asp His Xaa Arg Trp Lys Val Ala
1               5
```

<210> SEQ ID NO 86
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-D-Pro-D-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Leu9

<400> SEQUENCE: 86

Leu Asp Pro Xaa Arg Trp Lys Pro Leu
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-D-Pro-D-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Leu9

<400> SEQUENCE: 87

Leu Asp His Xaa Arg Trp Lys Pro Leu
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-D-Pro-D-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)

-continued

```
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Leu9

<400> SEQUENCE: 88

Leu Asp Pro Xaa Arg Trp Lys Pro Leu
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-D-Pro-D-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Leu9

<400> SEQUENCE: 89

Leu Asp His Xaa Arg Trp Lys Pro Leu
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-D-Leu-D-Pro-NH2
<220> FEATURE:
<221> NAME/KEY: MOD_RES
<222> LOCATION: (1)..(1)
<223> OTHER INFORMATION: ACETYLATION
<220> FEATURE:
```

<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Leu8
<220> FEATURE:
<221> NAME/KEY: MOD_RES
<222> LOCATION: (9)..(9)
<223> OTHER INFORMATION: AMIDATION; D-Pro9

<400> SEQUENCE: 90

Leu Asp Pro Xaa Arg Trp Lys Leu Pro
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-D-Leu-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Leu8
<220> FEATURE:
<221> NAME/KEY: MOD_RES
<222> LOCATION: (9)..(9)
<223> OTHER INFORMATION: AMIDATION; D-Pro9

<400> SEQUENCE: 91

Leu Asp His Xaa Arg Trp Lys Leu Pro
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-D-Leu-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES

```
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Leu8
<220> FEATURE:
<221> NAME/KEY: MOD_RES
<222> LOCATION: (9)..(9)
<223> OTHER INFORMATION: AMIDATION; D-Pro9

<400> SEQUENCE: 92

Leu Asp Pro Xaa Arg Trp Lys Leu Pro
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-D-Leu-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Leu8
<220> FEATURE:
<221> NAME/KEY: MOD_RES
<222> LOCATION: (9)..(9)
<223> OTHER INFORMATION: AMIDATION; D-Pro9

<400> SEQUENCE: 93

Leu Asp His Xaa Arg Trp Lys Leu Pro
1               5
```

```
<210> SEQ ID NO 94
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta-Pro-beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Leu9

<400> SEQUENCE: 94

Leu Asp Pro Xaa Arg Trp Lys Pro Leu
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-beta-Pro-beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Leu9

<400> SEQUENCE: 95

Leu Asp His Xaa Arg Trp Lys Pro Leu
1               5
```

<210> SEQ ID NO 96
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-beta-Pro-beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Leu9

<400> SEQUENCE: 96

Leu Asp Pro Xaa Arg Trp Lys Pro Leu
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-beta-Pro-beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)

```
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Leu9

<400> SEQUENCE: 97

Leu Asp His Xaa Arg Trp Lys Pro Leu
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta-Leu-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Leu8
<220> FEATURE:
<221> NAME/KEY: MOD_RES
<222> LOCATION: (9)..(9)
<223> OTHER INFORMATION: AMIDATION; beta-Pro9

<400> SEQUENCE: 98

Leu Asp Pro Xaa Arg Trp Lys Leu Pro
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-beta-Leu-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
```

```
<220> FEATURE:
<221> NAME/KEY: MOD_RES
<222> LOCATION: (8)..(8)
<223> OTHER INFORMATION: beta-Leu8
<220> FEATURE:
<221> NAME/KEY: MOD_RES
<222> LOCATION: (9)..(9)
<223> OTHER INFORMATION: AMIDATION; beta-Pro9

<400> SEQUENCE: 99

Leu Asp His Xaa Arg Trp Lys Leu Pro
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-beta-Leu-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Leu8
<220> FEATURE:
<221> NAME/KEY: MOD_RES
<222> LOCATION: (9)..(9)
<223> OTHER INFORMATION: AMIDATION; beta-Pro9

<400> SEQUENCE: 100

Leu Asp Pro Xaa Arg Trp Lys Leu Pro
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-beta-Leu-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
```

```
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Leu8
<220> FEATURE:
<221> NAME/KEY: MOD_RES
<222> LOCATION: (9)..(9)
<223> OTHER INFORMATION: AMIDATION; beta-Pro9

<400> SEQUENCE: 101

Leu Asp His Xaa Arg Trp Lys Leu Pro
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta-Val-beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 102

Leu Asp Pro Xaa Arg Trp Lys Val Leu
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-beta-Val-beta-Leu-NH2
<220> FEATURE:
<221> NAME/KEY: MOD_RES
<222> LOCATION: (1)..(1)
```

<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
    10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 103

Leu Asp His Xaa Arg Trp Lys Val Leu
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic polypeptide:
    Ac-Nle-c[D-Asp-Pro-D-Nal(2')-Arg-Trp-D-Lys]-beta-Val-beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
    10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 104

Leu Asp Pro Xaa Arg Trp Lys Val Leu
1               5

<210> SEQ ID NO 105
<211> LENGTH: 9
<212> TYPE: PRT

```
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-beta-Val-beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 105

Leu Asp His Xaa Arg Trp Lys Val Leu
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-(3-methyl)-beta-Val-beta-
      Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 106
```

```
Leu Asp Pro Xaa Arg Trp Lys Val Leu
1               5
```

<210> SEQ ID NO 107
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Nal(2')-Arg-Trp-Lys]-(3-methyl)-beta-Val-beta-
      Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 107

```
Leu Asp His Xaa Arg Trp Lys Val Leu
1               5
```

<210> SEQ ID NO 108
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-(3-methyl)-beta-Val-
      beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:

```
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 108

Leu Asp Pro Xaa Arg Trp Lys Val Leu
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-(3-methyl)-beta-Val-
      beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 109

Leu Asp His Xaa Arg Trp Lys Val Leu
1               5

<210> SEQ ID NO 110
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-D-Thr-D-Pro-D-Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
```

```
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Thr8
<220> FEATURE:
<221> NAME/KEY: MOD_RES
<222> LOCATION: (9)..(9)
<223> OTHER INFORMATION: D-Pro9
<220> FEATURE:
<221> NAME/KEY: MOD_RES
<222> LOCATION: (10)..(10)
<223> OTHER INFORMATION: D-Thr10

<400> SEQUENCE: 110

Leu Asp Pro Phe Arg Trp Lys Thr Pro Thr
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-D-Thr-D-Pro-D-Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Thr8
<220> FEATURE:
<221> NAME/KEY: MOD_RES
<222> LOCATION: (9)..(9)
<223> OTHER INFORMATION: D-Pro9
<220> FEATURE:
<221> NAME/KEY: MOD_RES
<222> LOCATION: (10)..(10)
<223> OTHER INFORMATION: D-Thr10

<400> SEQUENCE: 111

Leu Asp His Phe Arg Trp Lys Thr Pro Thr
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-D-Thr-D-Pro-D-Thr
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Thr8
<220> FEATURE:
<221> NAME/KEY: MOD_RES
<222> LOCATION: (9)..(9)
<223> OTHER INFORMATION: D-Pro9
<220> FEATURE:
<221> NAME/KEY: MOD_RES
<222> LOCATION: (10)..(10)
<223> OTHER INFORMATION: D-Thr10

<400> SEQUENCE: 112

Leu Asp Pro Phe Arg Trp Lys Thr Pro Thr
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-D-Thr-D-Pro-D-Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Thr8
<220> FEATURE:
<221> NAME/KEY: MOD_RES
```

```
<222> LOCATION: (9)..(9)
<223> OTHER INFORMATION: D-Pro9
<220> FEATURE:
<221> NAME/KEY: MOD_RES
<222> LOCATION: (10)..(10)
<223> OTHER INFORMATION: D-Thr10

<400> SEQUENCE: 113

Leu Asp His Phe Arg Trp Lys Thr Pro Thr
1               5                   10

<210> SEQ ID NO 114
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-D-Pro-D-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Val9

<400> SEQUENCE: 114

Leu Asp Pro Phe Arg Trp Lys Pro Val
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-D-Pro-D-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
```

<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Val9

<400> SEQUENCE: 115

Leu Asp His Phe Arg Trp Lys Pro Val
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-D-Pro-D-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Val9

<400> SEQUENCE: 116

Leu Asp Pro Xaa Arg Trp Lys Pro Val
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-D-Pro-D-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:

```
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Val9

<400> SEQUENCE: 117

Leu Asp His Xaa Arg Trp Lys Pro Val
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-D-Val-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Val8
<220> FEATURE:
<221> NAME/KEY: MOD_RES
<222> LOCATION: (9)..(9)
<223> OTHER INFORMATION: AMIDATION; D-Pro9

<400> SEQUENCE: 118

Leu Asp Pro Phe Arg Trp Lys Val Pro
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-D-Val-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
```

-continued

```
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Val8
<220> FEATURE:
<221> NAME/KEY: MOD_RES
<222> LOCATION: (9)..(9)
<223> OTHER INFORMATION: AMIDATION; D-Pro9

<400> SEQUENCE: 119

Leu Asp His Phe Arg Trp Lys Pro Val
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-D-Val-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Val8
<220> FEATURE:
<221> NAME/KEY: MOD_RES
<222> LOCATION: (9)..(9)
<223> OTHER INFORMATION: AMIDATION; D-Pro9

<400> SEQUENCE: 120

Leu Asp Pro Phe Arg Trp Lys Val Pro
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic polypeptide:
```

```
         Ac-Nle-c[D-Asp-His-D-Nal(2')-Arg-Trp-D-Lys]-D-Val-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Val8
<220> FEATURE:
<221> NAME/KEY: MOD_RES
<222> LOCATION: (9)..(9)
<223> OTHER INFORMATION: AMIDATION; D-Pro9

<400> SEQUENCE: 121

Leu Asp His Xaa Arg Trp Lys Val Pro
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-beta-Pro-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Val9

<400> SEQUENCE: 122

Leu Asp Pro Phe Arg Trp Lys Pro Val
1               5
```

```
<210> SEQ ID NO 123
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-beta-Pro-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Val9

<400> SEQUENCE: 123

Leu Asp His Phe Arg Trp Lys Pro Val
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-beta-Pro-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
```

```
<223> OTHER INFORMATION: AMIDATION; beta-Val9

<400> SEQUENCE: 124

Leu Asp Pro Phe Arg Trp Lys Pro Val
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-beta-Pro-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Val9

<400> SEQUENCE: 125

Leu Asp His Phe Arg Trp Lys Pro Val
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-beta-Val-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
```

```
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 126

Leu Asp Pro Phe Arg Trp Lys Val Pro
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-beta-Val-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 127

Leu Asp His Phe Arg Trp Lys Pro Val
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-beta-Val-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
```

<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 128

Leu Asp Pro Phe Arg Trp Lys Val Pro
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-beta-Val-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 129

Leu Asp His Xaa Arg Trp Lys Val Pro
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-beta-Pro-beta-Pro-NH2
<220> FEATURE:
<221> NAME/KEY: MOD_RES
<222> LOCATION: (1)..(1)

```
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Pro9

<400> SEQUENCE: 130

Leu Asp Pro Phe Arg Trp Lys Pro Pro
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-beta-Pro-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Pro9

<400> SEQUENCE: 131

Leu Asp His Phe Arg Trp Lys Pro Pro
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Nal(2')-Arg-Trp-D-Lys]-beta-Pro-beta-Pro-NH2
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Pro9

<400> SEQUENCE: 132

Leu Asp Pro Xaa Arg Trp Lys Pro Pro
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-beta-Pro-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Pro9

<400> SEQUENCE: 133
```

```
Leu Asp His Xaa Arg Trp Lys Pro Pro
1               5
```

<210> SEQ ID NO 134
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-beta-Val-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 134

```
Leu Asp Pro Phe Arg Trp Lys Val Val
1               5
```

<210> SEQ ID NO 135
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-beta-Val-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 135

Leu Asp His Phe Arg Trp Lys Val Val

```
<210> SEQ ID NO 136
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-beta-Val-beta-Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 136

Leu Asp Pro Phe Arg Trp Lys Val Val
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-beta-Val-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
```

```
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 137

Leu Asp His Phe Arg Trp Lys Val Val
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-(3-methyl)-beta-Val-beta-Val-
      NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 138

Leu Asp Pro Phe Arg Trp Lys Val Val
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-(3-methyl)-beta-Val-beta-Val-
      NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
```

```
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 139

Leu Asp His Phe Arg Trp Lys Val Val
1               5

<210> SEQ ID NO 140
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-(3-methyl)-beta-Val-beta-
      Val-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 140

Leu Asp Pro Phe Arg Trp Lys Val Val
1               5

<210> SEQ ID NO 141
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-(3-methyl)-beta-Val-beta-
      Val-NH2
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Val9

<400> SEQUENCE: 141

Leu Asp His Phe Arg Trp Lys Val Val
1               5

<210> SEQ ID NO 142
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-(3-methyl)-beta-Val-beta-Pro-
      NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 142

Leu Asp Pro Phe Arg Trp Lys Val Pro
1               5

<210> SEQ ID NO 143
<211> LENGTH: 9
<212> TYPE: PRT
```

```
-continued

<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-(3-methyl)-beta-Val-beta-Pro-
      NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 143

Leu Asp His Phe Arg Trp Lys Val Pro
1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-(3-methyl)-beta-Val-beta-
      Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Pro9
```

-continued

```
<400> SEQUENCE: 144

Leu Asp Pro Phe Arg Trp Lys Val Pro
1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-(3-methyl)-beta-Val-beta-
      Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Pro9

<400> SEQUENCE: 145

Leu Asp His Phe Arg Trp Lys Val Pro
1               5

<210> SEQ ID NO 146
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-beta-Thr-beta-Pro-beta-Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
```

```
<221> NAME/KEY: MOD_RES
<222> LOCATION: (8)..(8)
<223> OTHER INFORMATION: beta-Thr8
<220> FEATURE:
<221> NAME/KEY: MOD_RES
<222> LOCATION: (9)..(9)
<223> OTHER INFORMATION: beta-Pro9
<220> FEATURE:
<221> NAME/KEY: MOD_RES
<222> LOCATION: (10)..(10)
<223> OTHER INFORMATION: beta-Thr10

<400> SEQUENCE: 146

Leu Asp Pro Phe Arg Trp Lys Thr Pro Thr
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-beta-Thr-beta-Pro-beta-Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Thr8
<220> FEATURE:
<221> NAME/KEY: MOD_RES
<222> LOCATION: (9)..(9)
<223> OTHER INFORMATION: beta-Pro9
<220> FEATURE:
<221> NAME/KEY: MOD_RES
<222> LOCATION: (10)..(10)
<223> OTHER INFORMATION: beta-Thr10

<400> SEQUENCE: 147

Leu Asp His Phe Arg Trp Lys Thr Pro Thr
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-beta-Thr-beta-Pro-beta-
      Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
```

```
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Thr8
<220> FEATURE:
<221> NAME/KEY: MOD_RES
<222> LOCATION: (9)..(9)
<223> OTHER INFORMATION: beta-Pro9
<220> FEATURE:
<221> NAME/KEY: MOD_RES
<222> LOCATION: (10)..(10)
<223> OTHER INFORMATION: beta-Thr10

<400> SEQUENCE: 148

Leu Asp Pro Phe Arg Trp Lys Thr Pro Thr
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-beta-Thr-beta-Pro-beta-
      Thr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Thr8
<220> FEATURE:
<221> NAME/KEY: MOD_RES
<222> LOCATION: (9)..(9)
<223> OTHER INFORMATION: beta-Pro9
<220> FEATURE:
<221> NAME/KEY: MOD_RES
<222> LOCATION: (10)..(10)
<223> OTHER INFORMATION: beta-Thr10
```

```
<400> SEQUENCE: 149

Leu Asp His Phe Arg Trp Lys Thr Pro Thr
1               5                   10

<210> SEQ ID NO 150
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-D-Pro-D-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Ala9

<400> SEQUENCE: 150

Leu Asp Pro Phe Arg Trp Lys Pro Ala
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-D-Pro-D-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Ala9
```

```
<400> SEQUENCE: 151

Leu Asp His Phe Arg Trp Lys Pro Ala
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-D-Pro-D-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Ala9

<400> SEQUENCE: 152

Leu Asp Pro Phe Arg Trp Lys Pro Ala
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-D-Pro-D-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
```

```
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Ala9

<400> SEQUENCE: 153

Leu Asp His Phe Arg Trp Lys Pro Ala
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-D-Ala-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Ala8
<220> FEATURE:
<221> NAME/KEY: MOD_RES
<222> LOCATION: (9)..(9)
<223> OTHER INFORMATION: AMIDATION; D-Pro9

<400> SEQUENCE: 154

Leu Asp Pro Phe Arg Trp Lys Ala Pro
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-D-Ala-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
```

```
          10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Ala8
<220> FEATURE:
<221> NAME/KEY: MOD_RES
<222> LOCATION: (9)..(9)
<223> OTHER INFORMATION: AMIDATION; D-Pro9

<400> SEQUENCE: 155

Leu Asp His Phe Arg Trp Lys Pro Ala
1               5

<210> SEQ ID NO 156
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-D-Ala-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Ala8
<220> FEATURE:
<221> NAME/KEY: MOD_RES
<222> LOCATION: (9)..(9)
<223> OTHER INFORMATION: AMIDATION; D-Pro9

<400> SEQUENCE: 156

Leu Asp Pro Phe Arg Trp Lys Ala Pro
1               5

<210> SEQ ID NO 157
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-D-Ala-D-Pro-NH2
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Ala8
<220> FEATURE:
<221> NAME/KEY: MOD_RES
<222> LOCATION: (9)..(9)
<223> OTHER INFORMATION: AMIDATION; D-Pro9

<400> SEQUENCE: 157

Leu Asp His Phe Arg Trp Lys Ala Pro
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-beta-Pro-beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Ala9

<400> SEQUENCE: 158

Leu Asp Pro Phe Arg Trp Lys Pro Ala
1               5

<210> SEQ ID NO 159
<211> LENGTH: 9
<212> TYPE: PRT
<213> ORGANISM: Artificial Sequence
<220> FEATURE:
```

```
<223> OTHER INFORMATION: Synthetic polypeptide:
      Ac-Nle-c[Asp-His-D-Phe-Arg-Trp-Lys]-beta-Pro-beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Ala9

<400> SEQUENCE: 159

Leu Asp His Phe Arg Trp Lys Pro Ala
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-beta-Pro-beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Ala9

<400> SEQUENCE: 160

Leu Asp Pro Phe Arg Trp Lys Pro Ala
1               5
```

```
<210> SEQ ID NO 161
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-beta-Pro-beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Ala9

<400> SEQUENCE: 161

Leu Asp His Phe Arg Trp Lys Pro Ala
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-beta-Ala-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Ala8
<220> FEATURE:
<221> NAME/KEY: MOD_RES
```

```
<222> LOCATION: (9)..(9)
<223> OTHER INFORMATION: AMIDATION; beta-Pro9

<400> SEQUENCE: 162

Leu Asp Pro Phe Arg Trp Lys Ala Pro
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-beta-Ala-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Ala8
<220> FEATURE:
<221> NAME/KEY: MOD_RES
<222> LOCATION: (9)..(9)
<223> OTHER INFORMATION: AMIDATION; beta-Pro9

<400> SEQUENCE: 163

Leu Asp His Phe Arg Trp Lys Pro Ala
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-beta-Ala-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
```

```
<223> OTHER INFORMATION: D-Lys7
<220> FEATURE:
<221> NAME/KEY: MOD_RES
<222> LOCATION: (8)..(8)
<223> OTHER INFORMATION: beta-Ala8
<220> FEATURE:
<221> NAME/KEY: MOD_RES
<222> LOCATION: (9)..(9)
<223> OTHER INFORMATION: AMIDATION; beta-Pro9

<400> SEQUENCE: 164

Leu Asp Pro Phe Arg Trp Lys Ala Pro
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-beta-Ala-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Ala8
<220> FEATURE:
<221> NAME/KEY: MOD_RES
<222> LOCATION: (9)..(9)
<223> OTHER INFORMATION: AMIDATION; beta-Pro9

<400> SEQUENCE: 165

Leu Asp His Phe Arg Trp Lys Ala Pro
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-beta-Val-beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
```

```
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 166

Leu Asp Pro Phe Arg Trp Lys Val Ala
1               5

<210> SEQ ID NO 167
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-beta-Val-beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 167

Leu Asp His Phe Arg Trp Lys Val Ala
1               5

<210> SEQ ID NO 168
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-beta-Val-beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
```

```
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 168

Leu Asp Pro Phe Arg Trp Lys Val Ala
1               5

<210> SEQ ID NO 169
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Nal(2')-Arg-Trp-D-Lys]-beta-Val-beta-Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 169

Leu Asp His Xaa Arg Trp Lys Val Ala
1               5

<210> SEQ ID NO 170
<211> LENGTH: 9
```

```
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-(3-methyl)-beta-Val-beta-Ala-
      NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 170

Leu Asp Pro Phe Arg Trp Lys Val Ala
1               5

<210> SEQ ID NO 171
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-(3-methyl)-beta-Val-beta-Ala-
      NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 171

Leu Asp His Phe Arg Trp Lys Val Ala
1               5

<210> SEQ ID NO 172
```

```
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-(3-methyl)-beta-Val-beta-
      Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 172

Leu Asp Pro Phe Arg Trp Lys Val Ala
1               5

<210> SEQ ID NO 173
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-(3-methyl)-beta-Val-beta-
      Ala-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
```

```
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Ala9

<400> SEQUENCE: 173

Leu Asp His Phe Arg Trp Lys Val Ala
1               5

<210> SEQ ID NO 174
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-D-Pro-D-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Leu9

<400> SEQUENCE: 174

Leu Asp Pro Phe Arg Trp Lys Pro Leu
1               5

<210> SEQ ID NO 175
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-D-Pro-D-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
```

```
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Leu9

<400> SEQUENCE: 175

Leu Asp His Phe Arg Trp Lys Pro Leu
1               5

<210> SEQ ID NO 176
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-D-Pro-D-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Leu9

<400> SEQUENCE: 176

Leu Asp Pro Phe Arg Trp Lys Pro Leu
1               5

<210> SEQ ID NO 177
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-D-Pro-D-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
```

```
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Pro8
<220> FEATURE:
<221> NAME/KEY: MOD_RES
<222> LOCATION: (9)..(9)
<223> OTHER INFORMATION: AMIDATION; D-Leu9

<400> SEQUENCE: 177

Leu Asp His Phe Arg Trp Lys Pro Leu
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-D-Leu-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Leu8
<220> FEATURE:
<221> NAME/KEY: MOD_RES
<222> LOCATION: (9)..(9)
<223> OTHER INFORMATION: AMIDATION; D-Pro9

<400> SEQUENCE: 178

Leu Asp Pro Phe Arg Trp Lys Leu Pro
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-D-Leu-D-Pro-NH2
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Leu8
<220> FEATURE:
<221> NAME/KEY: MOD_RES
<222> LOCATION: (9)..(9)
<223> OTHER INFORMATION: AMIDATION; D-Pro9

<400> SEQUENCE: 179

Leu Asp His Phe Arg Trp Lys Pro Leu
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-D-Leu-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Leu8
<220> FEATURE:
<221> NAME/KEY: MOD_RES
<222> LOCATION: (9)..(9)
<223> OTHER INFORMATION: AMIDATION; D-Pro9

<400> SEQUENCE: 180

Leu Asp Pro Phe Arg Trp Lys Leu Pro
1               5

<210> SEQ ID NO 181
<211> LENGTH: 9
<212> TYPE: PRT
```

```
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-D-Leu-D-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: D-Leu8
<220> FEATURE:
<221> NAME/KEY: MOD_RES
<222> LOCATION: (9)..(9)
<223> OTHER INFORMATION: AMIDATION; D-Pro9

<400> SEQUENCE: 181

Leu Asp His Phe Arg Trp Lys Leu Pro
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-beta-Pro-beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Leu9

<400> SEQUENCE: 182
```

Leu Asp Pro Phe Arg Trp Lys Pro Leu
1               5

<210> SEQ ID NO 183
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-beta-Pro-beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Leu9

<400> SEQUENCE: 183

Leu Asp His Phe Arg Trp Lys Pro Leu
1               5

<210> SEQ ID NO 184
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-beta-Pro-beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8

```
<220> FEATURE:
<221> NAME/KEY: MOD_RES
<222> LOCATION: (9)..(9)
<223> OTHER INFORMATION: AMIDATION; beta-Leu9

<400> SEQUENCE: 184

Leu Asp Pro Phe Arg Trp Lys Pro Leu
1               5

<210> SEQ ID NO 185
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-beta-Pro-beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa 4 = D-Nal(2'); D-(naphtha-2-yl)alanine
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Pro8
<220> FEATURE:
<221> NAME/KEY: MOD_RES
<222> LOCATION: (9)..(9)
<223> OTHER INFORMATION: AMIDATION; beta-Leu9

<400> SEQUENCE: 185

Leu Asp His Xaa Arg Trp Lys Pro Leu
1               5

<210> SEQ ID NO 186
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-beta-Leu-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
```

```
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Leu8
<220> FEATURE:
<221> NAME/KEY: MOD_RES
<222> LOCATION: (9)..(9)
<223> OTHER INFORMATION: AMIDATION; beta-Pro9

<400> SEQUENCE: 186

Leu Asp Pro Phe Arg Trp Lys Leu Pro
1               5

<210> SEQ ID NO 187
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-beta-Leu-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Leu8
<220> FEATURE:
<221> NAME/KEY: MOD_RES
<222> LOCATION: (9)..(9)
<223> OTHER INFORMATION: AMIDATION; beta-Pro9

<400> SEQUENCE: 187

Leu Asp His Phe Arg Trp Lys Pro Leu
1               5

<210> SEQ ID NO 188
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-beta-Leu-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
```

```
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Leu8
<220> FEATURE:
<221> NAME/KEY: MOD_RES
<222> LOCATION: (9)..(9)
<223> OTHER INFORMATION: AMIDATION; beta-Pro9

<400> SEQUENCE: 188

Leu Asp Pro Phe Arg Trp Lys Leu Pro
1               5

<210> SEQ ID NO 189
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-beta-Leu-beta-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Leu8
<220> FEATURE:
<221> NAME/KEY: MOD_RES
<222> LOCATION: (9)..(9)
<223> OTHER INFORMATION: AMIDATION; beta-Pro9

<400> SEQUENCE: 189

Leu Asp His Phe Arg Trp Lys Leu Pro
1               5

<210> SEQ ID NO 190
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-beta-Val-beta-Leu-NH2
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 190

Leu Asp Pro Phe Arg Trp Lys Val Leu
1               5

<210> SEQ ID NO 191
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-beta-Val-beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 191

Leu Asp His Phe Arg Trp Lys Val Leu
1               5

<210> SEQ ID NO 192
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-beta-Val-beta-Leu-NH2
<220> FEATURE:
```

<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 192

Leu Asp Pro Phe Arg Trp Lys Val Leu
1               5

<210> SEQ ID NO 193
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-beta-Val-beta-Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: beta-Val8
<220> FEATURE:
<221> NAME/KEY: MOD_RES
<222> LOCATION: (9)..(9)
<223> OTHER INFORMATION: AMIDATION; beta-Leu9

```
<400> SEQUENCE: 193

Leu Asp His Phe Arg Trp Lys Val Leu
1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Phe-Arg-Trp-Lys]-(3-methyl)-beta-Val-beta-Leu-
      NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 194

Leu Asp Pro Phe Arg Trp Lys Val Leu
1               5

<210> SEQ ID NO 195
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-His-D-Phe-Arg-Trp-Lys]-(3-methyl)-beta-Val-beta-Leu-
      NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
```

```
<223> OTHER INFORMATION: AMIDATION; beta-Leu9

<400> SEQUENCE: 195

Leu Asp His Phe Arg Trp Lys Val Leu
1               5

<210> SEQ ID NO 196
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-Pro-D-Phe-Arg-Trp-D-Lys]-(3-methyl)-beta-Val-beta-
      Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 196

Leu Asp Pro Phe Arg Trp Lys Val Leu
1               5

<210> SEQ ID NO 197
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[D-Asp-His-D-Phe-Arg-Trp-D-Lys]-(3-methyl)-beta-Val-beta-
      Leu-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: D-Asp2
<220> FEATURE:
<221> NAME/KEY: MOD_RES
<222> LOCATION: (2)..(7)
```

```
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Lys7
<220> FEATURE:
<221> NAME/KEY: MOD_RES
<222> LOCATION: (8)..(8)
<223> OTHER INFORMATION: (3-methyl)-beta-Val8
<220> FEATURE:
<221> NAME/KEY: MOD_RES
<222> LOCATION: (9)..(9)
<223> OTHER INFORMATION: AMIDATION; beta-Leu9

<400> SEQUENCE: 197

Leu Asp His Phe Arg Trp Lys Val Leu
1               5

<210> SEQ ID NO 198
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-D-Val-D-Pro-OH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: D-Val8
<220> FEATURE:
<221> NAME/KEY: MOD_RES
<222> LOCATION: (8)..(8)
<223> OTHER INFORMATION: D-Pro9

<400> SEQUENCE: 198

Leu Asp Pro Xaa Arg Trp Lys Val Pro
1               5

<210> SEQ ID NO 199
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta2-Val-beta3-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
```

```
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-2-Val8
<220> FEATURE:
<221> NAME/KEY: MOD_RES
<222> LOCATION: (9)..(9)
<223> OTHER INFORMATION: AMIDATION; beta-3-Pro9

<400> SEQUENCE: 199

Leu Asp Pro Xaa Arg Trp Lys Val Pro
1               5

<210> SEQ ID NO 200
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta3-Val-beta3-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-3-Val8
<220> FEATURE:
<221> NAME/KEY: MOD_RES
<222> LOCATION: (9)..(9)
<223> OTHER INFORMATION: AMIDATION; beta-3-Pro9

<400> SEQUENCE: 200

Leu Asp Pro Xaa Arg Trp Lys Val Pro
1               5

<210> SEQ ID NO 201
<211> LENGTH: 9
<212> TYPE: PRT
<213> ORGANISM: Artificial Sequence
<220> FEATURE:
<223> OTHER INFORMATION: Synthetic polypeptide:
      Ac-Nle-c[Asp-Pro-D-Nal(2')-Arg-Trp-Lys]-beta3-Pro-beta3-Pro-NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
```

```
<221> NAME/KEY: MOD_RES
<222> LOCATION: (2)..(7)
<223> OTHER INFORMATION: cyclization between Asp2 5-beta and Lys7
      10-epsilon
<220> FEATURE:
<221> NAME/KEY: MOD_RES
<222> LOCATION: (4)..(4)
<223> OTHER INFORMATION: Xaa4 = D-Nal(2'); D-(naphth-2-yl)alanine
<220> FEATURE:
<221> NAME/KEY: MOD_RES
<222> LOCATION: (8)..(8)
<223> OTHER INFORMATION: beta-3-Pro8
<220> FEATURE:
<221> NAME/KEY: MOD_RES
<222> LOCATION: (9)..(9)
<223> OTHER INFORMATION: AMIDATION; beta-3-Pro9

<400> SEQUENCE: 201

Leu Asp Pro Xaa Arg Trp Lys Pro Pro
1               5
```

MELANOCORTIN ANALOGS HAVING ENHANCED ACTIVITY AND TRANSPORT

RELATED APPLICATIONS

This application is a national stage application under 35 U.S.C. 371 of International Patent Application No. PCT/US2013/30528, filed on Mar. 12, 2013, that claims benefit of priority to U.S. Provisional Patent Application No. 61/610,149 filed Mar. 13, 2012, each of which is hereby incorporated by reference in its entirety.

TECHNICAL FIELD

Described herein are melanocortin analogs having enhanced activity and transport.

BACKGROUND

Melanocortins are a group of small peptides that bind to a family of five known melanocortin receptors (MC1R through MC5R). Cone, *Endocr. Rev.* 27(7): 736-749 (2006). They are derived from a common precursor protein, pro-opiomelanocortin (POMC), which is expressed in the neurons of the central and peripheral nervous system, and in the pituitary gland. Voisey et al., *Curr. Drug Targets* 4(7): 586-597 (2003). The proteolytic cleavage of POMC results in α-, β- and γ-melanocortin and adrenocorticotrophic hormone (ACTH), in addition to several other biologically important peptides. Smith and Funder, *Endocr. Rev.* 9(1): 159-179 (1988).

Of the five known melanocortin receptors, MC3R and MC4R are thought to be expressed predominantly in the mammalian brain, with MC3R being most highly expressed in the arcuate nucleus of the hypothalamus, and MC4R being expressed in the thalamus, hypothalamus, and hippocampus. Cone, *Nat. Neurosci.* 8(5): 571-578 (2005). C1R is expressed mainly in the periphery where it is found, for example, on melanoma cells and melanocytes and immune cells. In the neuronal system, MC1R is present only on neurons in the periaqueductal grey matter of the midbrain, where it is believed to have a role in controlling pain. MC2R is predominantly expressed in the adrenal cortex, where it controls steroidogenesis. MC5R is found predominantly in peripheral tissues such as the secretory epithelia of many exocrine glands, where it affects secretory and trophic controls.

Melanocortin peptides were initially thought to have a physiological function primarily directed to the control of skin pigmentation. Hadley and Dorr, *Peptides* 27(4): 921-930 (2006). However, in the last 25 years, many additional biological activities have been attributed to the melanocortins. Melanocortin peptides that are either agonists (activators) or antagonists (inhibitors) have been shown to control many physiological processes, including pigmentation, feeding, overall metabolic rate/energy homeostasis, endocrine and exocrine gland secretion, inflammation, sodium excretion by the kidney, pain sensation, addictive behavior, and sexual drive. Cone, *Nat. Neurosci.* 8(5): 571-578 (2005); Cone, *Endocr. Rev.* 27(7): 736-749 (2006).

Melanocortin analogs have been synthesized for the potential regulation and treatment of many conditions, including weight regulation (e.g., obesity, anorexia, and cachexia), hormonal secretion, and hyposecretion of many exocrine glands (e.g., Sjogren's syndrome), immuno-relevant conditions, and sexual dysfunction. Cone, *Nat. Neurosci.* 8(5): 571-578 (2005); Cone, *Endocr. Rev.* 27(7): 736-749 (2006); Bazzani et al., *Resuscitation* 52(1): 109-115 (2002); and Bertonlini et al., *Pharmacol. Res.* 59(1): 13-47 (2009). However, in regulating these physiological effects, melanocortin analogs have also been shown to cause hypertension. Gruber et al., *Hypertension* 6: 468-474 (1984); Klein et al. *Life Sciences* 36: 769-775 (1985). Experimental studies have shown that administration of melanocortin analogs (peptides) increases arterial pressure and heart rate, and can produce cardiac arrhythmias. Gruber and Callahan, *Am. J. Physiol.* 257: R681-R694 (1989); and unpublished data.

The physiological regulatory effects of a melanocortin peptide are achieved through the melanocortin pharmacophore: His-Phe-Arg-Trp (SEQ ID NO: 1). This pharmacophore is the minimum set of amino acids necessary for melanocortin-regulated activity. Holder and Haskel-Luevano, *Med. Res. Rev.*, 24(3): 325-356 (2004). In general, all melanocortin peptides share the same active core sequence: His-Phe-Arg-Trp, including melanotropin neuropeptides and adrenocorticotropin. The amino acids surrounding this core sequence in naturally occurring melanocortin peptides are believed to affect the relative affinity for a specific melanocortin receptor.

Various non-naturally occurring melanocortin analogs with enhanced affinity for melanocortin receptors have been synthesized. For example, Klemes et al., *Biochem. Biophys. Res. Comm.* 137(2): 722-728 (1986), synthesized the melanocortin analogs (Ac-Nle-Asp-His-Phe-Arg-Trp) (SEQ ID NO: 2) and (Ac-Nle-Asp-His-D-Phe-Arg-Trp) (SEQ ID NO: 3). These modified analogs show increased potency for melanotropic activity. Many other melanocortin analogs have been identified. See Balse-Srinivasan et al. *J. Med. Chem.* 46(17): 3728-3733 (2003).

Further examples of melanocortin analogs that have been synthesized, having increased potency, include: Ac-Nle-cyclo-Asp-His-Phe-Arg-Trp-Lys (SEQ ID NO: 4) and Ac-Nle-cyclo-Asp-His-D-Phe-Arg-Trp-Lys (SEQ ID NO: 5); al-Obeidi et al., *J. Med. Chem.* 32(12): 2555-2561 (1989); Ac-Nle-cyclo-Asp-His-D-Nal-2'-Arg-Trp-Lys (SEQ ID NO: 6) and Ac-cyclo-Cys-Glu-His-D-Nal-2'-Arg-Trp-Gly-Cys-Pro-Pro-Lys-Asp (SEQ ID NO: 7); Balse-Srinivasan et al., *J. Med. Chem.*, 46(17); 3728-3733 (2003); Ac-Nle-Glu-His-D-Phe-Arg-D-Trp-Gly (SEQ ID NO: 8); al-Obeidi et al., *Peptide Res.* 2(1): 140-146 (1989); and His-Phe-Arg-Trp-Gly-Lys-Pro-Val (SEQ ID NO: 9); Cone, *Neurosci.* 8(5): 571-578 (2005); Teixido et al., *Brain Res. Bull.*, 73: 103-107 (2007).

To date, there have been few, if any, attempts at structural modifications to reduce melanocortin peptide side effects or enhance melanocortin in vivo activity. Work on enhancing melanocortin activity has mainly been restricted to in vitro studies. However, sequentially improving a peptide-receptor interaction in an isolated system fails to examine the possibility that one is also improving an interaction with another unrelated receptor system. The basis for such an effect is found in the concept of "overlapping pharmacophores." Basic science has now shown numerous examples in which a natural or synthetic peptide with a (primary) pharmacophore for one receptor class also contains secondary pharmacophore(s) for a different receptor class that overlaps with the primary class. Agnes et al., *Peptides* 29(8): 1413-1423 (2008); Lee et al., *Biopolymers* 90(3): 433-438 (2008). When the secondary pharmacophore produces unwanted side effects, this may lead to the false conclusion that there are unacceptable consequences associated with the primary pharmacophore (i.e., a poor "therapeutic window"). Results herein show that a single structural derivatization can improve the activity of two overlapping pharmacophores: a D-Phe[7] substitution in ACTH[4-10] improves natriuresis (i.e., sodium excretion; a melanocortin 3 receptor mediated action), and enhances cardiovascular activity (an RFamide receptor dependent effect). Gruber et al., *Hypertension* 6(4): 468-474 (1984).

The existence of "pharmacophores within pharmacophores" is a statistical consequence of the numerous amino acid residue replacements that can be made within a pharmacophore sequence. "Conservative" amino acid substitutions, replacement of one amino acid residue with another of similar chemical properties, are historically based on the maintenance of secondary and tertiary protein structure and function. Vazquez et al., *Arch. Biochem. & Biophys.* 305(2): 448-453 (1993). Examples of this include lysine for arginine, or aspartic for glutamic acid: i.e., amino acids with similar side chains. However, there is now evidence for "conservative" amino acid substitutions that traverse traditional amino acid class boundaries but still maintain protein or peptide function.

For example, in addition to the traditional classes of naturally occurring amino acids, acidic, basic, neutral, and non-polar; there are cation, anion, and pi ($\pi$) classes. Cation-$\pi$ interactions are an example of a peptide-receptor binding property that can be produced by the attraction between a variety of cationic side chains of different amino acids residues and the center of an aromatic ring. The ring center has a partial negative charge due to the pi orbitals of the surrounding carbon atoms. Ma and Dougherty, *Chem. Rev.* 97(5): 1303-1324 (1997). For example; while Arg, Lys, and His are basic amino acids; when considered as part of the cation pair (to a $\pi$ residue), Gln and Asn can be added to this group. Further, while Tyr may be polar compared to non-polar Phe or Trp, all three of these amino acids can serve as the aromatic partner of a cation-$\pi$ binding pair. Therefore, a major limitation in recognizing a potential pharmacophore (or pharmacophores) in a given peptide sequence is that many amino acids are members of several different classification groups. Depending on the particular binding property in a ligand-receptor interaction, there may be numerous conservative substitutions available for a particular amino acid residue. Thus, unless one knows the precise types of binding that a residue is participating in, conservative substitutions are uncertain.

Given the numerous conservative substitutions that are possible for many amino acid residues, there are statistical limitations in producing large numbers of truly unique peptide pharmacophores. One approach to estimating the total number of pharmacophores that are potentially possible is to use the mathematical formula first proposed by Gamow to deduce the triplet codon for amino acid residue coding in DNA, i.e., what length of DNA base pairs or "code" raised to the power of the number of different DNA bases, will allow for the coding of at least 20 different amino acids? Gamow et al. Advances in biological and medical physics 4: 23-68 (1956). Given that the average linear peptide pharmacophore (analogous to a DNA codon) is 3-4 residues in length, with 6 known classes of amino acids (analogous to DNA base classifications) there are theoretically about ~700-4000 potential linear peptide pharmacophores. However, since many amino acids are members of more than one class, the number of unique pharmacophores is much less than theoretical calculations would predict.

The law of probability predicts that "synonymous pharmacophores" will naturally occur. Analogous to synonymous words, these different amino acid sequences can manifest very similar binding characteristics at a specific receptor, and thus produce similar biological activities. These pharmacophores may occur in isolation (a sequence variant of a known peptide pharmacophore), or within the sequence of a larger pharmacophore (i.e., producing an overlapping pharmacophore). These predictions can be verified by constructing conservative substitutions in many different pharmacophores (in particular with cation-$\pi$ substitutions), and then searching for receptor proteins that bind these sequences.

For example, conservative substitutions in the melanocortin pharmacophore produce 64 peptides with potentially synonymous biological activity, and can bind to the same receptor as the classic melanocortin sequence. Masman, et al. *Bioorganic Med. Chem.* 14(22): 7604-7614 (2006); Masman, et al. *Bioorganic Med. Chem.* 16(8): 4347-4358 (2008).

An additional example is found in the RFamide class of peptides; peptides ending in an arginine (R)-phenylalanine (F) C-terminal sequence. This sequence is potentially a cation-$\pi$ binding motif. Ma and Dougherty, *Chem. Rev.* 97(5): 1303-1324 (1997). That it is a cation-$\pi$ binding motif is verified by showing that synonyms of the RF pharmacophore based on conservative cation or $\pi$ amino acid substitutions have equivalent biological activity. Gaus, et al. *Biol. Bull.* 184: 322-329 (1993).

Because even small (e.g., di-peptide) pharmacophores can have many synonyms, larger pharmacophores may contain smaller known pharmacophores (or their synonyms) within their sequence. The potential for overlapping pharmacophores to be an unrecognized source of unanticipated side effects in drugs is underscored by the evidence for three unique pharmacophores within the melanocortin tetrapeptide sequence, i.e., melanocortin, RFamide, and $\delta$-opioid. Lee et al., *Biopolymers* 90(3): 433-438 (2008).

Traditional scientific literature searching (e.g., searching scientific databases such as PubMed) fails to reveal many examples of pharmacophore conservative substitutions. One approach for finding these examples is to use an Internet search engine, and search for the actual substituted pharmacophore sequence. This approach uses the three or single letter amino acid designators to construct the pharmacophore, with the entire structure placed in quotations. Using this approach with conservative sequence variants of the melanocortin pharmacophore; e.g., His-Trp-Arg-Phe or His-Phe-Lys-Trp; revealed a binding protein in fungi that may be the phylogenetic precursor of the melanocortin receptor class. Masman et al., *Bioorg. Med. Chem.* 14(22): 7604-7614 (2006). Using unique structural features, rather than total sequence homology, has become a recognized way to examine protein homology and phylogeny. Zhu et al., *Cell. Mol. Life. Sci.* 62(19-20): 2257-2269 (2005). Supporting evidence for a fungal melanocortin receptor precursor hypothesis is that the Lys-Pro-Val sequence, an "address" or enhancer sequence in the $\alpha$-melanocortin structure, serves a similar function to enhance peptide-binding to the fungal protein. Masman et al., *Bioorg. Med. Chem.* 16(8): 4347-4358 (2008).

An important aspect of "pharmacophores within pharmacophores" is the potential to specifically regulate their activity: i.e., specifically suppress or enhance one of an overlapping pair or group of pharmacophores. Previous studies have described the how to suppress the cardiovascular side effects of a C-terminal peptide pharmacophore, using a metabolically stable C-terminal extension, without adversely affecting the activity of the larger pharmacophore it overlapped with. WO 2011/026015. However, there are many different structural positions for peptide pharmacophores, e.g., at the C or N-terminus or deeper within the sequence of the peptide. While some pharmacophores give undesirable effects, others have therapeutic qualities. Selective regulation would be an extremely useful property in drug development.

While a reduction in a drug's side effects produces a relative increase in therapeutic activity; i.e., an increase in therapeutic index, stabilization of the C- and/or N-terminus can produce an absolute increase in therapeutic activity. For example, catabolism of ACTH (a 30-amino acid residue peptide) produces peptide fragments similar to ACTH[4-10]. Saez et al., *J. Biol. Chem.* 250(5): 1683-1689 (1975); Neidle and Kelly, *Arch. Biochem. Biophys.* 233(1): 115-126 (1984). These data suggest that the C-terminal sequence of ACTH is very sensitive to enzymatic degradation, because 29 C-terminal residues are lost compared to only 4 N-terminal amino acids. Thus, recognizing where to place a metabolically stable terminal extension on a peptide is crucial in the maximal enhancement of overall molecule stability.

SUMMARY

Described herein are melanocortin analogs having enhanced activity and transport. Some melanocortin peptides described herein have a metabolically stable C-terminal extension to minimize or abolish side effects, and potentiate therapeutic activity for use in the treatment of various pathological conditions. Also described herein are structural modifications to melanocortin peptides that enhance the therapeutic activity of overlapping pharmacophores for use in the treatment of various pathological conditions, and allow regulation of drug active transport through the gastrointestinal tract (oral activity) and drug access or the prevention of access to the central nervous system (transport through the blood-brain-barrier). The approaches described herein are applicable for the development of drugs that use cation-π binding to receptors to produce therapeutic actions.

One embodiment described herein, is a non-naturally occurring melanocortin analog comprising the sequence according to Formula I: $X^1X^2X^3R^1R^2R^3R^4R^5R^6R^7Y^1Y^2Y^3$, wherein: $X^1$, $X^2$, and $X^3$ represent optional stabilizing N-terminal residues or an amino acid residue mimetic; $R^1$ to $R^7$ represent residues of the melanocortin analog; and $Y^1$, $Y^2$, and $Y^3$ represent degradation-resistant C-terminal residues or an amino acid residue mimetic.

One aspect described herein is the non-naturally occurring melanocortin analog, wherein: $R^1$ is absent or is selected from the group consisting of cysteine, norleucine, acetylated norleucine, acetylated cysteine, D-phenylalanine, methylated D-phenylalanine, succinic acid, o-phtalic acid, tyrosine, aspartic acid, glutaric acid, CO-cis-CH=CH—CO, an n-pentanoyl group, and an n-hexanoyl group; $R^2$ is absent or is selected from the group consisting of proline, aspartic acid, glutamic acid, glycine, cysteine, norleucine, arginine, succinic acid, glutaric acid, CO-cis-CH=CH—CO, an n-pentanoyl group, and an n-hexanoyl group; $R^3$ is selected from the group consisting of histidine, histidine methylated at positions 1 or 3, D-proline, L-proline, D-Nal(2'), L-Nal(2'), succinic acid, tButGly, Hyp(Bzl), Mamb, Oic, norleucine, Aba, β-alanine, and Tic;
$R^4$ is selected from the group consisting of histidine, D-phenylalanine, L-phenylalanine, D-Nal(2'), pCl-D-Phe, and (o-Phe)Phe; $R^5$ is selected from the group consisting of arginine, homoarginine, ornithine, alanine, proline, Pip, Nip, Tic, Phg, Sar, and Azt; $R^6$ is selected from D-tryptophan, L-tryptophan, D-Nal(2'), L-Nal(2'), Tic, and Bip; $R^7$ is absent or is selected from the group consisting of glycine, glutamic acid, cysteine, lysine, and 2,3-diamino-propionic acid; wherein if $R^3$ is Aba, then $R^4$ is selected from the group consisting of D-Phe, D-Nal(2'), and pCl-D-Phe; and wherein if $R^2$ is an n-pentanoyl group or an n-hexanoyl group, then $R^1$, $Y^1$, $Y^2$, and $Y^3$ are absent.

One aspect described herein is the non-naturally occurring melanocortin analog, wherein the melanocortin analog is cyclized.

Another aspect described herein is the non-naturally occurring melanocortin analog, wherein: $X^1$ is selected from the group consisting of D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-isoleucine, L-isoleucine, β-isoleucine, and a piperazin-2-one ring; $X^2$ is absent or is selected from the group consisting of D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-isoleucine, L-isoleucine, β-isoleucine, and a piperazin-2-one ring; and $X^3$ is absent or is selected from the group consisting of D-cysteine, L-cysteine, D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, and a piperazin-2-one ring.

One aspect described herein is the non-naturally occurring melanocortin analog, wherein the N-terminus is modified by acylation.

Another aspect described herein is the non-naturally occurring melanocortin analog, wherein: $Y^1$ is absent or is D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, or a piperazin-2-one ring; $Y^2$ is absent or is D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, or a piperazin-2-one ring; and $Y^3$ is absent or is D-cysteine, L-cysteine, D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, or a piperazin-2-one ring.

Another aspect described herein is the non-naturally occurring melanocortin analog, wherein the C-terminus is modified by amidation.

Another embodiment described herein, is the non-naturally occurring melanocortin analog comprising the sequence according to Formula II: $X^1X^2X^3R^1R^2R^3R^4R^5R^6R^7R^8R^9Y^1Y^2Y^3$, wherein: $X^1$, $X^2$, and $X^3$ represent optional stabilizing N-terminal residues or an amino acid residue mimetic; $R^1$ to $R^9$ represent residues of the melanocortin analog; and $Y^1$, $Y^2$, and $Y^3$ represent degradation-resistant C-terminal residues or an amino acid residue mimetic.

One aspect described herein is the non-naturally occurring melanocortin analog, wherein: $R^1$ is L-tyrosine; $R^2$ is L-valine; $R^3$ is L-methionine, norleucine, L-cysteine, or L-penicillamine; $R^4$ is glycine, D-cysteine, L-cysteine, L-aspartic acid, or norleucine; $R^5$ is L-histidine, norleucine, L-proline, or Aib; $R^6$ is L-phenylalanine, D-Nal(2'), or L-Nal(2'); $R^2$ is L-arginine; $R^8$ is L-tryptophan or D-Nal(2'); and $R^9$ is absent or is L-aspartic acid, L-cysteine, L-penicillamine, or L-lysine.

Another aspect described herein is the non-naturally occurring melanocortin analog, wherein the melanocortin analog is cyclized.

One aspect described herein is the non-naturally occurring melanocortin analog, wherein: $X^1$ is selected from the group consisting of D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-isoleucine, L-isoleucine, β-isoleucine, and a piperazin-2-one ring; $X^2$ is absent or is selected from the group consisting of D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-isoleucine, L-isoleucine, β-isoleucine, and a piperazin-2-one ring; and $X^3$ is absent or is selected from the group consisting of D-cysteine, L-cysteine, D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, and a piperazin-2-one ring.

One aspect described herein is the non-naturally occurring melanocortin analog, wherein the N-terminus is modified by acylation.

Another aspect described herein is the non-naturally occurring melanocortin analog, wherein: $Y^1$ is absent or is D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, or a piperazin-2-one ring; $Y^2$ is absent or is D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, or a piperazin-2-one ring; and $Y^3$ is absent or is D-cystine, L-cysteine, of D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, or a piperazin-2-one ring.

Another aspect described herein is the non-naturally occurring melanocortin analog, wherein the C-terminus is modified by amidation.

Another embodiment described herein, is the non-naturally occurring melanocortin analog comprising SEQ ID NOs: 15-201.

Another aspect described herein is the non-naturally occurring melanocortin analog comprising SEQ ID NOs: 15-201, wherein the melanocortin analog can traverse the epithelium, the blood-brain barrier, or both.

Another aspect described herein is the non-naturally occurring melanocortin analog comprising SEQ ID NOs: 15-201, wherein the half-life is 10-fold, 100-fold, 1.000-fold, 10.000-fold, or >10.000-fold greater than a natural melanocortin peptide.

Another aspect described herein is the non-naturally occurring melanocortin analog comprising SEQ ID NOs: 15-201, wherein the side effects are suppressed or eliminated compared to a natural melanocortin peptide.

Another aspect described herein is the non-naturally occurring melanocortin analog comprising SEQ ID NOs: 15-201, wherein the melanocortin analog is effective in modulating one or more of cachexia, lethargy, appetite, sleep, arousal, libido, locomotion, cardiovascular anomalies, vasodilatation, hypertension, hypotension, sodium regulation, pain, pain perception, homeostasis, endocrine and exocrine gland secretion, inflammation, addictive behavior, increasing endogenous opioid activity, or decreasing opioid tolerance.

Another embodiment described herein is a pharmaceutical composition comprising the non-naturally occurring melanocortin analog comprising SEQ ID NOs: 15-201.

One aspect described herein is a pharmaceutical composition comprising the non-naturally occurring melanocortin analog comprising SEQ ID NOs: 15-201, further comprising a pharmaceutical salt.

Another aspect described herein is a pharmaceutical composition comprising the non-naturally occurring melanocortin analog comprising SEQ ID NOs: 15-201, wherein the side effects are reduced compared to a natural melanocortin.

Another embodiment described herein is a method of treating a disorder in a subject in need thereof comprising administering a non-naturally occurring melanocortin analog as described herein.

One aspect described herein, is a method of treating a disorder in a subject in need thereof comprising administering a non-naturally occurring melanocortin analog as described herein, wherein the administration route is intraperitoneal, intravenous, parenteral, subcutaneous, intramuscular, intracerebroventricular, or orally.

Another aspect described herein, is a method of treating a disorder in a subject in need thereof comprising administering a non-naturally occurring melanocortin analog as described herein, wherein the non-naturally occurring melanocortin analog crosses the blood-brain-barrier.

Another aspect described herein, is a method of treating a disorder in a subject in need thereof comprising administering a non-naturally occurring melanocortin analog as described herein, wherein the side effects are reduced compared to a natural melanocortin.

Another embodiment described herein is a means for treating cachexia comprising administering the non-naturally occurring melanocortin analog of any one of SEQ ID NOs: 15-201.

One aspect described herein is a means for treating cachexia comprising administering the non-naturally occurring melanocortin analog of any one of SEQ ID NOs: 15-201, wherein the side effects are reduced compared to a natural melanocortin.

Another embodiment described herein is a kit for treating for treating cachexia in a subject in need thereof, comprising individual containers containing, a pharmaceutical composition comprising a non-naturally occurring melanocortin analog comprising any one of the sequences of SEQ ID NOs: 16-201, a device for administering the pharmaceutical composition, a reagent for diluting the pharmaceutical composition, and instructions for use.

Another embodiment described herein is a non-naturally occurring melanocortin analog as substantially described herein with reference to and as illustrated by the accompanying text and drawings.

The scope of the embodiments, aspects, compositions, or methods described herein includes all possible combinations of aspects, embodiments, examples, and preferences herein described.

DETAILED DESCRIPTION

Figure 1:
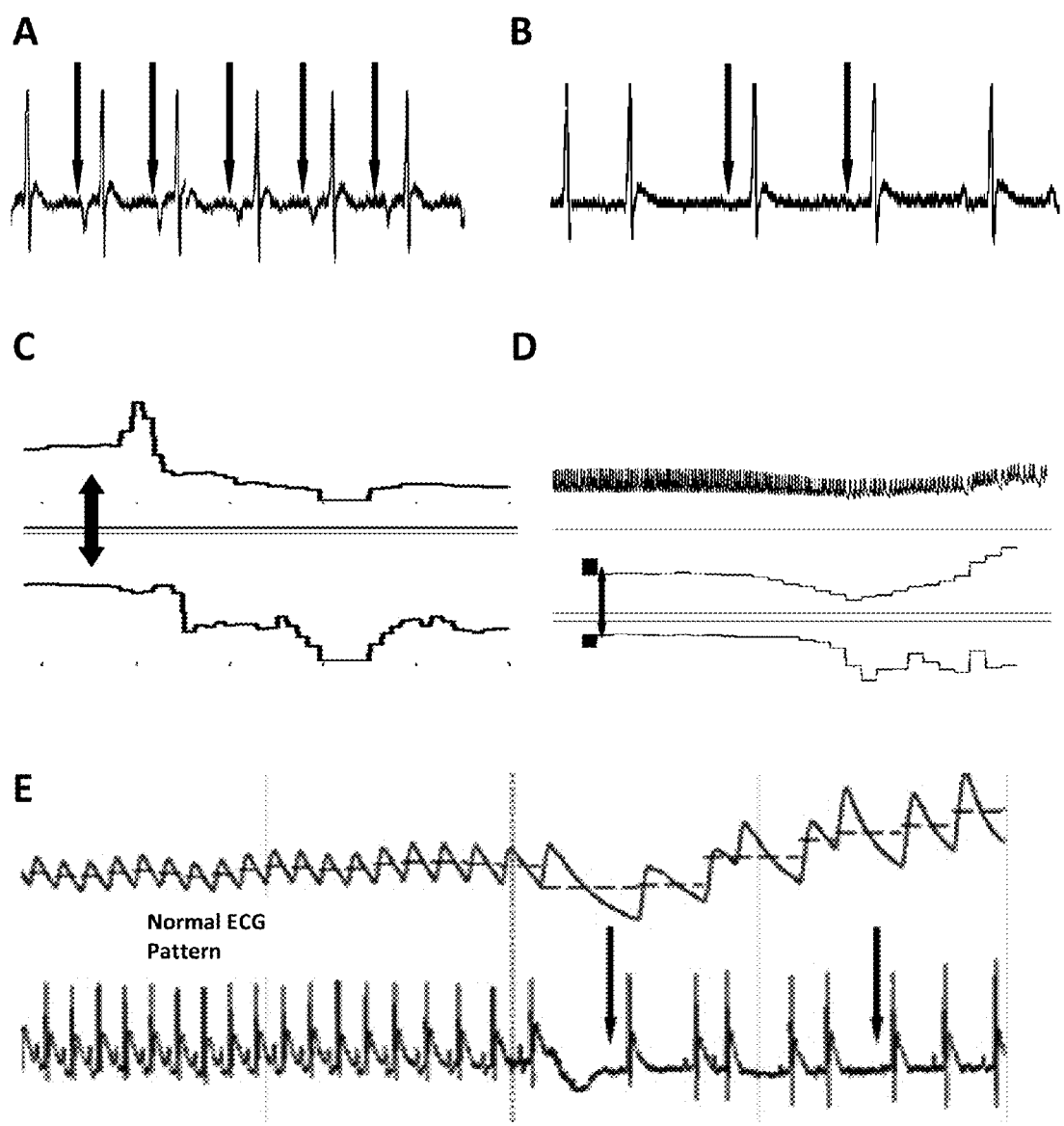
FIG. 1. Cardiovascular effects of melanocortins (MCs) in rats. (A) An ECG tracing (lead 2) from a rat given IV PT-141 (600 nmol/kg). Note the inverted P-wave (arrows). (B) An ECG tracing (lead 2) from a rat given IV MT-II (600 nmol/kg). Note the inconsistent presence of a P-wave (arrows). (C) The MAP (upper panel) and HR (lower panel) effects of a lethal dose of PT-141 (900 nmol/kg IV at arrow). Each y-axis block is 20 mm Hg or 60 BPM, while each x-axis block is 15 seconds. Baseline MAP was ~80 mmHg, rising to 140, before precipitously falling. Baseline heart rate was 312, and progressively fell. (D) A second by second tracing (1 block=1 sec) of the arterial pressure (upper panel), mean arterial pressure (MAP) (middle panel) and heart rate (bottom panel) produced by γ-melanocortin (150 nmol/kg IV dose at arrow). Bursts of tachycardia (~50 BPM) appear during a period of bradycardia, as MAP increases, a characteristic of tachybradycardia syndrome. Joung et al., *Am. J. Physiol.* 299(3): H634-642 (2010). (E) Arterial pressure response (upper panel, horizontal dashed line is MAP) to γ-melanocortin (150 nmol/kg, point of administration off screen to left), with a lead 2 ECG tracing (lower panel). γ-melanocortin produced ECGs with an intermittently suppressed P-wave (examples at arrows) during a bradycardia.

In the majority of therapeutic applications, melanocortin agents must be given systemically to produce an effect. Peptidic melanocortins need to be stabilized against enzymatic degradation, necessitating protective groups and/or additional residue/residues. These melanocortins must also be able to exhibit trans-epithelial transport, in order to have oral activity (gastrointestinal transport) and in some applications blood-brain barrier transport. According to the "Rule of Five," a molecular mass greater than 500 g/mol is one of the "violations" that prevent drug paracellular transport. Lipinski et al., *Adv. Drug Deliv. Rev.* 46(1-3): 3-26 (2001). Thus, most, if not all, peptide or peptide mimetic melanocortin pharmacophores would be unable to exhibit paracellular movement through the gastrointestinal tract or blood-brain-barrier. A potential way to surmount this problem is to use an active transport mechanism for trans-epithelial movement of a peptide drug. Active transport carriers for di- and tri-peptides have been described, and these transported peptides can serve as carriers for small cyclic peptides or non-peptide drugs. Brandsch, *Amino Acids* 31(2): 119-136 (2006); Brandsch et al., *J. Pharm. Pharmacol.* 60(5): 543-58 (2008). In one aspect described herein, a non-naturally occurring melanocortin peptide is provided and comprises a melanocortin analog coupled to a degradation resistant N- and/or C-terminal di or tri-peptide extension. One or both of the extensions contain a pharmacophore that enables active transport by di- or tri-peptide transport systems, conferring oral activity and/or blood-brain-barrier transport.

The melanocortin pharmacophore contains cation-π binding motifs and is able to activate other receptors where binding requires cation-π motifs. Ma and Dougherty, *Chem. Rev.* 97(5): 1303-1324 (1997); Agnes et al., *Peptides* 29(8): 1413-1423 (2008); Lee et al. *Biopolymers* 90(3): 433-438 (2008). There is evidence that it is possible to disproportionately enhance the expression of secondary overlapping pharmacophores as the activity of the primary pharmacophore increases.

The melanocortin pharmacophore has both natriuretic and cardiovascular activity, due to overlapping melanocortin and RF amide binding motifs. Gruber et al., *Hypertension* 6: 468-474 (1984); Gruber and Callahan, *Am. J. Physiol.* 257: R681-R694 (1989). However, when the pharmacophore is places within the full gamma melanocortin sequence cardiovascular activity is increased 10-fold, while natriuresis is enhanced >1000-fold. Klein et al., *Life Sci.* 36: 769-775 (1985); Lymangrover et al., *Endocrinology* 116(3): 1227-1229 (1985). The basis for these differences is the sigmoid dose-effect curve, in which drug concentration or administered dose is plotted against drug effect. The lower end of the curve shows a threshold effect, while the upper end of the curve is asymptotic. When a peptide produces a (primary) effect, this can be accompanied by the expression of side effects from secondary and/or overlapping pharmacophores. These secondary pharmacophores will probably have significantly less activity than the primary, since this secondary interaction has not been optimized. Thus, positions of each pharmacophore on a sigmoid dose-response curve will be significantly different. For example, the secondary pharmacophore may be down the sigmoid curve to the left of the primary pharmacophore. Thus, stabilization of a compound with two pharmacophores may produce disproportionate effects on the activity of each, depending on the relative position of each pharmacophore on the dose-response curve. When using N- and/or C-terminal di- or tri-peptide to stabilize a melanocortin peptide the expression of both primary and secondary pharmacophores can be modulated by increasing or decreasing the metabolic stability of the terminal peptide extension.

One aspect described herein, is non-naturally occurring melanocortin peptide that comprises a melanocortin analog coupled to a degradation resistant N- and/or C-terminal di or tri-peptide extension. The stabilizing effects of the extension(s) are designed to maximize the activity of overlapping pharmacophores with therapeutically desirable activity.

Another aspect described herein is a non-naturally occurring melanocortin peptide that comprises a melanocortin analog coupled to a degradation resistant N- and/or C-terminal di- or tri-peptide extension. The structure of the melanocortin analog and the peptide extension are designed to prevent a specific type of trans-epithelial transport. This analog would have utility when an orally active (i.e., having gastrointestinal transport) or when active only at peripheral sites of action (e.g., not within the central nervous system).

Another aspect described herein is a composition comprising a non-naturally occurring melanocortin peptide coupled to a degradation-resistant N- and/or C-terminal extension to suppress exposure and effects of overlapping pharmacophores, and potentiate therapeutic activity. The degradation-resistant extension is at least one amino acid, at least one modified amino acid, a peptide mimetic (non-amino acid small molecule), or combinations thereof. A degradation-resistant N- and/or C-terminal extension is one selected to resist degradation under physiological conditions, thereby allowing the melanocortin analog to enhance at least one melanocortin physiological regulatory effect while exhibiting minimized or abolished side effects and potentiated therapeutic activity when acutely or chronically administered to a human or mammal.

Described herein are peptides comprising non-naturally occurring melanocortin analogs comprising degradation-resistant N-terminal and/or C-terminal extensions.

"Melanocortin analogs," "melanocortin peptides," "melanocortins," or "peptides" are used interchangeably and refer to melanocortin-receptor ligands, which are macromolecules containing at least one melanocortin pharmacophore. Melanocortin analogs are typically peptides that bind melanocortin receptors under physiological conditions. Melanocortin analogs include non-naturally occurring melanocortin peptides and truncated and/or modified versions of melanocortin full-length protein or peptides. For example, the full-length pro-opiomelanocortin protein (POMC), prior to proteolytic cleavage of "sub-peptides," consists of 241 amino acids. Tissue-specific proteolytic cleavage of POMC yields peptides ranging in size from 13 amino acids to 76 amino acids. See Bicknell and Lawry, *Encyclopedia of Stress*, vol. 3, 257-265, Academic Press (2000). Synthesized, non-naturally occurring melanocortin analogs having increased melanocortin receptor activity as discussed herein are approximately 7-12 amino acids in size. Melanocortin analogs exhibit binding functionality with melanocortin receptors. The binding to the melanocortin receptor is either activating (agonist) or inhibitory (antagonist). In addition to peptides, the melanocortin analogs include small molecule analogs of melanocortin or portions thereof comprised of organic compounds, inorganic compounds, or a combinations of peptide and small molecule—i.e., peptide mimetics, or various combinations thereof.

"Melanocortin peptides" can be structurally similar and/or functionally similar to biological melanocortin proteins in their ability to bind melanocortin receptors. Further, the melanocortin analogs generally contain the pharmacophore: His-Phe-Arg-Trp (SEQ ID NO: 1) or a modified version thereof, or a structural or functional peptide mimetic thereof.

A peptide or amino acid "mimetic" is a non-amino acid molecule that mimics a peptide (a chain of amino acids) or one amino acid residue.

A "pharmacophore" is the minimum set of amino acid residues necessary to achieve a physiological effect; or a small molecule that is (with respect to a receptor) a structural mimic of the amino acid residues required for binding to and activation of a receptor. His-Phe-Arg-Trp (SEQ ID NO: 1) and their analogs are the pharmacophore of melanocortin for the regulated physiological effect. Therefore, non-naturally occurring melanocortin pharmacophore analogs can be small peptides or organic molecules designed to mimic the appearance or function (including activation or deactivation of receptor activity) of the melanocortin pharmacophore core sequence peptide.

"Side effects" refer to any unwanted (i.e., non-melanocortin) biological activity that occurs in conjunction with a therapeutic melanocortin effect.

"Potentiated therapeutic activity" refers to an increase in melanocortin activity in a melanocortin peptide that has undergone derivatization at the N- and/or C-terminus. Such derivatizations do not necessarily involve the pharmacophore, but do imply a relative increase in in vivo biological half-life.

"Substantial degradation" refers to the degradation of the N-terminal extension, the C-terminal extension, both N- and C-terminal degradation or degradation to other regions of the melanocortin peptide by physiological enzymes and other factors, in such a manner or to a degree that side effects appear. According to one aspect, a melanocortin analog having a C-terminal extension that resists substantial degradation is one where no more than 50% of the administered peptide causes side effects and/or displays a low half-life. In some aspects, no more than 25% of the administered peptide causes side effects and/or displays a low half-life. More preferably, in some aspects, less than 10% of the administered peptide causes side effects and/or displays a low half-life, as compared to a melanocortin analog that lacks a C-terminal extension.

A "pharmaceutical composition" includes melanocortin peptides described herein, or a pharmaceutically acceptable salt thereof, and a pharmaceutically acceptable carrier. The carrier may be a liquid formulation, for example, a buffered, isotonic, aqueous solution. Pharmaceutically acceptable carriers also can include excipients, such as diluents, carriers and the like, and additives, such as stabilizing agents, preservatives, solubilizing agents, buffers and the like.

The terms "bind," "binding," "complex," and "complexing," refer to all types of physical and chemical binding, reactions, complexing, attraction, chelating and the like.

The "peptides" described herein can be (a) naturally-occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides.

By employing chemical synthesis, a useful means of production, it is possible to introduce various amino acids which do not naturally occur along the chain, modify the N- or C-terminus, and the like, thereby providing for improved stability and formulation, resistance to protease degradation, and the like.

The term "peptide" as used herein includes any structure comprised of two or more amino acids, including chemical modifications and derivatives of amino acids. The amino acids forming all or a part of a peptide may be naturally occurring amino acids, stereoisomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" also includes dimers or multimers of peptides. A "manufactured" peptide includes a peptide produced by chemical synthesis, recombinant DNA technology, biochemical, or enzymatic fragmentation of larger molecules, combinations of the foregoing or, in general, made by any other method. The term "peptide" includes peptides containing a variable number of amino acid residues, optionally with non-amino acid residue groups at the N- and C-termini, such groups including acyl, acetyl, alkenyl, alkyl, N-alkyl, amine, or amide groups, among others.

"Amino acids" are molecules containing an amine group, a carboxylic acid group, and a side-chain that is specific to each amino acid. The key elements of an amino acid are carbon, hydrogen, oxygen, and nitrogen and have the generic formula $H_2N$—CHR—COOH, wherein R represents a side chain group. The various $\alpha$-amino acids differ in the side-chain moiety that is attached to the $\alpha$-carbon.

The phrase "amino acid side chain moiety" used herein, including as used in the specification and claims, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs, or structures designed to mimic amino acids, and the like. For example, the side chain moiety of any amino acid disclosed herein is included within the definition. A "derivative" of an amino acid side chain moiety is included within the definition of an amino acid side chain moiety.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties.

The "amino acids" used herein, and the term as used in the specification and claims, include the known naturally occurring protein amino acids, which are referred to by both their common three letter abbreviation and single letter abbreviation. See generally *Synthetic Peptides: A User's Guide*, G. A. Grant, editor, W.H. Freeman & Co., New York (1992), the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, supra; Hruby et al., *Biochem. J.* 268:249-262 (1990); and Toniolo, *Int. J. Peptide Protein Res.* 35:287-300 (1990); the teachings of all of which are incorporated herein by reference.

In the peptides described herein, conventional amino acid residues have their conventional meaning as given in Chapter 2400, of the *Manual of Patent Examining Procedure*, $8^{th}$ Ed. Thus, "Ala" is alanine; "Arg" is arginine; "Asn" is asparagine; "Asp" is aspartic acid; "Cys" is cysteine; "Gln" is glutamine; "Glu" is glutamic acid; "His" is histidine; "Ile" is isoleucine; "Leu" is leucine; "Lys" is lysine; "Met" is methionine; "Phe" is phenylalanine; "Pro" is proline; "Ser" is serine; Thr is threonine; "Trp" is tryptophan; "Tyr" is tryosine; and "Val" is valine. Unless otherwise indicated, all amino acids abbreviations represent either isomer, i.e., the L-isomer or the D-isomer. Thus, for example, "L-Phe" is L-phenylalanine; "D-Phe" is D-phenylalanine; "D-/L-Phe" is either D-phenylalanine or L-phenylalanine; "Phe" is also either D-phenylalanine or L-phenylalanine, and so on. Nonstandard amino acids are "Nle" is norleucine; "Nal" is noralanine; "D-Nal" is D-noralanine; D-Nal(2') is D-2'-naphthylalanine; and so on.

An alpha ($\alpha$)-amino acid has the generic formula $H_2N-C_\alpha HR-COOH$, where R is a side chain moiety and the amino group is attached to the carbon atom immediately adjacent to the carboxylate group (i.e., the $\alpha$-carbon). Other types of amino acid exist when the amino group is attached to a different carbon atom. For example, beta ($\beta$)-amino acids, the carbon atom to which the amino group is attached is separated from the carboxylate group by one carbon atom, $C_\beta$. For example, $\alpha$-alanine has the formula $H_2N-C_\alpha H(CH_3)-COOH$. In contrast, $\beta$-alanine has the general formula $H_2N-C_\beta H_2-C_\alpha H_2-COOH$ (i.e., 3-aminopropanoic acid).

When $\beta$-amino acids are incorporated into peptides, two main types of $\beta$-peptides exist: those with the side chain residue, R, on the carbon next to the amine are called $\beta^3$ peptides and those with the side chain residue on the carbon next to the carbonyl group are called $\beta^2$ amino acids. As a non-limiting example, "$\beta$-valine" can refer to:
—NH—$C_\beta H_2$—$C_\alpha H(CH_3)_2$—CO—, i.e., $\beta^2$-valine (R on carboxy side);
—NH—$C_\beta H(CH_3)_2$—$C_\alpha H_2$—CO—, i.e., $\beta^3$-valine (R on amino side); or
—NH—$C_\beta H(CH_3)_2$—$C_\alpha H(CH_3)_2$—CO—, i.e., $\beta^{2,3}$-valine (R at both positions).

Gamma ($\gamma$)-amino acids are amino acids with the carbon atom to which the amino group attaches is separated from the carboxylate moiety by two carbon atoms. For example, $\gamma$-amino butyric acid has the formula, $H_2N-C_\gamma H_2-C_\beta H_2-C_\alpha H_2-COOH$.

For additional modified and unusual amino acids, see §2422 of the MPEP, particularly Table 4 at 2400-24. Additionally, "Ac" indicates N-acetyl and "cyclo" refers to a cyclic structure, which is also shown in the literature as "c" or referred to as a "lactam." "$NH_2$" indicates an amine group, typically added on the C-terminus of a polypeptide. Accordingly, as used herein, an —$NH_2$ moiety on the C-terminus of a peptide indicates an amide, i.e., —CO—$NH_2$. In addition, the following abbreviations are used herein: Harg is Homo arginine; Hlys is Homo lysine; Nal(2') is D-(2'-naphthyl)alanine.

Additional abbreviations are used as follows: tBu is tert-butyl; Hyp(Bzl) is benzyl-L-hydroxy-proline; Mamb is 3-aminomethyl-benzoic acid; glutaric acid linker is CO—$(CH_2)_3$—CO; Pen is L-Penicillamine; Aib is 2-Aminoisobutyric acid; Tic is 1,2,3,4-Tetrahydroisoquinoline-3-carboxylic Acid; Aba is 4-amino-1,2,4,5-tetra-hydro-2-benzazepin-3-one; Pip is piperidine-2-carboxylic acid; Nip is piperidine-3-carboxylic acid; Tic is tetrahydroquinoline-3-carboxylic acid; Bipisbiphenylalanine; Phg is $\alpha$-Phenyl-glycine; Sar is Sarcosine; Azt is 3'-azido-3'-deoxythymidine; Oic is Octohydroindole-2-carboxylic acid.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monovalent or bicyclic aromatic hydrocarbon radical of 6-to-12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—, referred to herein as "Ac."

A peptide or aliphatic moiety is "acylated" when an alkyl or substituted alkyl group as defined above is bonded through one or more carbonyl {—(C=O)—} groups. A peptide is most usually acylated at the N-terminus.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen, and sulfur. Five- or six-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine, and thienopyridine.

An "amine" includes compounds that contain an amine group (—NH$_2$).

An "amide" includes compounds that have a trivalent nitrogen attached to a carbonyl group (i.e., —CO—NH$_2$), such as for example methylamide, ethylamide, propylamide, and the like. A peptide is most usually amidated at the C-terminus by the addition of an amine (—NH$_2$) moiety to the C-terminal carboxyl group.

An "imine" includes compounds that have a carbon-nitrogen double bond, with the nitrogen also attached to a hydrogen (NH=CH—R).

An "imide" includes compounds containing an imido group (—OC—NH—CO—).

A "nitrile" includes compounds that are carboxylic acid derivatives and contain a (—CN) group bound to an organic group.

The term "halogen" is intended to include the halogen atoms fluorine, chlorine, bromine and iodine, and groups including one or more halogen atoms, such as —CF$_3$ and the like.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions encompass any composition made by admixing a peptide and a pharmaceutically acceptable carrier.

Amino acids, including stereoisomers and modifications of naturally occurring amino acids, protein amino acids, non-protein amino acids, post-translationally modified amino acids, enzymatically synthesized amino acids, derivatized amino acids, constructs, or structures designed to mimic amino acids (peptide mimetics), and the like, including all of the foregoing, are sometimes referred to herein as "residues."

A melanocortin receptor "agonist" is a naturally occurring substance or manufactured drug substance or composition that can interact with a melanocortin receptor and initiate a pharmacological response characteristic of the melanocortin receptor. By a melanocortin receptor "antagonist" is a naturally occurring substance or manufactured drug substance or composition that opposes the melanocortin receptor-associated responses normally induced by a melanocortin receptor agonist agent. A melanocortin receptor "inverse agonist" is a drug or a compound that stabilizes the inactive conformation of the melanocortin receptor and inhibits basal activity.

"Cachexia" refers to a state of general ill health and malnutrition. It is often associated with and induced by malignant cancer, cystic fibrosis, or AIDS, and is characterized by loss of appetite, loss of body mass, especially lean body mass, and muscle wasting.

"Anorexia" refers simply to a loss of appetite, whether brought on by medical, physiological, or psychological factors. Anorexia is often closely associated with, and generally contributes to, cachexia seen in patients with advanced cancers and other conditions.

Melanocortin Analogs

A non-naturally occurring melanocortin analog is represented by Formula I, as shown, and comprises a melanocortin analog coupled to a degradation-resistant C-terminal extension and an optional N-terminal extension:

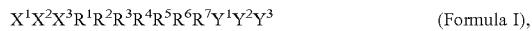
$$X^1X^2X^3R^1R^2R^3R^4R^5R^6R^7Y^1Y^2Y^3 \quad \text{(Formula I)},$$

wherein $X^1$, $X^2$, and $X^3$ represent optional stabilizing N-terminal residues or an amino acid residue mimetic; $R^1$ to $R^7$ represent residues of the melanocortin analog; and $Y^1$, $Y^2$, and $Y^3$ represent degradation-resistant C-terminal residues or an amino acid residue mimetic.

Collectively, $R^1$ to $R^7$ (i.e., $R^1R^2R^3R^4R^5R^6R^7$) can be one of many known melanocortin analogs, wherein each of the seven residues is independently an amino acid or peptide mimetic. Some melanocortin analogs have less than seven residues. In one aspect, $R^1$ to $R^7$, collectively, represent alpha ($\alpha$)-melanocortin analogs. In another aspect, $R^1$ to $R^7$, collectively, represent melanocortin analogs, which bind to MC3, MC4, and/or MC5 receptors as agonists or antagonists.

In one aspect, the melanocortin analog is represented by Formula I above, and residues $R^1$ to $R^7$, collectively, represent the melanocortin analog, wherein:

$R^1$ is absent or is selected from the group consisting of cysteine, norleucine, acetylated norleucine, acetylated cysteine, D-phenylalanine, methylated D-phenylalanine, succinic acid, o-pthalic acid, tyrosine, aspartic acid, glutaric acid, CO-cis-CH=CH—CO, an n-pentanoyl group, and an n-hexanoyl group;

$R^2$ is absent or is selected from the group consisting of proline, aspartic acid, glutamic acid, glycine, cysteine, norleucine, arginine, succinic acid, glutaric acid, CO-cis-CH=CH—CO, an n-pentanoyl group, and an n-hexanoyl group;

$R^3$ is selected from the group consisting of histidine, histidine methylated at positions 1 or 3, D-proline, L-proline, D-Nal(2'), L-Nal(2'), succinic acid, tButGly, Hyp(Bzl), Mamb, Oic, norleucine, Aba, β-alanine, and Tic;

$R^4$ is selected from the group consisting of histidine, D-phenylalanine, L-phenylalanine, D-Nal(2'), pCl-D-Phe, and (o-Phe)Phe;

$R^5$ is selected from the group consisting of arginine, homoarginine, ornithine, alanine, proline, Pip, Nip, Tic, Phg, Sar, and Azt;

$R^6$ is selected from D-tryptophan, L-tryptophan, D-Nal(2'), L-Nal(2'), Tic, and Bip;

$R^7$ is absent or is selected from the group consisting of glycine, glutamic acid, cysteine, lysine, and 2,3-di-amino-propionic acid;

wherein if $R^3$ is Aba, then $R^4$ is selected from the group consisting of D-Phe, D-Nal(2'), and pCl-D-Phe; and wherein if $R^2$ is an n-pentanoyl group or an n-hexanoyl group, then $R^1$, $Y^1$, $Y^2$, and $Y^3$ are absent.

In another aspect, the melanocortin analog is represented by Formula II and comprises a melanocortin analog coupled to a degradation-resistant C-terminal extension and an optional N-terminal extension:

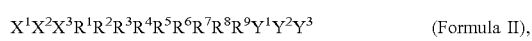
$$X^1X^2X^3R^1R^2R^3R^4R^5R^6R^7R^8R^9Y^1Y^2Y^3 \quad \text{(Formula II)},$$

wherein $X^1$, $X^2$, and $X^3$ represents optional stabilizing N-terminal residues or an amino acid residue mimetic; $R^1$ to $R^9$ (i.e., $R^1R^2R^3R^4R^5R^6R^7R^8R^9$) represent residues of the melanocortin analog; and $Y^1$, $Y^2$, and $Y^3$ represent degradation-resistant C-terminal residues or an amino acid residue mimetic. Collectively, $R^1$ to $R^9$ can be one of many known melanocortin analogs, wherein each of the nine residues is an amino acid or peptide mimetic. Some melanocortin analogs have less than nine residues. In one embodiment, $R^1$ to R⁹, collectively, represent gamma melanocortin analogs. In another embodiment, R¹ to R⁹, collectively, represent melanocortin analogs that bind to MC3 or MC4 receptors as antagonists.

In one aspect, the melanocortin analog is represented by Formula II above, and residues R¹ to R⁹, collectively, represent the melanocortin analog, wherein:
- R¹ is L-tyrosine;
- R² is L-valine;
- R³ is L-methionine, norleucine, L-cysteine, or L-penicillamine;
- R⁴ is glycine, D-cysteine, L-cysteine, L-aspartic acid, or norleucine;
- R⁵ is L-histidine, norleucine, L-proline, or Aib;
- R⁶ is L-phenylalanine, D-Nal(2'), or L-Nal(2');
- R⁷ is L-arginine;
- R⁸ is L-tryptophan or D-Nal(2'); and
- R⁹ is absent or is L-aspartic acid, L-cysteine, L-penicillamine, or L-lysine.

In another aspect, a melanocortin analog represented by Formula I or Formula II is provided, wherein at least one D-phenylalanine residue, or all D-phenylalanine residues are halogenated (e.g., fluorine or chlorine) to confer improved melanocortin analog interaction with the corresponding melanocortin receptor(s). Ippolito et al., *Int. J. Biol. Macromol.* 14(4): 193-197 (1992).

N-Terminal Extensions

In one aspect, an N-terminal extension is coupled to the melanocortin analog. The N-terminal extension is represented as X¹X²X³ in Formula I, wherein
- X¹ is selected from the group consisting of D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-isoleucine, L-isoleucine, β-isoleucine, and a piperazin-2-one ring;
- X² is absent or is selected from the group consisting of D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-isoleucine, L-isoleucine, β-isoleucine, and a piperazin-2-one ring; and
- X³ is absent or is selected from the group consisting of D-cysteine, L-cysteine, D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, and a piperazin-2-one ring.

In another aspect, an N-terminal extension is represented as X¹X²X³ in Formula II, wherein
- X¹ is selected from the group consisting of D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-isoleucine, L-isoleucine, β-isoleucine, and a piperazin-2-one ring;
- X² is absent or is selected from the group consisting of D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-isoleucine, L-isoleucine, β-isoleucine, and a piperazin-2-one ring; and
- X³ is absent or is selected from the group consisting of D-cysteine, L-cysteine, D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, and a piperazin-2-one ring.

In another aspect, a melanocortin analog represented by Formula I or Formula II containing any of the above N-terminal Extensions, X¹, X², or X³ may be modified on the N-terminus by acylation (CH₃—CO—). Melanocortins having such modifications are described in the Sequence Listing as "ACETYLATION."

C-Terminal Extensions

To the R¹ to R⁷ melanocortin analog of Formula I, or to the R¹ to R⁹ melanocortin analog of Formula II, a C-terminal extension is provided in order to confer degradation-resistance of the C-terminal extension to prevent exposure of the RFamide sequence, and to potentially confer trans-epithelial transport.

In one aspect the C-terminal extension is represented by Y¹Y²Y³ of Formula I, wherein
- Y¹ is absent or is D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, or a piperazin-2-one ring;
- Y² is absent or is D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, or a piperazin-2-one ring; and
- Y³ is absent or is D-cysteine, L-cysteine, D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, or a piperazin-2-one ring.

In another aspect, the C-terminal extension is represented by Y¹Y²Y³ of Formula II, wherein
- Y¹ is absent or is D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, or a piperazin-2-one ring;
- Y² is absent or is D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, or a piperazin-2-one ring; and
- Y³ is absent or is D-cystine, L-cysteine, of D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, or a piperazin-2-one ring.

In one aspect, the C-terminal extension has a conformation that chronically inhibits degradation from carboxy peptidases. Examples of a C-terminal extension that chronically inhibit degradation include the di- and tri-peptides: D-Pro-D-Pro; D-Thr-D-Pro; and D-Thr-D-Pro-D-Thr as described in Tugyi et al., *Proc. Natl. Acad. Sci. USA* 102(2): 413-418 (2005). Other examples of C-terminal extensions that inhibit C-terminal degradation are D-Pro-D-Val; D-Val-D-Pro; β-Val-β-Pro; β-Pro-β-Val; 3-methyl-β-Val-β-Pro; D-Pro-D-Ala; D-Ala-D-Pro; β-Pro-β-Ala; β-Ala-β-Pro; D-Pro-D-Leu; D-Leu-D-Pro; β-Pro-β-Leu; β-Leu-β-Pro; D-Val-D-Ala; D-Ala-D-Val; β-Val-β-Ala; β-Ala-β-Val; 3-methyl-β-Val-β-Ala; D-Val-D-Leu; D-Leu-D-Val; β-Val-β-Leu; β-Leu-β-Val; 3-methyl-β-Val-β-Leu; and others.

In another aspect, a melanocortin analog represented by Formula I or Formula II containing any of the above C-terminal Extensions, $Y^1$, $Y^2$, or $Y^3$ may be modified on the C-terminus by adding an amine group (—NH$_2$) to form an amide (i.e., —CO—NH$_2$). Melanocortins having such modifications are described in the Sequence Listing as "AMIDATION."

In another aspect, a proline mimetic (piperazin-2-one ring) is substituted for D-Pro. In one approach, a proline mimetic is synthesized as described in Teixido et al., *Brain Res Bull,* 2007, 73(1-3): 103-107. The piperazin-2-one ring is also discussed in Bhatt and Just, *Helvetica Chimica Acta* 83: 722-727 (2000). For the replacement of proline with a piperazin-2-one ring, an ethylene bridge is incorporated between the nitrogen molecules of two adjacent α-amino groups. This produces a six-membered ring, containing two nitrogen and four carbon atoms, a structure that is similar to a proline ring (albeit six-membered) between the two adjacent amino acid residue functional groups.

The C-terminal extension of the melanocortin analog is resistant to substantial degradation prior to the peptide being cleared from the bloodstream in the human or animal body. A C-terminal extension is of sufficient stability such that the melanocortin analog does not cause cardiovascular effects, or has minimized cardiovascular effects when administered to a human or animal. As stability of peptides, amino acids, and small molecules varies widely, melanocortin analogs described herein have variable length C-terminal extensions in the extracellular physiological environment. The C-terminal extension is of sufficient stability (e.g., length, steric structure) such that any degradation in the body prior to clearance from the bloodstream will not re-expose the cardiovascular (RFamide) pharmacophore to achieve the effect.

Cyclization of the Melanocortin Analog Comprising Formula I

Cyclized melanocortin analogs have shown improved efficacy and stability. See Balse-Srinivasan et al., *J. Med. Chem.* 46(17): 3728-3733 (2003) and Bednarek et al., *Biochem. Biophys. Res. Com.* 286(3): 641-645 (2001); Kavarana, et al., *J. Med. Chem.* 45(12): 2644-2650 (2002). In one aspect, the non-naturally occurring melanocortin analog represented by Formula I is cyclized. The following represents a non-limiting list of examples of how the melanocortin analog represented by Formula I can be cyclized:

In Formula I, disulfide bond between $R^1$ or $R^2$ and $R^7$ or $Y^1$, when $R^1$ or $R^2$ is cysteine and $R^7$ or $Y^1$ is cysteine as described in Balse-Srinivasan et al., *J. Med. Chem.,* 2003, 46(23): 4965-4973. When $Y^1$ is cysteine, $Y^2$ is not absent, but is selected from the group consisting of D-threonine, L-threonine, D-proline, L-proline and a piperazin-2-one ring.

A lactam bridge between $R^1$ and $R^7$, when $R^1$ is norleucine and $R^7$ is glutamic acid, as described in Mayorov et al. *J. Med. Chem.* 49: 1946-1952 (2006) and Bednarek et al., *Biochem. Biophys. Res. Com.* 286(3): 641-645 (2001).

A side-chain lactam bridge between $R^2$ and $R^7$, when $R^2$ is glutamic acid or aspartic acid and $R^7$ is lysine, as described in Bednarek et al., *Biochem. Biophys. Res. Com.* 286(3): 641-645 (2001).

A lactam bridge between $R^1$ and $R^7$, when $R^1$ is succinic acid or o-pthalic acid and $R^7$ is lysine, as described in Bednarek et al., *Biochem. Biophys. Res. Com.* 286(3): 641-645 (2001) and Kavarana et al., *J. Med. Chem.* 45(12): 2644-2650 (2002).

A lactam bridge between $R^2$ or $R^3$ and $R^7$, when $R^2$ or $R^3$ is succinic acid and $R^7$ is 2,3-diamino-propionic acid as described in Bednarek et al., *Biochem. Biophys. Res. Com.* 286(3): 641-645 (2001).

A "backbone" cyclized peptide is formed by covalent bond formation between the C- and/or N-terminus of a linear peptide of interest. An example of this is described in the bonding of two amide nitrogens via a bridge consisting of alkyl groups and an amide, as described by Hess et al., *J. Med. Chem.* 50: 6201-6211 (2007).

Amino Acids—Isomers and Non-Standard Amino Acids

In one aspect, the amino acid residues, as provided herein for the non-naturally occurring melanocortin analog described herein, can be either D- or L-amino acids or can be substituted with their non-standard, isomeric counterparts. For example, α-amino acids can be substituted with β-amino acids, and L-amino acids can be substituted with D-amino acids. An amino acid disclosed herein that is not designated as a D- or L-isomer, can be either isomer. All amino acids are α-amino acids, unless specifically indicated as β-amino acids. A β-amino acid can be either a $β^2$-amino acid or a $β^3$-amino acid, or both $β^2$ and $β^3$ in some cases, unless a specific designation is provided.

Cyclization of the Melanocortin Analog of Formula II

In one aspect, the non-naturally occurring melanocortin analog represented by Formula II is cyclized. The melanocortin analog represented by Formula II can be cyclized through a lactam side chain between $R^4$ and $R^9$ when $R^4$ is aspartic acid and $R^9$ is lysine, as described. See Bednarek et al., *Biochem. Biophys. Res. Com.* 286(3): 641-645 (2001) and Mayorov et al., *J. Med. Chem.* 49: 1946-1952 (2006).

Receptor Agonist and Antagonists

In another aspect, the non-naturally occurring melanocortin analog is an MC4 receptor agonist, an MC4 receptor antagonist, an MC3 receptor agonist, an MC3 receptor antagonist, and/or an MC5 agonist, of the α-melanocyte-stimulating hormone (MSH) group.

In another aspect, the non-naturally occurring melanocortin analog is an MC3 antagonist of the gamma melanocyte-stimulating hormone group.

In another aspect, the non-naturally occurring melanocortin analog is an MC3 agonist of the gamma melanocyte-stimulating hormone group.

Peptide Synthesis

The melanocortin analogs described herein may be readily synthesized by any known conventional procedure for the formation of a peptide linkage between amino acids. Such conventional procedures include, for example, any solution phase procedure permitting a condensation between the free alpha amino group of an amino acid or residue thereof having the carboxyl group or other reactive groups protected and the free primary carboxyl group of another amino acid or residue thereof having the amino group or other reactive groups protected. In an exemplary procedure, the peptides described herein may be synthesized by solid-phase synthesis and purified according to methods known in the art. Any of a number of well-known procedures utilizing a variety of resins and reagents may be used to prepare the peptides described herein.

The process for synthesizing the peptides may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide. The resulting peptide is then cyclized to yield a cyclic peptide.

Solid phase peptide synthesis methods are well known and practiced in the art. In such methods, the synthesis of peptides can be carried out by sequentially incorporating the desired amino acid residues one at a time into the growing peptide chain according to the general principles of solid phase methods. These methods are disclosed in numerous references, including Merrifield, *Angew Chem.* 24:799-810 (1985) and Barany et al., *The Peptides, Analysis, Synthesis and Biology*, Vol. 2, Gross E. and Meienhofer J., Eds. Academic Press 1-284 (1980).

In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting for solid phase synthesis methods and solution phase synthesis methods groups are known to those having ordinary skill in the art.

Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. Fmoc is useful for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf) and Boc. Pmc is a useful protecting group for Arg.

Solid phase synthesis is commenced from the C-terminal end of the peptide by coupling a protected alpha amino acid to a suitable resin. Such starting material is prepared by attaching an alpha amino-protected amino acid by an ester linkage to a p-benzyloxybenzyl alcohol (Wang) resin or a 2-chlorotrityl chloride resin, by an amide bond between an Fmoc-Linker, such as p-[(R,S)-α-[1-(9H-fluor-en-9-yl)-methoxyformamido]-2,4-dimethyloxybenzyl]-phenoxyacetic acid (Rink linker) to a benzhydrylamine (BHA) resin, or by other means well known in the art. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in N,N-dimethylformamide (DMF) may be used for this purpose.

Following removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide.

Reactive groups in a peptide can be selectively modified, either during solid phase synthesis or after removal from the resin. For example, peptides can be modified to obtain N-terminus modifications, such as acetylation, while on resin, or may be removed from the resin by use of a cleaving reagent and then modified. Methods for N-terminus modification, such as acetylation, and for C-terminus modification, such as amidation, are known in the art. Similarly, methods for modifying side chains of amino acids are well known to those skilled in the art of peptide synthesis. The choice of modifications made to reactive groups present on the peptide will be determined, in part, by the characteristics that are desired in the peptide.

The peptide can be cyclized prior to cleavage from the peptide resin. For cyclization through reactive side chain moieties, the desired side chains are deprotected, and the peptide suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), benzotriazole-1-yl-oxy-tris(dimethylamino) phosphoniumhexafluorophosphate (BOP), benzotriazole-1-yl-oxy-tris(pyrrolidino)phosphoniumhexafluorophosphate (PyBOP), 2-(7-aza-1H-benzotriazol-1-yl)-1,1,3,3-tetramethyluronium tetrafluoroborate (TATU), 2-(2-oxo-1 (2H)-pyridyl)-1,1,3,3-tetramethyluronium tetrafluoroborate (TPTU) or N,N'-dicyclohexylcarbodiimide/1-hydroxybenzotriazole (DCCl/HOBt). Coupling is convention initiated by use of a suitable base, such as N,N-diisopropylethylamine (DIPEA), sym-collidine or N-methylmorpholine (NMM).

Following cleavage of peptides from the solid phase following their synthesis, the peptide can be purified by any number of methods, such as reverse phase high performance liquid chromatography (RP-HPLC), using a suitable column, such as a $C_{18}$ column. Other methods of separation or purification, such as methods based on the size or charge of the peptide, can also be employed. Once purified, the peptide can be characterized by any number of methods, such as high performance liquid chromatograph (HPLC), amino acid analysis, mass spectrometry, and the like.

Formulation

The melanocortin analogs disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary application can involve human patients, but may be applied to laboratory, farm, zoo, wildlife, pet, sport, or other animals.

In general, the melanocortin analogs described herein may be synthesized by solid-phase synthesis and purified according to methods known in the art. Any of a number of well-known procedures utilizing a variety of resins and reagents may be used to prepare the peptides described herein.

Salt Forms of Peptides

The melanocortin analog peptides described herein may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Exemplary salts are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the peptides described herein are basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the peptides described herein are prepared in a suitable solvent from the peptide and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the peptides described herein include an acidic moiety, suitable pharmaceutically acceptable salts may include alkali metal salts, such as sodium or potassium salts, or alkaline earth metal salts, such as calcium or magnesium salts.

Pharmaceutical Compositions

Also described herein are pharmaceutical composition that includes a melanocortin analog peptide and a pharmaceutically acceptable carrier. The carrier may be a liquid formulation, and can be a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The peptides described herein may be formulated or compounded into pharmaceutical compositions that include at least one peptide together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride, and sodium citrate. For injection or other liquid administration formulations, water containing at least one or more buffering constituents is useful, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide described herein over a period of time.

In general, the actual quantity of peptides administered to a patient will vary between fairly wide ranges depending on the mode of administration, the formulation used, and the response desired.

In practical use, the peptides as disclosed herein can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, ophthalmic, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or nonaqueous techniques. The amount of active peptide in such therapeutically useful compositions is such that an effective dosage will be obtained. In another advantageous dosage unit form, sublingual constructs may be employed, such as sheets, wafers, tablets or the like. The active peptides can also be administered intranasally as, for example, by liquid drops or spray.

The tablets, pills, capsules, and the like may also contain a binder such as gum tragacanth, acacia, cornstarch, or gelatin; excipients such as dicalcium phosphate; a disintegrating agent such as cornstarch, potato starch, or alginic acid; a lubricant such as magnesium stearate; and a sweetening agent such as sucrose, lactose, or saccharin. When a dosage unit form is a capsule, it may contain, in addition to materials of the above type, a liquid carrier such as a fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl, and propylparabens as preservatives, dyes, and flavorings such as cherry or orange flavor.

Peptides may also be administered parenterally. Solutions or suspensions of these active peptides can be prepared in water suitably mixed with a surfactant such as hydroxypropylcellulose. Dispersions can also be prepared in glycerol, liquid polyethylene glycols and mixtures thereof in oils. These preparations may optionally contain a preservative to prevent the growth of microorganisms.

The pharmaceutical melanocortin analogs suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

Peptides as disclosed herein may be therapeutically applied by means of nasal administration. "Nasal administration" indicates any form of intranasal administration of any of the peptides described herein. The peptides may be in an aqueous solution, such as a solution including saline, citrate or other common excipients or preservatives. The peptides may also be in a dry or powder formulation.

Alternatively, peptides may be administered directly into the lung. Intrapulmonary administration may be performed by means of a metered dose inhaler, a device allowing self-administration of a metered bolus of a peptide when actuated by a patient during inspiration.

The peptides may be formulated with any of a variety of agents that increase effective nasal or ocular absorption of drugs. These agents should increase nasal absorption without unacceptable damage to the mucosal membrane. U.S. Pat. Nos. 5,693,608; 5,977,070; and 5,908,825, among others, teach a number of pharmaceutical compositions that may be employed, and are incorporated by reference for these teachings.

If in an aqueous solution, peptides may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, a suitable preservative may be employed, to prevent or limit bacteria and other microbial growth. One such preservative that may be employed is 0.05% benzalkonium chloride.

It is also possible and contemplated that the peptide may be in a dried and particulate form. For example, the particles can be between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro milling, spray drying and a quick freeze aerosol followed by lyophilization. With microparticles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Exemplary devices include dry powder inhalers, designed to form a cloud or aerosol of fine powder with a particle size that is typically less than about 6.0 µm.

Microparticle size, including mean size distribution, may be controlled by means of the method of making. For micro milling, the size of the milling head, speed of the rotor, time of processing and the like control the microparticle size. For spray drying, the nozzle size, flow rate, dryer heat, and the like control the microparticle size. For making by means of quick freeze aerosol followed by lyophilization, the nozzle size, flow rate, concentration of aerosolized solution and the like control the microparticle size. These parameters and others may be employed to control the microparticle size.

The peptides described herein may be therapeutically administered by means of an injection, typically a deep intramuscular injection, such as in the gluteal or deltoid muscle, of a time-release injectable formulation. A peptide may be formulated with a polyethylene glycol, such as polyethylene glycol 3350, and optionally one or more additional excipients and preservatives, including but not limited to excipients such as salts, polysorbate 80, sodium hydroxide, or hydrochloric acid to adjust pH, and the like. A peptide may also be formulated with a poly(ortho ester), which may be an auto-catalyzed poly(ortho ester) with any of a variable percentage of lactic acid in the polymeric backbone, and optionally one or more additional excipients. A poly(D,L-lactide-co-glycolide) polymer (PLGA polymer) may be employed, such as a PLGA polymer with a hydrophilic end group, such as PLGA RG502H from Boehringer Ingelheim, Inc. (Ingelheim, Germany). Such formulations may be made, for example, by combining a peptide in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which may also be adhesive polymers, may be employed in a time-release injectable formulation. The teachings of U.S. Pat. Nos. 4,938,763, 6,432,438, and 6,673,767, and the biodegradable polymers and methods of formulation disclosed therein, are incorporated here by reference. The formulation may be such that an injection is required on a weekly, monthly, or other periodic basis, depending on the concentration and amount of cyclic peptide, the biodegradation rate of the polymer, and other factors known to those of skill in the art.

Routes of Administration

In various aspects, the melanocortin analogs described herein can be administered using any means known in the art, including orally, rectally, vaginally, ocularly, intranasally, topically, parenterally, or by injection. If administered by injection, the peptide injection may be intravenous (IV), subcutaneous (SC), intramuscular (IM), intraperitoneal (IP), intracerebroventricular (ICV), or other means known in the art. The peptides described herein may be formulated by any means known in the art, including but not limited to formulation as tablets, capsules, caplets, suspensions, powders, lyophilized preparations, suppositories, pessaries, ocular drops, skin patches, orally soluble formulations, enteric formulations, solutions sprays, aerosols and the like, and may be mixed and formulated with buffers, binders, excipients, stabilizers, lubricants, oils, adjuvants, anti-oxidants and other agents known in the art. In general, any route of administration by which the peptides are introduced across an epidermal layer of cells may be employed. Administration includes topical delivery. Administration includes delivery across the blood brain barrier. Administration includes delivery through mucous membranes, buccal administration, ophthalmic administration, oral administration, dermal administration, inhalation administration, nasal administration, urethral administration, vaginal administration, rectal administration, and the like.

Therapeutically Effective Amount

In general, the actual quantity of melanocortin analogs administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a peptide or pharmaceutical composition that is sufficient to therapeutically alleviate feeding disorder in a patient, or to prevent or delay onset or recurrence of the feeding disorder, or for the management of the feeding disorder in patients with diseases or syndromes associated with cachexia, including secondary to immune disorders and cancer.

In general, the melanocortin peptides described herein are highly active. For example, the peptide can be administered at about 0.001 nmol, 0.005 nmol, 0.01 nmol, 0.02 nmol, 0.05 nmol, 0.1 nmol, 0.25 nmol, 0.5 nmol, 1 nmol, 2.5 nmol, 5 nmol, 10 nmol, 20 nmol, 25 nmol, 50 nmol, 100 nmol, 250 nmol, 500 nmol, or 1000 nmol, or even more, depending on the specific peptide selected, the desired therapeutic response, the route of administration, the formulation and other factors known to those of skill in the art.

In some aspects, an effective dose of the peptide is at least about 0.001 nmol, 0.005 nmol, 0.01 nmol, 0.02 nmol, 0.03 nmol, 0.04 nmol, 0.05 nmol, 0.06 nmol, 0.07 nmol, 0.08 nmol, 0.09 nmol, 0.1 nmol, 0.2 nmol, 0.3 nmol, 0.4 nmol, 0.5 nmol, 0.6 nmol, 0.7 nmol, 0.8 nmol, 0.9 nmol, 1.0 nmol, 1.1 nmol, 1.2 nmol, 1.3 nmol, 1.4 nmol, 1.5 nmol, 1.6 nmol, 1.7 nmol, 1.8 nmol, 1.9 nmol, 2 nmol, 3 nmol, 4 nmol, 5 nmol, 6 nmol, 7 nmol, 8 nmol, 9 nmol, 10 nmol, 11 nmol, 12 nmol, 13 nmol, 14 nmol, 15 nmol, 16 nmol, 17 nmol, 18 nmol, 19 nmol, 20 nmol, 21 nmol, 22 nmol, 23 nmol, 24 nmol, 25 nmol, 26 nmol, 27 nmol, 28 nmol, 29 nmol, 30 nmol, 31 nmol, 32 nmol, 33 nmol, 34 nmol, 35 nmol, 36 nmol, 37 nmol, 38 nmol, 39 nmol, 40 nmol, 41 nmol, 42 nmol, 43 nmol, 44 nmol, 45 nmol, 46 nmol, 47 nmol, 48 nmol, 49 nmol, 50 nmol, 51 nmol, 52 nmol, 53 nmol, 54 nmol, 55 nmol, 56 nmol, 57 nmol, 58 nmol, 59 nmol, 60 nmol, 61 nmol, 62 nmol, 63 nmol, 64 nmol, 65 nmol, 66 nmol, 67 nmol, 68 nmol, 69 nmol, 70 nmol, 61 nmol, 72 nmol, 73 nmol, 74 nmol, 75 nmol, 76 nmol, 77 nmol, 78 nmol, 79 nmol, 80 nmol, 81 nmol, 82 nmol, 83 nmol, 84 nmol, 85 nmol, 86 nmol, 87 nmol, 88 nmol, 89 nmol, 90 nmol, 91 nmol, 92 nmol, 93 nmol, 94 nmol, 95 nmol, 96 nmol, 97 nmol, 98 nmol, 99 nmol, 100 nmol, 110 nmol, 120 nmol, 130 nmol, 140 nmol, 150 nmol, 160 nmol, 170 nmol, 180 nmol, 190 nmol, 200 nmol, 210 nmol, 220 nmol, 230 nmol, 240 nmol, 250 nmol, 260 nmol, 270 nmol, 280 nmol, 290 nmol, 300 nmol, 310 nmol, 320 nmol, 330 nmol, 340 nmol, 350 nmol, 360 nmol, 370 nmol, 380 nmol, 390 nmol, 400 nmol, 410 nmol, 420 nmol, 430 nmol, 440 nmol, 450 nmol, 460 nmol, 470 nmol, 480 nmol, 490 nmol, 500 nmol, 510 nmol, 520 nmol, 530 nmol, 540 nmol, 550 nmol, 660 nmol, 770 nmol, 880 nmol, 990 nmol, 600 nmol, 610 nmol, 620 nmol, 630 nmol, 640 nmol, 650 nmol, 660 nmol, 670 nmol, 680 nmol, 690 nmol, 700 nmol, 710 nmol, 720 nmol, 730 nmol, 740 nmol, 750 nmol, 760 nmol, 770 nmol, 780 nmol, 790 nmol, 800 nmol, 810 nmol, 820 nmol, 830 nmol, 840 nmol, 850 nmol, 860 nmol, 870 nmol, 880 nmol, 890 nmol, 900 nmol, 910 nmol, 920 nmol, 930 nmol, 940 nmol, 950 nmol, 960 nmol, 970 nmol, 980 nmol, 990 nmol, 1000 nmol, or in some aspects, even more.

In some aspects an effective dose of the peptide is at least about 0.001 mg, 0.005 mg, 0.1 mg, 0.2 mg, 0.3 mg, 0.4 mg, 0.5 mg, 6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 61 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, 600 mg, 610 mg, 620 mg, 630 mg, 640 mg, 650 mg, 660 mg, 670 mg, 680 mg, 690 mg, 700 mg, 710 mg, 720 mg, 730 mg, 740 mg, 750 mg, 760 mg, 770 mg, 780 mg, 790 mg, 800 mg, 810 mg, 820 mg, 830 mg, 840 mg, 850 mg, 860 mg, 870 mg, 880 mg, 890 mg, 900 mg, 910 mg, 920 mg, 930 mg, 940 mg, 950 mg, 960 mg, 970 mg, 980 mg, 990 mg, 1000 mg, or in some aspects, even more.

In some aspects of the methods described herein, at least one individual dose of the peptide is no more than about 1000 nmol, 990 nmol, 980 nmol, 970 nmol, 960 nmol, 950 nmol, 940 nmol, 930 nmol, 920 nmol, 910 nmol, 900 nmol, 890 nmol, 880 nmol, 870 nmol, 860 nmol, 850 nmol, 840 nmol, 830 nmol, 820 nmol, 810 nmol, 800 nmol, 790 nmol, 780 nmol, 770 nmol, 760 nmol, 750 nmol, 740 nmol, 730 nmol, 720 nmol, 710 nmol, 700 nmol, 690 nmol, 680 nmol, 670 nmol, 660 nmol, 650 nmol, 640 nmol, 630 nmol, 620 nmol, 610 nmol, 600 nmol, 590 nmol, 580 nmol, 570 nmol, 560 nmol, 550 nmol, 540 nmol, 530 nmol, 520 nmol, 510 nmol, 500 nmol, 490 nmol, 480 nmol, 470 nmol, 460 nmol, 450 nmol, 440 nmol, 430 nmol, 420 nmol, 410 nmol, 400 nmol, 390 nmol, 380 nmol, 370 nmol, 360 nmol, 350 nmol, 340 nmol, 330 nmol, 320 nmol, 310 nmol, 300 nmol, 290 nmol, 280 nmol, 270 nmol, 260 nmol, 250 nmol, 240 nmol, 230 nmol, 220 nmol, 210 nmol, 200 nmol, 190 nmol, 180 nmol, 170 nmol, 160 nmol, 150 nmol, 140 nmol, 130 nmol, 120 nmol, 110 nmol, 100 nmol, 99 nmol, 98 nmol, 97 nmol, 96 nmol, 95 nmol, 94 nmol, 93 nmol, 92 nmol, 91 nmol, 90 nmol, 89 nmol, 88 nmol, 87 nmol, 86 nmol, 85 nmol, 84 nmol, 83 nmol, 82 nmol, 81 nmol, 80 nmol, 79 nmol, 78 nmol, 77 nmol, 76 nmol, 75 nmol, 74 nmol, 73 nmol, 72 nmol, 71 nmol, 70 nmol, 69 nmol, 68 nmol, 67 nmol, 66 nmol, 65 nmol, 64 nmol, 63 nmol, 62 nmol, 61 nmol, 60 nmol, 59 nmol, 58 nmol, 57 nmol, 56 nmol, 95 nmol, 54 nmol, 53 nmol, 52 nmol, 51 nmol, 50 nmol, 49 nmol, 48 nmol, 47 nmol, 46 nmol, 45 nmol, 44 nmol, 43 nmol, 42 nmol, 41 nmol, 40 nmol, 39 nmol, 38 nmol, 37 nmol, 36 nmol, 35 nmol, 34 nmol, 33 nmol, 32 nmol, 31 nmol, 30 nmol, 29 nmol, 28 nmol, 27 nmol, 26 nmol, 25 nmol, 24 nmol, 23 nmol, 22 nmol, 21 nmol, 20 nmol, 19 nmol, 18 nmol, 17 nmol, 16 nmol, 15 nmol, 94 nmol, 13 nmol, 12 nmol, 11 nmol, 10 nmol, 9 nmol, 8 nmol, 7 nmol, 6, nmol, 5 nmol, 4 nmol, 3 nmol, 2 nmol, 1 nmol, 0.9 nmol, 0.8 nmol, 0.7 nmol, 0.6 nmol, 0.5 nmol, 0.4 nmol, 0.3 nmol, 0.2 nmol, 0.1 nmol, 0.05 nmol, 0.01 nmol, 0.005 nmol, 0.001 nmol, and even, in some aspects, less than about 0.001 nmol.

In some aspects of the methods described herein, at least one individual dose of the peptide is no more than about 1000 mg, 990 mg, 980 mg, 970 mg, 960 mg, 950 mg, 940 mg, 930 mg, 920 mg, 910 mg, 900 mg, 890 mg, 880 mg, 870 mg, 860 mg, 850 mg, 840 mg, 830 mg, 820 mg, 810 mg, 800 mg, 790 mg, 780 mg, 770 mg, 760 mg, 750 mg, 740 mg, 730 mg, 720 mg, 710 mg, 700 mg, 690 mg, 680 mg, 670 mg, 660 mg, 650 mg, 640 mg, 630 mg, 620 mg, 610 mg, 600 mg, 590 mg, 580 mg, 570 mg, 560 mg, 550 mg, 540 mg, 530 mg, 520 mg, 510 mg, 500 mg, 490 mg, 480 mg, 470 mg, 460 mg, 450 mg, 440 mg, 430 mg, 420 mg, 410 mg, 400 mg, 390 mg, 380 mg, 370 mg, 360 mg, 350 mg, 340 mg, 330 mg, 320 mg, 310 mg, 300 mg, 290 mg, 280 mg, 270 mg, 260 mg, 250 mg, 240 mg, 230 mg, 220 mg, 210 mg, 200 mg, 190 mg, 180 mg, 170 mg, 160 mg, 150 mg, 140 mg, 130 mg, 120 mg, 110 mg, 100 mg, 99 mg, 98 mg, 97 mg, 96 mg, 95 mg, 94 mg, 93 mg, 92 mg, 91 mg, 90 mg, 89 mg, 88 mg, 87 mg, 86 mg, 85 mg, 84 mg, 83 mg, 82 mg, 81 mg, 80 mg, 79 mg, 78 mg, 77 mg, 76 mg, 75 mg, 74 mg, 73 mg, 72 mg, 71 mg, 70 mg, 69 mg, 68 mg, 67 mg, 66 mg, 65 mg, 64 mg, 63 mg, 62 mg, 61 mg, 60 mg, 59 mg, 58 mg, 57 mg, 56 mg, 95 mg, 54 mg, 53 mg, 52 mg, 51 mg, 50 mg, 49 mg, 48 mg, 47 mg, 46 mg, 45 mg, 44 mg, 43 mg, 42 mg, 41 mg, 40 mg, 39 mg, 38 mg, 37 mg, 36 mg, 35 mg, 34 mg, 33 mg, 32 mg, 31 mg, 30 mg, 29 mg, 28 mg, 27 mg, 26 mg, 25 mg, 24 mg, 23 mg, 22 mg, 21 mg, 20 mg, 19 mg, 18 mg, 17 mg, 16 mg, 15 mg, 94 mg, 13 mg, 12 mg, 11 mg, 10 mg, 9 mg, 8 mg, 7 mg, 6, mg, 5 mg, 4 mg, 3 mg, 2 mg, 1 mg, 0.9 mg, 0.8 mg, 0.7 mg, 0.6 mg, 0.5 mg, 0.4 mg, 0.3 mg, 0.2 mg, 0.1 mg, 0.05 mg, 0.01 mg, 0.005 mg, 0.001 mg, and in some aspects, even less.

In some aspects of the methods described herein, an effective dose of the peptide is at least about 0.001 mg/kg body weight to about 10 mg/kg body weight per day.

In some aspects described herein, an effective dose of the peptide is at least about 0.001 mg/kg, 0.005 mg/kg, 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 2.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10.0 mg/kg of body weight per day, or in some aspects, even more.

In some aspects, the peptide is administered by a clinician. In other aspects, the peptide is self-administered. For example, the peptide may be administered in the morning, in the afternoon, or periodically throughout the day. The dose size may be adjusted to account for the frequency and timing of administration of the peptide, and that the daily dosage may, to some degree, be determined by the subject or a clinician based on estimated need, on the delivery system used, and on the presence or absence of other risk factors (e.g., hereditary risk factors or other environmental risk factors such as occupational risk factors and/or exposure to air pollution).

In some aspects, it may be desirable to place an upper limit on single doses and/or daily dosage. Administration devices that limit or modulate self-administration of pulmonary administered pharmaceuticals and other substances in order to prevent possible overdose by the subject are known in the art.

In some aspects of the methods described herein, the peptide may be administered several times a month, several times a week, once each day, or even several times a day. Typically, a therapeutically effective dose is administered once each day. As a non-limiting example, an effective dose may be administered in one or more sessions, such as one portion of a dose is administered in the morning and the remaining portion of a dose is administered in the afternoon.

Dose frequency may be from once daily, twice daily, three times daily, or four times daily, to twice daily, four times daily, six times daily, eight times daily, ten times daily or more than ten times per day. In some aspects, the dose frequency is from once daily to ten times daily, once daily to five times daily, twice daily, or once daily. Frequency of administration may be determined and adjusted over the course of care, and is generally, but not necessarily, based on symptoms and clinical findings.

Inflammation and Immune-Mediated Disorders

The peptides described herein may further be employed in the treatment of inflammation and immune-mediated disorders. See, e.g., Catania A. et al., *Trends Endocrinol. Metab.* 11:304-308 (2000); Gantz and Fong, *Am. J. Physiol. Endocrinol. Metab.* 284: E468-E474 (2003); and Catania et al., *Pharmacol. Rev.* 56:1-29 (2004); each incorporated here by reference.

Combination Therapies

The peptides described herein may be used in combination with other drugs or agents, particularly in the treatment of cachexia. These other drugs and agents may include agents that induce weight gain, including corticosteroids and progestational agents. Peptides may be used in combination with a therapeutically effective amount of a second weight gain pharmaceutical agent.

Methods for the treatment of cachexia are described herein. The methods include the step of administering to the patient having or at risk of having cachexia a therapeutically effective amount of a peptide in combination with a therapeutically effective amount of another compound that is useful in the treatment of cachexia. The second compound useful for the treatment of cachexia are selected from but not limited to the group consisting of ADP-ribose-polymerase inhibitors, ADP-ribose-transferase inhibitors, NADase inhibitors, nicotinamide benzamide, theophylline, thymine and analogs thereof; omega-3 fatty acids such as alpha-linolenic acid, stearidonic acid, eicosapentaenoic acid (EPA), docosapentaenoic acid, docosahexaenoic acid or mixtures thereof; branched-chain amino acids valine, leucine, isoleucine or mixtures thereof, with or without reduced levels of tryptophan and 5-hydroxytryptophan; antioxidants selected from the group comprising beta-carotene, vitamin C, vitamin E, selenium, or mixtures thereof; L-glutamine, vitamin A, vitamin C, vitamin E, and selenium; Azaftig; quinine derivatives including 3,5,6-trimethyl-2-(3-pyridyl) methyl-1,4-benzoquinone hydrochloride; interleukin 2; benzaldehyde; 4,6-O-benzylidene-D-glucose; friedelan-3-one; hydrazine sulfate; medroxyprogesterone acetate; beta 2-adrenoceptor agonists; corticosteroids such as dexamethasone; Vitor™; Pro-Stat™; megestrol acetate (Megace™); dronabinol (Marinol™); magestrol acetate (Megace™); thalidomide (Thalidomid™); fluoxymesterone (Halotestin™); pentoxifylline (Trental™); cyproheptadine (Periactin™); metoclopramide (Reglan™); total parenteral nutrition; or other MC4-R antagonists. A second compound useful for the treatment of cachexia is somatropin (Serostim™), an injectable form of human growth hormone.

The scope of the compositions or methods described herein includes all combinations of aspects, embodiments, examples, and preferences herein described.

EXAMPLES

Example 1

Cardiovascular Activity of Melanocortin Peptides

These studies were performed in urethane-anesthetized rats, since anesthesia is required for six-lead ECG monitoring. Urethane does not appear to affect the melanocortin/RFamide cardiovascular effects that were first reported in conscious rats. Gruber et al., *Hypertension* 6(4):468-74 (1984); Gruber et al., *Am. J. Physiol.* 257(4 Pt 2):R681-694 (1989). Similar cardiovascular effects were found in experimental and clinical studies of melanocortin drugs. Nordheim et al., *Peptides* 27(2):438-443 (2006); Greenfield et al., *N. Engl. J. Med.* 360(1):44-52 (2009). Based on relative dose-effects for melanocortin cardiovascular effects, humans may be significantly more sensitive than rats. Initial selection of doses was guided by FDA exploratory IND studies with a recommendation for at least a 100-fold excess of the human dose.

The melanocortin peptides tested contained various peptides, such as RFamide-like motifs near the C-terminus (e.g., Arg-Trp-Lys; MT-II, PT-141, SHU9119); a multi-residue (2-4 residues) C-terminal amino acid extension that places the Arg-Trp motif deeper within the peptide chain (e.g., MT-I, MT-II, or PT-141); or are peptide mimetics modeled after His-Phe-Arg-Trp (i.e., SHU9119) (see Table 1). Mutulis et al., *J. Med. Chem.* 47(18):4613-4626 (2004).

Peptides, agonists, or antagonists, or a peptide mimetic with an Arg-Trp (like) sequence near the C-terminus ("unprotected" melanocortin peptides) have significant and prolonged pressor activity (Table 2). A striking aspect of unprotected melanocortin peptides is their ability to produce cardiac arrhythmias, both tachycardia and bradycardia. See FIG. 1. Cardiac arrhythmias were reported in the Phase 2 Clinical Trial of a melanocortin drug candidate. See, e.g., Gupta, Palatin, *King Pharma Delay Late-Stage Trial Plans for Drug.* Reuters. Aug. 30, 2007; *King Pharmaceuticals and Palatin Technologies Delay Immediate Plans for Phase 3 Clinical Program with Bremelanotide for Erectile Dysfunstion.* Medical News Today. Aug. 31, 2007; Mishra, *Palatin says King Pharma ends drug agreement on FDA concern.* Reuters. Monday Sep. 10, 2007.

TABLE 1

Structures and Actions of Synthetic Melanocortin Peptides

| Peptide | Structure | Action | SEQ ID NO. |
|---------|-----------|--------|------------|
| MT-I | Ac-Ser-Tyr-Nle-Glu-His-D-Phe-Arg-Trp-Gly-Lys-Pro-Val-NH$_2$ | Agonist | SEQ ID NO: 10 |
| MT-II | Ac-Nle-c[Asp-His-D-Phe-Arg-Trp-Lys]-NH$_2$ | Agonist | SEQ ID NO: 11 |
| PT-141 | Ac-Nle-c[Asp-His-D-Phe-Arg-Trp-Lys]-COOH | Agonist | SEQ ID NO: 12 |
| SHU9119 | Ac-Nle-c[Asp-His-D-Nal(2')-Arg-Trp-Lys]-NH$_2$ | Antagonist | SEQ ID NO: 13 |
| PG932 | Ac-Nle-c[Asp-Pro-D-Nal(2')-Arg-Trp-Lys]-Pro-Val-NH$_2$ | Antagonist | SEQ ID NO: 14 |
| THIQ | N-[(3R)-1,2,3,4-tetrahydroisoquinolinium-3-ylcarbonyl]-(1R)-1-(4-chlorobenzyl)-2-[4-cyclohexyl-4-(1H-1,2,4-triazol-1-ylmethyl)piperidin-1-yl]-2-oxoethylamine | Agonist | — |

Metabolically Stabilized Melanocortin Antagonist

| Peptide | Structure | Action | SEQ ID NO. |
|---------|-----------|--------|------------|
| TCMCB01 | Ac-Nle-c[Asp-Pro-D-Nal(2')-Arg-Trp-Lys]-D-Thr-D-Pro-D-Thr | Antagonist | SEQ ID NO: 15 |
| TCMCB02 | Ac-Nle-c[Asp-Pro-D-Nal(2')-Arg-Trp-Lys]-D-Pro-D-Val-NH$_2$ | Antagonist | SEQ ID NO: 16 |
| TCMCB03 | Ac-Nle-c[Asp-His-D-Nal(2')-Arg-Trp-Lys]-D-Pro-D-Val-NH$_2$ | Antagonist | SEQ ID NO: 17 |
| TCMCB04 | Ac-Nle-c[D-Asp-Pro-D-Nal(2')-Arg-Trp-D-Lys]-D-Pro-D-Val-NH$_2$ | Antagonist | SEQ ID NO: 18 |
| TCMCB05 | Ac-Nle-c[Asp-Pro-D-Nal(2')-Arg-Trp-Lys]-$\beta^3$-Pro-$\beta^2$-Val-NH$_2$ | Antagonist | SEQ ID NO: 19 |
| TCMCB06 | Ac-Nle-c[Asp-Pro-D-Nal(2')-Arg-Trp-Lys]-$\beta^3$-Pro-$\beta^3$-Val-NH$_2$ | Antagonist | SEQ ID NO: 20 |
| TCMCB07 | Ac-Nle-c[Asp-Pro-D-Nal(2')-Arg-Trp-Lys]-D-Val-D-Pro-NH$_2$ | Antagonist | SEQ ID NO: 21 |

TABLE 2

Cardiovascular Effects of Melanocortin Peptides

| Melanocortin Peptide, Dose, n | Peak MAP Response ($\Delta$ mm Hg)/ Peak Heart Rate Response (BPM) | Duration (min) |
|---|---|---|
| MT-I, 250 nmol, n = 5 | 0/0 | 0 |
| MT-II, 250 nmol, n = 5 | 22 ± 5/0 | 42 ± 11 |
| Bremelanotide (PT-141), 250 nmol, n = 5 | 32 ± 6/44 ± 6 | 140 ± 53 |
| SHU-919, 250 nmol, n = 5 | 16 ± 5/3 ± 14 | 29 ± 11 |
| PG-932, 200 nmol, n = 5 | 5 ± 3/13 ± 09 | 4 ± 3 |
| THIQ, 300 nmol, n = 5 | 22 ± 11/81 ± 09 | 19 ± 4 |
| TCMCB01, 600 nmol, n = 5 | 0/0 | 0 |

Example 2

Anti-Cachexia Activity of Metabolically Stabilized Melanocortin Antagonists

The anti-cachectic effects of the first-generation melanocortin antagonist (TCMCB01; SEQ ID NO: 15) were examined in the Lewis sarcoma rat model, and the first-generation (TCMCB01) and second-generation (TCMCB02; SEQ ID NO: 16) melanocortin antagonists in the LPS model of cachexia. Both compounds possessed enhanced anti-cachectic activity (compared to the parent compound, PG932), and no cardiovascular or dose-limiting behavioral side effects typically found in other melanocortin antagonists.

The Lewis model is a methylcholanthrene-induced sarcoma that does not metastasize. This sarcoma is an aggressive form of cancer that produces significant cachexia. Popp et al., Cancer 49(6): 1212-1220 (1982). In the protocol, "treatment" began 8-days after tumor implantation, with a significant decrease in food intake from baseline. Body composition was determined by NMR prior to tumor implantation, and on the final day of the experiment after tumor resection, by ECHO MRI (NMR). Tumor implantation produces cachexia on or about the $6^{th}$ day. Melanocortin drug therapy or saline was begun after day 8 and continued through day 12.

The LPS model uses rats were maintained on a 12 h light/dark schedule with ad libitum access to food and water. Animals were handled daily for a minimum of three consecutive days to decrease non-specific handling stress. On the day of the experiment, individually housed animals received intraperitoneal injections of LPS dissolved in 0.5% low-endotoxin BSA, 0.9% saline or 0.5% BSA in 0.9% saline alone, and were returned to their home cage. The drug or control was administered (ICV, IP, or PO, depending on the type of study) 1-hour after LPS injection.

Example 3

First-Generation Metabolically Stabilized Melanocortin Antagonist: TCMCB01

Figure 2:
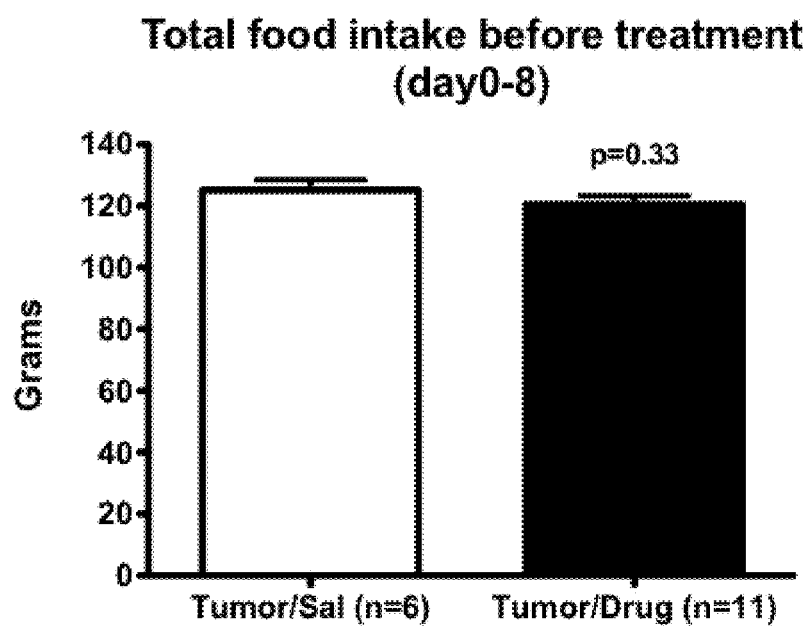
FIG. 2. Food intake in saline control rats and rats in drug treatment groups.
Figure 3:
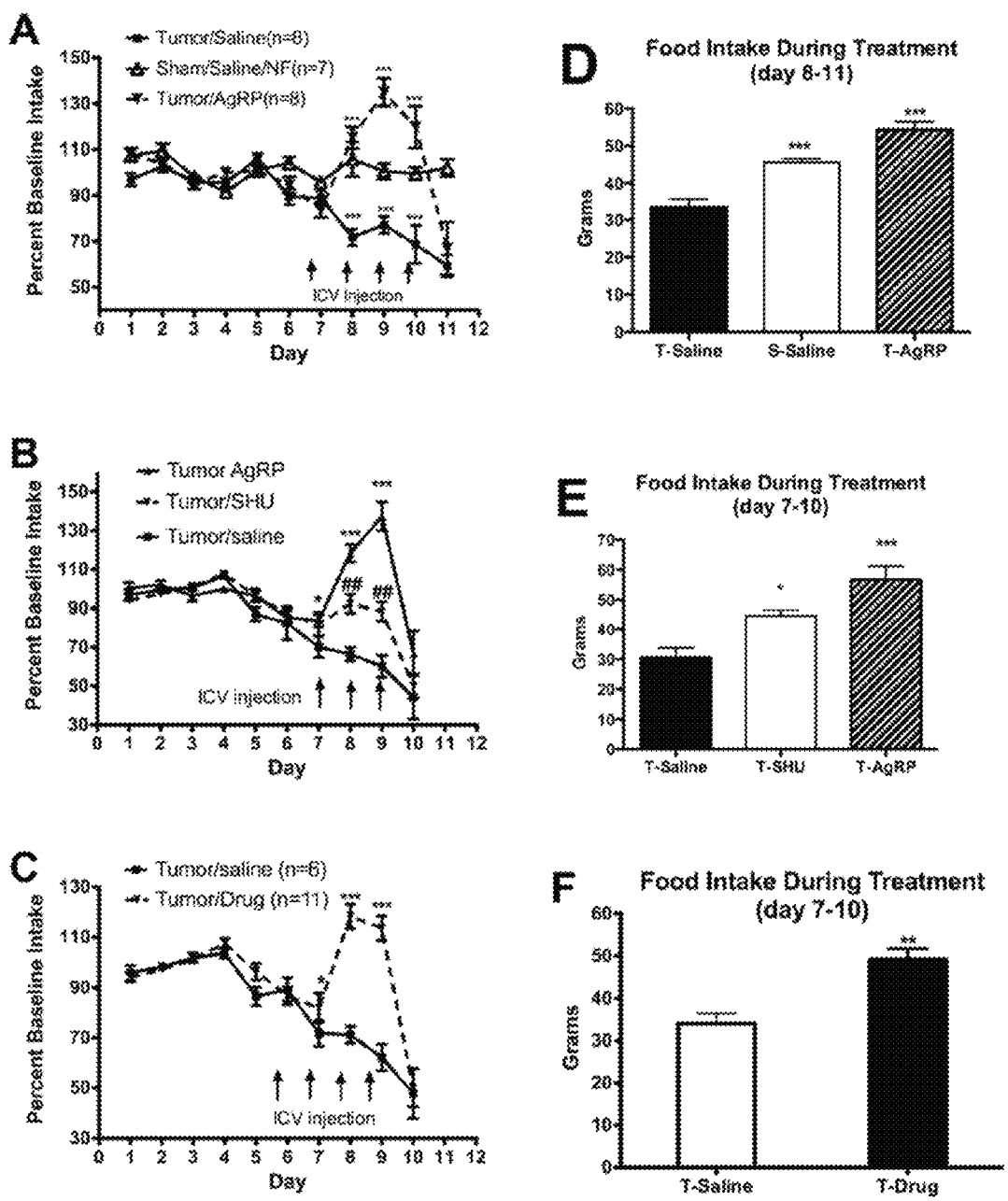
FIG. 3. The inhibition of cancer cachexia by: (i) an endogenous melanocortin system inhibitor (agouti-related protein; AGRP); (ii) SHU9119 (SEQ ID NO: 13); and (iii) TCMCB01 (SEQ ID NO: 15). Panels A-C show the daily food intake of rats bearing a Lewis sarcoma with and without treatment. Panels D-F show total food intake for the treatment period. A sham operation or implantation of tumor cells was on day 1, and significant cancer anorexia was present by days 6-7. The SHU9119-induced reversal of anorexia is about 70% of that observed with AGRP. TCMCB01 produces a significantly greater response, equivalent to AGRP.

Using the Lewis model, treatment with TCMCB01 (see Table 1), one time per day at a dose of 2 nmol, reversed the cachexia-anorexia of the tumor burden, ICV saline had no effect. Prior to tumor implantation, both groups (drug or saline) had similar food intake (~14 g/day). See FIGS. 2A and B. After tumor implantation, in saline-treated/tumor bearing controls, food intake decreased 35% to 9 g/day by day 8. FIGS. 3A-F. However, treatment with TCMCB01 reversed anorexia to a food intake similar to the control state. See FIG. 2B. TCMCB01 was as potent as the natural melanocortin system inhibitor Agouti Related Protein (AGRP), and significantly more potent than SHU9119.

Figure 4:
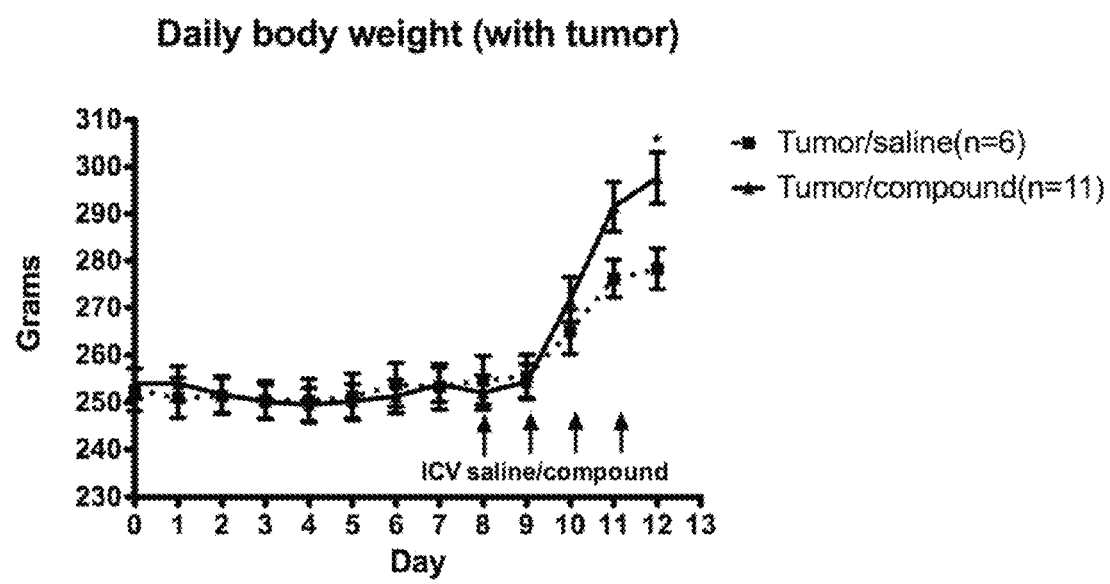
FIG. 4. Body weight of saline control group and TCMCB01-treated rats.
Figure 5:
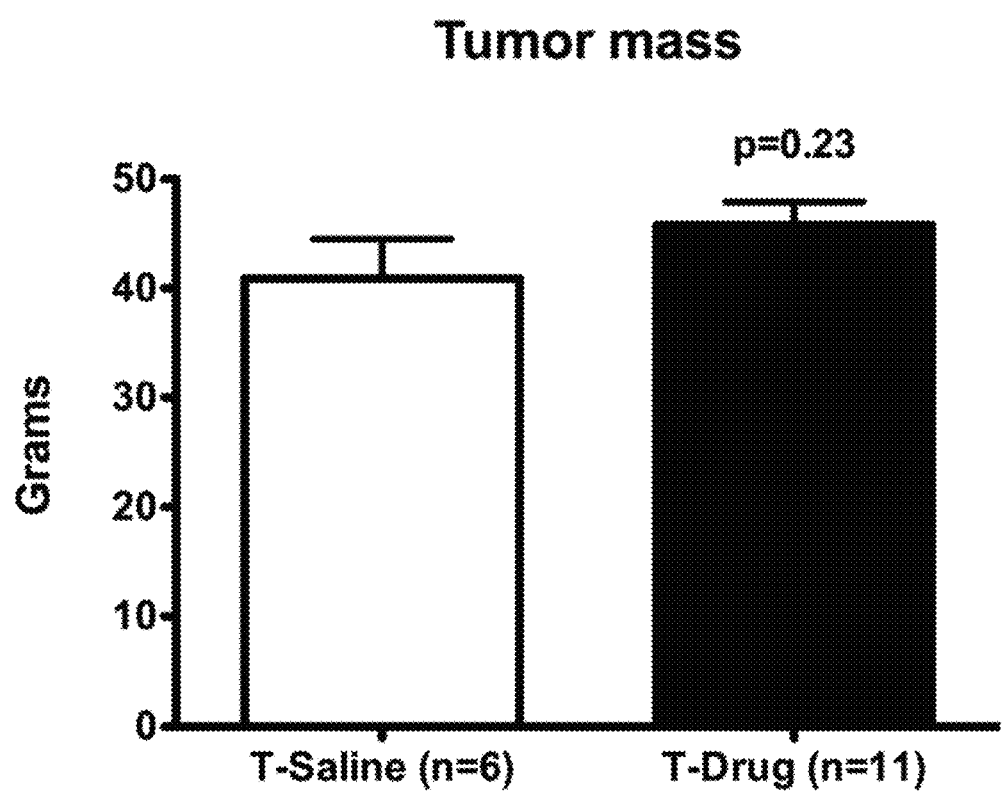
FIG. 5. Tumor weights of saline control and TCMCB01-treated rat groups.
Figure 6:
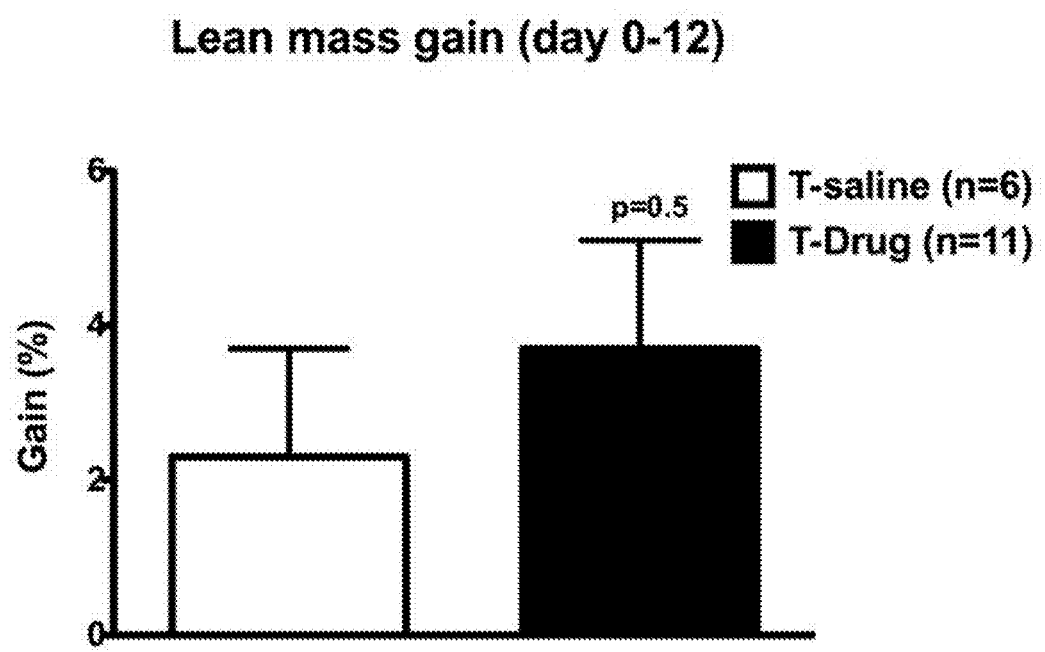
FIG. 6. Lean body mass of saline controls and TCMCB01-treated rat groups

Both groups increased their body weight after tumor implantation, but the drug treated group was significantly greater than saline controls (FIG. 4). In the saline-treated rats, this weight gain was due to the tumor mass. Tumor weight (~40 g) was equivalent in saline-treated and drug-treated group (p=0.2) indicating a food-intake related body weight gain. FIG. 5. While NMR analysis (after tumor excision) showed TCMCB01 treatment increased lean body mass, statistical significance was only p=0.05 (FIG. 6). However, this may be due to the number of NMR observations made (i.e., one pre-treatment and one post-treatment). Food intake and body weight were determined daily. Additional NMR observations or an increased number of observations (i.e., "n") may have resolved this dichotomy.

An important aspect to these results was that previously published results with other synthetic melanocortin antagonists only produced a partial reversal of feeding in cachexia models. The typical result was <50% reversal. The naturally occurring melanocortin antagonist protein, AGRP, produced a 100% reversal of cachexia-anorexia syndrome. Marks et al., Cancer Res. 61(4):1432-1438 (2001). In a related study (not shown), TCMCB01's anti-cachectic effect in the Lewis model was ~20% greater than AGRP, essentially producing hyperphagia. This feeding effect was produced at a dose that was one tenth of that used with previous synthetic melanocortin antagonists. These results suggest that C-terminal "protection" significantly enhanced melanocortin antagonist actions. However, TCMCB01 did not have peripheral activity (assessed in the LPS model). Thus, there was insufficient blood brain barrier-transport for use as a therapeutic agent. The second-generation synthetic melanocortin antagonist, TCMCB02, was then investigated.

Example 4

Second-Generation Stabilized Melanocortin Antagonist: TCMCB02

The second-generation stabilized melanocortin antagonist, TCMCB02 (SEQ ID NO: 16) has the same sequence and cyclization of TCMCB01, (see Table 1), i.e., with the same melanocortin pharmacophore. However, the C-terminal peptide sequence extension is D-Pro-D-Val-NH$_2$. This molecule was designed to combine the blood brain barrier penetrating activity of PG932 with an enzymatically resistant C-terminus. Sutton et al., Peptides 29(1): 104-111 (2008); Marks et al., unpublished data.

Figure 7:
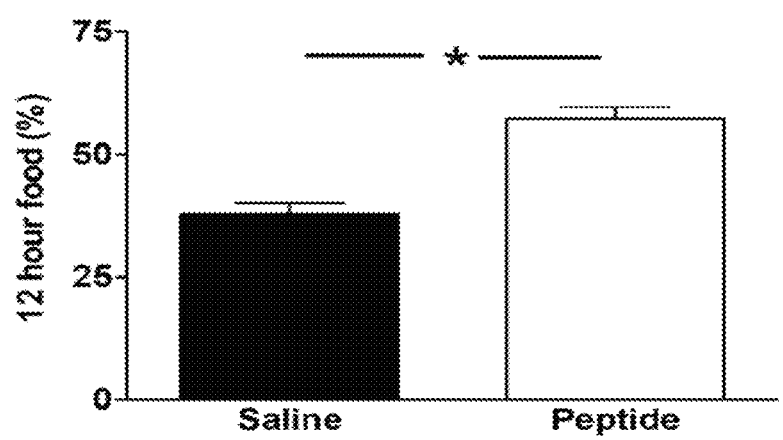
FIG. 7. (A) Data from the second-generation drug candidate, TCMCB02 (SEQ ID NO: 16). TCMCB02 (2 mg/kg, IP) was administered to rats previously injected with lipopolysaccharide (LPS), in an attempt to reverse endotoxin-induced cachexia. Rats primarily eat at night; they lose weight during the day and gain it back at night when they feed. Treatment with TCMCB02 stimulated feeding in a 12-hour overnight assay, compared to a previous 4-day average (baseline). Saline-administered control rats ate 40% of their baseline and TCMCB02-treated rats ate 65%. (B) Saline-treated rats gained little weight overnight, while the TCMCB02-treated rats gained almost 5%. The TCMCB02-treated animals approached a normal weight gain during their baseline period.
Figure 7:
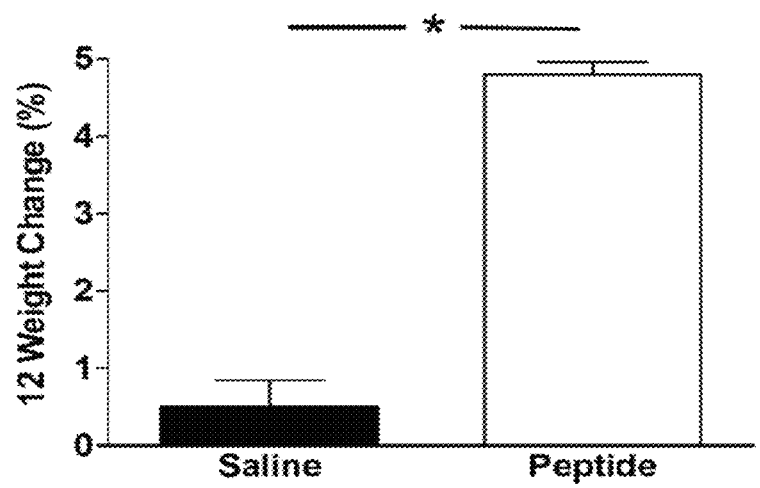

The anti-anorectic activity of TCMCB02 was examined in a two-step process. Using the rat LPS-induced cachexia model, it was confirmed that ICV TCMCB02 maintained direct anti-cachectic activity equivalent to TCMCB01. A peripheral administration study was performed where IP administration of TCMCB02 (2 mg/kg) was given one hour after LPS-administration. The subsequent 12-hour feeding data is shown in FIGS. 7A-B, and the effects on body weight in FIG. 8. These data indicate that TCMCB02 has peripheral activity, significantly reversing LPS-induced cachexia.

Data from several other cyclic melanocortin peptides suggests that blood brain barrier transport and oral activity appear to co-exist. See, e.g., Hess et al., J. Med. Chem. 50(24):6201-6211 (2007); Hess et al., J. Med. Chem. 51(4): 1026-1034 (2008). Because TCMCB02 has 10-fold greater anti-cachectic activity than the "parent" compound (TCMCB01), it appears that the D-amino acid C-terminal dipeptide provides chronic protection. This enhances therapeutic efficacy and prevents expression of any over-lapping pharmacophore side effects. Thus, two melanocortin antagonists with D-amino acids and di- or tri-peptide C-termini showed enhanced efficacy, and no cardiovascular or behavioral side effects. However, as is discussed below, TCMCB02 did not have oral activity; i.e., a lack of trans-gastro-intestinal epithelial transport.

Example 5

Basis for Trans-Epithelial Transport of Peptide Drugs

Active transport carriers for di- and tri-peptides have been described, and these transported peptides can serve as carriers for small cyclic peptides or non-peptide drugs. Brandsch, *Amino Acids* 31(2): 119-136 (2006); Brandsch et al., *J. Pharm. Pharmacol.* 60(5): 543-58 (2008). For example, the peptide transporters PEPT1 and PEPT2 are known to mediate di- and tri-peptide (oligopeptide) transport respectively through the gastrointestinal tract and the blood-brain-barrier (ependymal cells and choroid plexus). However, there has never been a detailed description of the requirements that allow an oligopeptide transport system to carry attached drugs across the gastrointestinal barrier or the blood brain barrier, or an approach that allows the transport of drugs greater than 500-600 Daltons. A detailed examination of the structural requirements of di- and tri-peptides that can be linked to molecules for active transport, and whether small changes in peptide structure are important for overall molecule transport had not been conducted previously. Furthermore, different molecules may function better with regards transport having specific peptides added to their C- or N-terminus, and a peptide sequence that works well as a transporter at one terminus may not work at the other.

Example 6

Third-Generation Melanocortin Antagonist: TCMCB03 (i.e., His$^6$ PG932)

Initial comparisons of the two best-characterized melanocortin antagonists, SHU9119 and PG932, could conclude that PG932 was active peripherally, while SHU9119 was not (see Table 1). Sutton et al., *Peptides* 29(1): 104-111 (2008). This question of whether a His$^6$ (SHU9119) or Pro$^6$ (PG932) in the pharmacophore produces a superior anti-cachectic effect went unanswered. TCMCB03 (SEQ ID NO: 17) has a His$^6$ (see Table 1). A comparison of TCMCB02 (Pro$^6$) and TCMCB03 (His$^6$) showed that the His-for-Pro substitution enhanced anti-cachexia when given ICV in the LPS experimental model. However, in an IP administration study, TCMCB03 failed to cross the blood brain barrier.

Using Pro, an imidic acid, rather than an amino acid as one of the residues in a cyclic peptide reduces free rotation: a secondary amine forms one of the peptide bonds of the Pro residue. Reducing free rotation is an important factor in cyclic peptide active transport through epithelial barriers. Hess et al., *J. Med. Chem.* 50(24): 6201-6211 (2007). Results herein confirm this hypothesis. In addition, the sequence of the di-peptide extension of the cyclic structure is also important (see the fifth- and seventh-generation polypeptides, below). Collectively, these data are consistent with a oligopeptide transport system functioning as the drug/cyclic peptide carrier, as previously described. Vabeno et al., *Bioorg. Med. Chem.* 13(6): 1977-1988 (2005); Kikuchi et al., *J. Pharm. Sci.* 98(5): 1775-1787 (2009); Wang et al., *J. Biomed. Sci.* 17: 71 (2010).

Example 7

Fourth-Generation Melanocortin Antagonist: TCMCB04 (i.e., D-Asp$^5$, D-Lys$^{10}$ TCMCB02)

The historical basis for cyclizing MCs. was that a reverse turn conformation was required for receptor binding. Sawyer et al., *Proc. Nat. Acad. Sci. USA* 79(6): 1751-1755 (1982); Sawyer et al., *J. Med. Chem.* 25(9): 1022-1027 (1982). Initially, a D-amino acid substitution in the middle of the melanocortin pharmacophore enhanced biological activity: presumably because a D-residue will reduce the tendency of an L-amino acid sequence to form an α-helix, but stabilize a β-turn. Sawyer et al., *Proc. Nat. Acad. Sci. USA* 77(10): 5754-5758 (1980).

Cyclized melanocortins were the next historical step; first di-sulfide bridging was utilized, then lactam bridges were used. It was thought that using D-amino acid residues to form the lactam bridge in cyclic melanocortins would further stabilize the cyclic structure, producing superior biological activity. TCMCB04 (SEQ ID NO: 18), the D-Asp$^5$, D-Lys$^{10}$ derivative of TCMCB02, a drug candidate with blood brain barrier transport properties was synthesized (see Table 1). Given ICV, this polypeptide had superior anti-cachectic activity compared to the parent compound in the LPS assay. However, the D-Asp$^5$, D-Lys$^{10}$ modification eliminated blood brain barrier transport, demonstrating that both blood brain barrier (this polypeptide) and GI transport (TCMCB02) depend on the stereospecificity of the derivative.

The role of polypeptide structure in peptide active transport by the di- or tri-peptide transport systems has not been thoroughly investigated. Results herein show that slight chemical and/or stereochemical changes in polypeptide structure has significant effects on the transport properties of the drug-peptide transporter complex. Several important factors were identified that promote melanocortin-di-peptide achieve transport.

Example 8

Role of Dipeptide Structure in Drug-Dipeptide Complex Transport; Fifth- and Sixth-Generation Melanocortin Antagonists: TCMCB05 and TCMCB06

Figure 8:
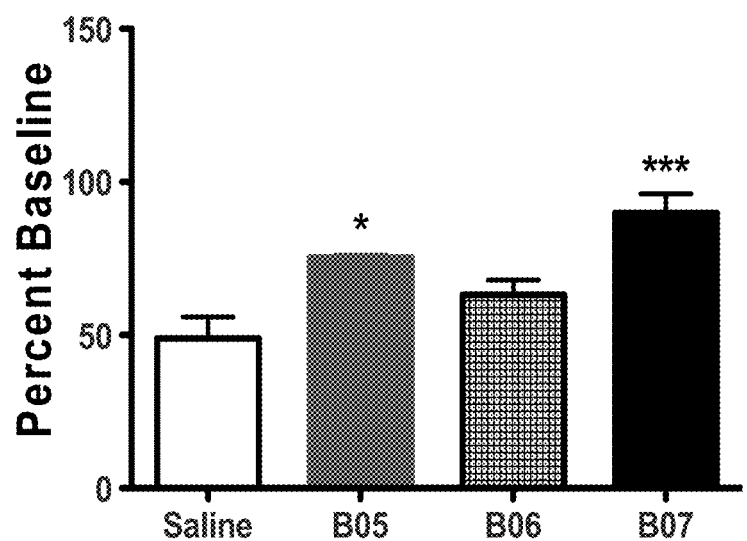
FIG. 8. The effect of a LPS injection in rats, immediately before a dark cycle, on (A) food intake and (B) body weight (as percent of pre-LPS baseline). Measurements were made for 24-hours following the challenge, and drug candidates were given intraperitoneally at 0.2 mg/kg. The saline-treated control rats were anorexic and lost weight. Rats treated with TCMCB05 (SEQ ID NO: 19) and TCMCB07 (SEQ ID NO: 21) had stimulated appetites and significantly gained weight. The TCMCB06 (SEQ ID NO: 20)-treated rat ate significantly less food than the other drug candidates, and had no weight gain. While the weight gain in rats treated with TCMCB05 or TCMCB07 appear less than that observed with TCMCB01 (see FIG. 5B), the TCMCB05 and TCMCB07 data were recorded at the end of the 12 hour dark cycle when eating occurred. These data are 24 hour data, including the dark/feeding phase and the subsequent 12 hours of light cycle, when weight loss occurs. *p<0.05, ***p<0.001
Figure 8:
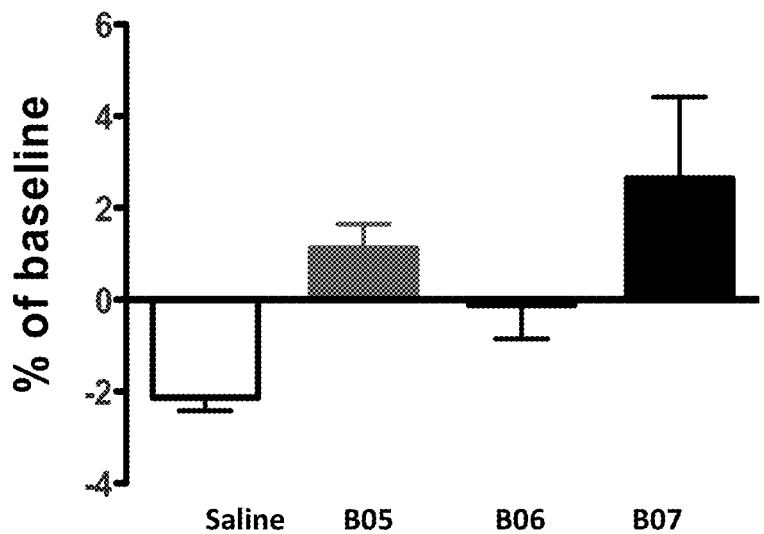
Figure 9:
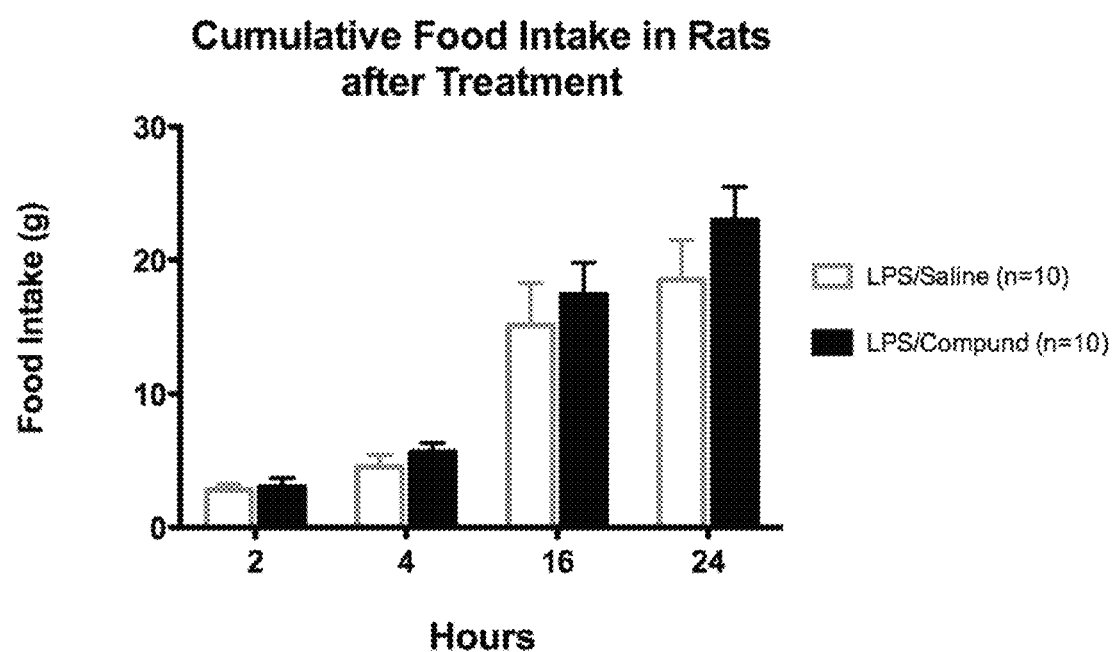
FIG. 9. The effects of peripherally administered TCMCB04 ("compound") on food intake in a bacterial toxin-(LPS)-induced model of cachexia. No difference was observed between the peptide and saline (i.e., no transport across the blood-brain barrier), even though the C-terminal di-peptide is the same as TCMCB02, which had peripheral LPS-anti-cachexia activity. Thus, changing two residues in the "load" from L- to D-amino acids blocked blood-brain barrier transport; transport is stereospecific, effectively eliminating paracellular movement through the blood-brain barrier as the TCMCB02 mechanism of action. The stereospecificity is inconsistent with a movement governed by the "Rule of Five" (Lipinski et al., *Adv. Drug Deliv. Rev.* 46(1-3): 3-26 (2001).
Figure 10:
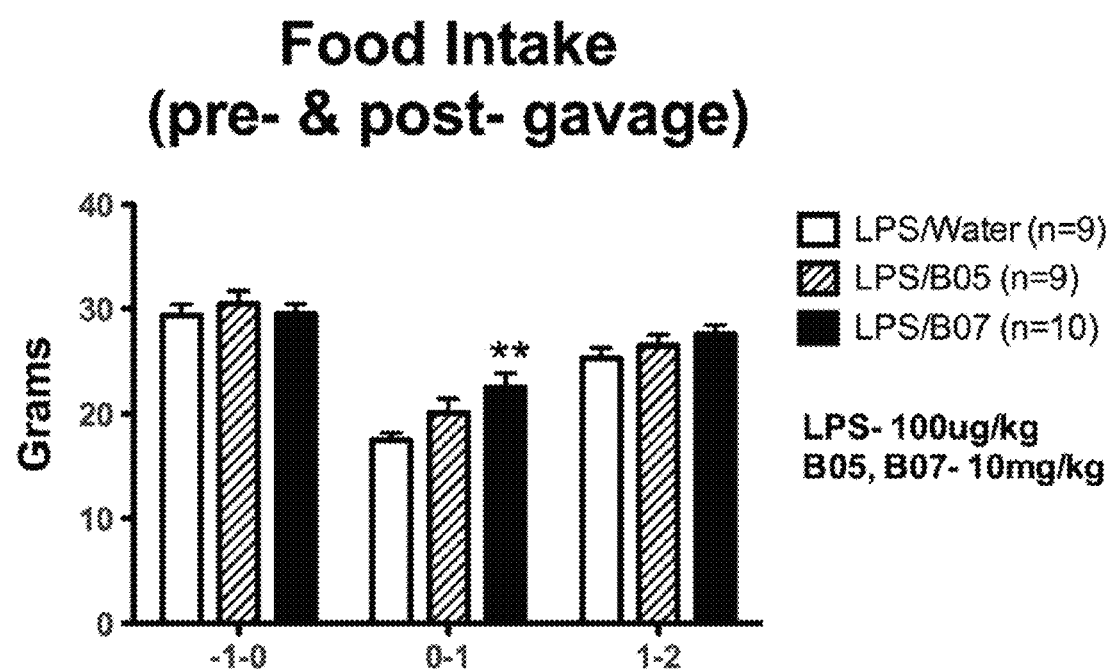
FIG. 10. A comparison of the peripheral activity of TCMCB05 and TCMCB07 on food intake during LPS-induced cachexia. TCMB05 (Ac-Nle-c[Asp-Pro-D-Nal(2'-Arg-Trp-Lys]-$β^3$-Pro-$β^2$-Val-$NH_2$), differs from TCMB07 by having a β-Pro-β-Val C-terminal extention, whereas TCMB07 has the reversed C-terminal extension with D-amino acids (Ac-Nle-c[Asp-Pro-D-Nal(2')-Arg-Trp-Lys]-D-Val-D-Pro-$NH_2$). Only TCMCB07 produced a significant increase in feeding.
Figure 11:
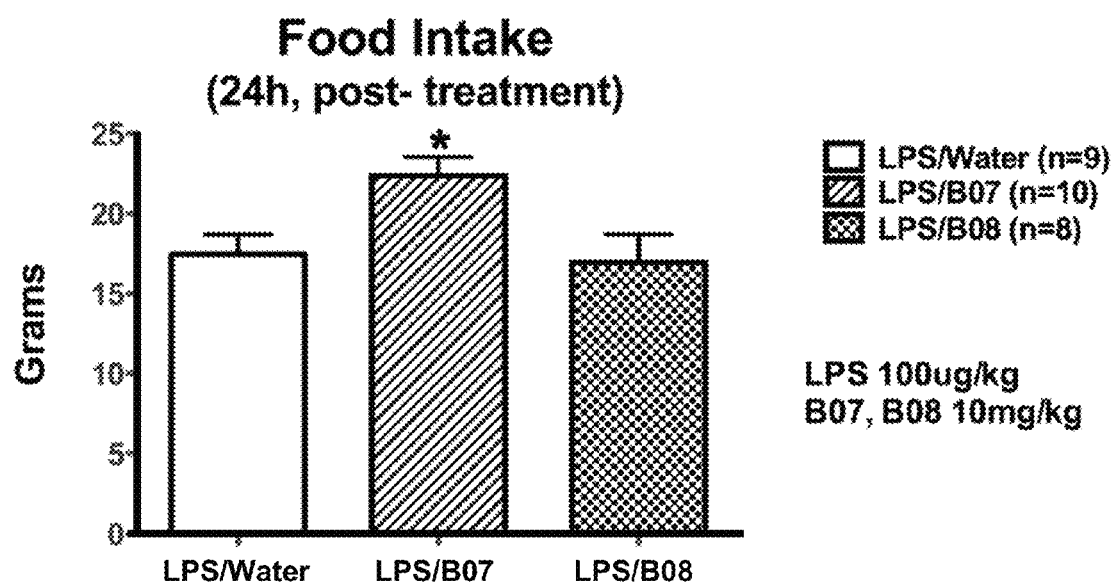
FIG. 11. A comparison of TCMCB07 and TCMCB08 effects on feeding following gavage (intra-gastric) administration in LPS cachexia. These data demonstrate that a C-terminal Val-Pro sequence (Ac-Nle-c[Asp-Pro-D-Nal(2')-Arg-Trp-Lys]-D-Val-D-Pro-$NH_2$; TCMCB07) composed of D-residues imparts oral activity to the drug molecule and causes a significant enhancement of food intake. The same di-peptide sequence composed of β-residues does not (e.g., Ac-Nle-c[Asp-Pro-D-Nal(2')-Arg-Trp-Lys]-$β^2$-Val-$β^3$-Pro-$NH_2$; TCMCB08). Two conclusions can be drawn about the structure required for oral activity. First, a TCMCB02 vs. TCMCB07 comparison shows that oral activity is di-peptide sequence specific: Pro-Val only has blood-brain barrier transport; Val-Pro has both gastrointestinal and blood-brain barrier transport. Second, TCMCB08 has peripheral activity (data not shown) but no gastrointestinal transport. Thus, oral activity is dependent on the movement of the α-carbon amino and/or carboxyl groups (of the di-peptide) to the β-carbon. The blood-brain barrier oligopeptide transporter accepts a particular β-residue di-peptide, while the gastrointestinal oligopeptide transporter does not.
Figure 12:
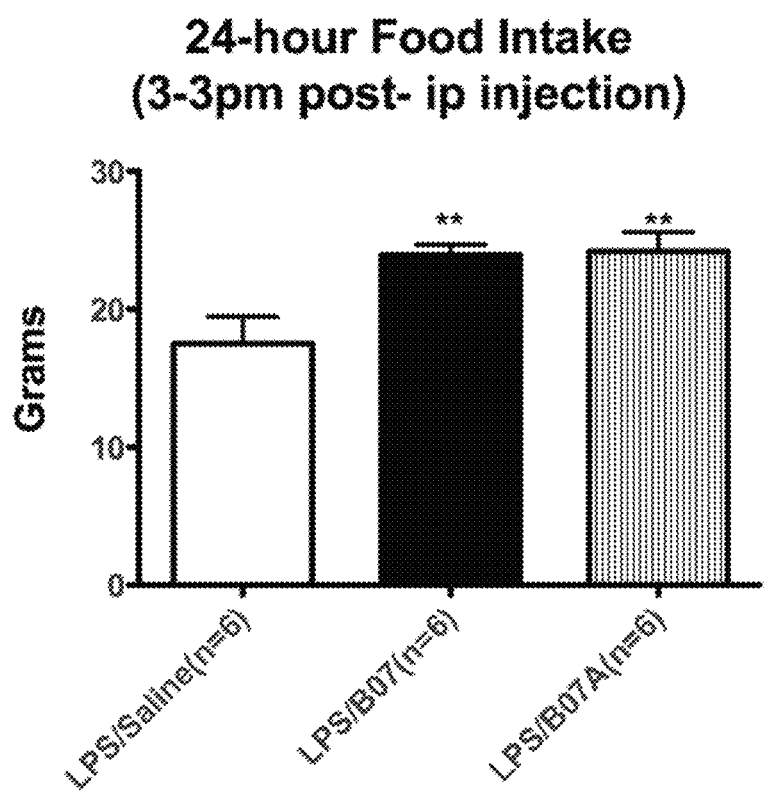
FIG. 12. Peripheral administration of TCMCB07 and TCMCB 07A. TCMCB07 and TCMCB07A have the same primary peptide sequence except that TCMCB07 has a C-terminal amide moiety and TCMCB07A does not, i.e., Ac-Nle-c[Asp-Pro-D-Nal(2')-Arg-Trp-Lys]-D-Val-D-Pro-$NH_2$ (TCMCB07) vs. Ac-Nle-c[Asp-Pro-D-Nal(2')-Arg-Trp-Lys]-D-Val-D-Pro-OH (TCMCB07A). Peripheral administration of TCMCB07 or TCMCB07A produces equivalent stimulation of feeding in LPS-induced cachexia. Thus, the C-terminal amide moiety has no effect on transport but may stabilize the peptide against degradation.

The TCMCB05 (i.e., β$^3$-Pro$^{11}$, β$^2$-Val$^{12}$; SEQ ID NO: 19) and TCMCB06 (i.e., β$^3$-Pro$^{11}$, β$^3$-Val$^{12}$; SEQ ID NO: 20) polypeptides were designed to combine the stereochemistry of L-amino acids with the resistance to enzymatic degradation of D-residues (see Table 1). Amino or imidic acids with their D-amino and/or carboxyl groups displaced by a β-carbon maintain their side-chain stereochemistry and are more stable to enzymatic degradation. Lew et al., *FASEB J.* 15(9): 1664-1666 (2001); Nachman et al., *Peptides* 30(3): 608-615 (2009). Both TCMCB05 and TCMCB06 had 10-fold greater molar activity than TCMCB02 in LPS-induced cachexia following ICV-administration. However, only TCMCB05 (β$^3$-Pro-β$^2$-Val) had IP anti-cachexia activity as measured by enhancing food intake and weight gain following LPS-administration. This result provided further evidence for peptide transport independent of the "Rule of Five" (FIGS. 8 A-B). Lipinski et al., *Adv. Drug Deliv. Rev.* 46(1-3): 3-26 (2001).

Example 9

Seventh-Generation Melanocortin Antagonists: TCMCB07 (i.e., D-Val$^{11}$, D-Pro$^{12}$TCMCB02)

TCMCB07 (SEQ ID NO: 21) is based on TCMCB02 with the C-terminal di-peptide sequence of TCMCB02 reversed see Table 1). This analog was designed to test the sequence specificity for transport. This polypeptide maintained ICV activity. However, it had 10-fold more peripheral (IP) LPS anti-cachectic activity than TCMCB02, suggesting that the C-terminal sequence affected specific blood brain barrier transport (FIGS. 8 A-B). This result providing additional evidence for peptide transport independent of the "Rule of Five" effect, and supported the possibility of a specific transporter.

Example 10

Summary of TCMCB05-TCMCB07 Antagonists

An important aspect of C- or N-terminal stabilization is in the residue selection process. Variables include the stereochemistry of the residue (e.g., D- or L-conformation); the chemical moieties of the side chain; and which carbon atom (α-, β-, γ-, etc.) the amino- or carboxyl-groups are attached to. For example, the melanocortin antagonist PG932 has a C-terminal di-peptide sequence of Pro-Val-amide. This C-terminal extension is not part of the cyclized melanocortin pharmacophore of the molecule. Thus, the extension does not play a role in receptor binding or activation. Changing these two residues (Pro-Val) to the D-configuration increases in vivo stability and/or apparent efficacy by 10-fold, as assessed by the dose required to alleviate bacterial toxin-induced cachexia in rats following intracerebroventricular (ICV) administration. This effect is not mediated by an apparent effect in receptor interaction, but rather stability against enzymatic degradation. The TCMCB01 sequence with a C-terminal D-configuration dipeptide has blood-brain barrier transport. An additional 10-fold reduction in the (ICV) dose required for bacterial toxin anti-cachexia is produced by changing the D-configuration C-terminal di-peptide to β-Pro-β-Val-amide (both residues in the L-configuration). Thus, L-amino acid residues of the β-type are more stabilizing to the C-terminus of a peptide than their equivalent (side-chain group) α-types in the D-configuration.

Example 11

Reversal of Cachexia-Induced Lethargy

In animals and humans, cachexia produces "lethargy," i.e., the aversion to activity. Grossberg et al., *J. Neurosci.* 31(31): 11376-11386. Once-daily peripheral dosing with TCMCB02, TCMCB05, or TCMCB07 (see Table 1) for 48 hours (i.e., 2 IP doses) restored "normal" behavior to rats, irrespective of tumor load. This therapeutic effect is dependent on a stabilized melanocortin antagonist C-terminal extension. Video recordings characterized control animal behavior as neo-exploratory movement about the cage, i.e., repeated "sniffing" the air to presumably sample odors (e.g., neighboring animals), grooming, and intermittent bouts of eating and drinking. Caldecott-Hazard et al., *J. Neurosci.* 8(6): 1951-1961 (1988).

In contrast, a Lewis sarcoma rat exhibits no neo-exploratory behavior. The animal typically remains in one position for an extended period of time (>1 minute). Occasionally it will change position, assuming the new position for an extended period. The rats show no grooming behavior, evident in the appearance of their coat and eyes. Food intake is greatly reduced.

The restoration of normal behavior following treatment with the polypeptides is independent of food intake. Lethargy is not produced by the reduction in caloric intake, nor reversed solely by increased food intake. A recent study describes the non-melanocortin basis for cachexia-induced lethargy. Grossberg et al., *J. Neurosci.* 31(31): 11376-11386. Based on this, TCMCB01-TCMCB07 are thought to activate the orexin system. However, it should be appreciated that merely having an automated recording of movement does not reveal the qualitative aspects of what is occurring physiologically. As an illustrative example, restoring appetite (melanocortin drug therapy) to a cachectic animal will cause it to seek food. When the animal is provided food, it will sit near the food hopper and eat (reduced movement). If an animal is not provided food, it may move around the cage seeking food (increased movement).

Example 12

Melanocortin 3- and 4-Receptor Antagonists

Melanocortin 3 and 4 Receptor antagonists are useful for treating disorders of impaired appetite and lean body mass wasting. See Table 3. This includes cachexia-anorexia syndrome, anorexia nervosa, dermatomyositis, polymyositis, muscular dystrophy, sarcopenia, and other muscle mass wasting syndromes.

Melanocortin antagonists are also useful as regulators of the delta (δ) opioid system. They have direct agonist at the delta opioid receptor, indirect opioid agonist actions through inhibition of the central melanocortin system. These effects enhance the exogenous opioid actions, and prevent development of exogenous opioid tolerance. Thus, melanocortin antagonists may be useful alone or in combination with opioid analogs.

In addition, melanocortin antagonists are melanocortin 5 receptor agonists. Thus, they are potentially useful for treating syndromes of decreased/impaired exocrine gland secretion; for example dry and/or dry mouth. These latter disorders are characterized by a relative lack of lacrimal gland (eye) and/or salivary gland secretions. Table 3 contains a list of melanocortin 3- and 4-receptor antagonists and melanocortin 5 receptor agonists useful as described herein.

TABLE 3

Melanocortin 3- and 4-Receptor Antagonists and Melanocortin 5 Receptor Agonists

| | | |
|---|---|---|
| TCMCB345 1 | Ac-Nle-c[Asp-Pro-D-Nal(2')-Arg-Trp-Lys]-D-Thr-D-Pro-D-Thr | SEQ ID NO: 22 |
| TCMCB345 2 | Ac-Nle-c[Asp-His-D-Nal(2')-Arg-Trp-Lys]-D-Thr-D-Pro-D-Thr | SEQ ID NO: 23 |
| TCMCB345 3 | Ac-Nle-c[D-Asp-Pro-D-Nal(2')-Arg-Trp-D-Lys]-D-Thr-D-Pro-D-Thr | SEQ ID NO: 24 |
| TCMCB345 4 | Ac-Nle-c[Asp-His-D-Nal(2')-Arg-Trp-D-Lys]-D-Thr-D-Pro-D-Thr | SEQ ID NO: 25 |
| TCMCB345 5 | Ac-Nle-c[Asp-Pro-D-Nal(2')-Arg-Trp-Lys]-D-Pro-D-Val-$NH_2$ | SEQ ID NO: 26 |
| TCMCB345 6 | Ac-Nle-c[Asp-His-D-Nal(2')-Arg-Trp-Lys]-D-Pro-D-Val-$NH_2$ | SEQ ID NO: 27 |
| TCMCB345 7 | Ac-Nle-c[D-Asp-Pro-D-Nal(2')-Arg-Trp-D-Lys]-D-Pro-D-Val-$NH_2$ | SEQ ID NO: 28 |

TABLE 3-continued

Melanocortin 3- and 4-Receptor Antagonists and Melanocortin 5 Receptor Agonists

| | | |
|---|---|---|
| TCMCB345 8 | Ac-Nle-c[D-Asp-His-D-Nal(2')-Arg-Trp-D-Lys]-D-Pro-D-Val-NH$_2$ | SEQ ID NO: 29 |
| TCMCB345 9 | Ac-Nle-c[Asp-Pro-D-Nal(2')-Arg-Trp-Lys]-D-Val-D-Pro-NH$_2$ | SEQ ID NO: 30 |
| TCMCB345 10 | Ac-Nle-c[Asp-His-D-Nal(2')-Arg-Trp-Lys]-D-Val-D-Pro-NH$_2$ | SEQ ID NO: 31 |
| TCMCB345 11 | Ac-Nle-c[D-Asp-Pro-D-Nal(2')-Arg-Trp-D-Lys]-D-Val-D-Pro-NH$_2$ | SEQ ID NO: 32 |
| TCMCB345 12 | Ac-Nle-c[D-Asp-His-D-Nal(2')-Arg-Trp-D-Lys]-D-Val-D-Pro-NH$_2$ | SEQ ID NO: 33 |
| TCMCB345 13 | Ac-Nle-c[Asp-Pro-D-Nal(2')-Arg-Trp-Lys]-β-Pro-β-Val-NH$_2$ | SEQ ID NO: 34 |
| TCMCB345 14 | Ac-Nle-c[Asp-His-D-Nal(2')-Arg-Trp-Lys]-β-Pro-β-Val-NH$_2$ | SEQ ID NO: 35 |
| TCMCB345 15 | Ac-Nle-c[D-Asp-Pro-D-Nal(2')-Arg-Trp-D-Lys]-β-Pro-β-Val-NH$_2$ | SEQ ID NO: 36 |
| TCMCB345 16 | Ac-Nle-c[D-Asp-His-D-Nal(2')-Arg-Trp-D-Lys]-β-Pro-β-Val-NH$_2$ | SEQ ID NO: 37 |
| TCMCB345 17 | Ac-Nle-c[Asp-Pro-D-Nal(2')-Arg-Trp-Lys]-β-Val-β-Pro-NH$_2$ | SEQ ID NO: 38 |
| TCMCB345 18 | Ac-Nle-c[Asp-His-D-Nal(2')-Arg-Trp-Lys]-β-Val-β-Pro-NH$_2$ | SEQ ID NO: 39 |
| TCMCB345 19 | Ac-Nle-c[D-Asp-Pro-D-Nal(2')-Arg-Trp-D-Lys]-β-Val-β-Pro-NH$_2$ | SEQ ID NO: 40 |
| TCMCB345 20 | Ac-Nle-c[D-Asp-His-D-Nal(2')-Arg-Trp-D-Lys]-β-Val-β-Pro-NH$_2$ | SEQ ID NO: 41 |
| TCMCB345 21 | Ac-Nle-c[Asp-Pro-D-Nal(2')-Arg-Trp-Lys]-β-Pro-β-Pro-NH$_2$ | SEQ ID NO: 42 |
| TCMCB345 22 | Ac-Nle-c[Asp-His-D-Nal(2')-Arg-Trp-Lys]-β-Pro-β-Pro-NH$_2$ | SEQ ID NO: 43 |
| TCMCB345 23 | Ac-Nle-c[D-Asp-Pro-D-Nal(2')-Arg-Trp-D-Lys]-β-Pro-β-Pro-NH$_2$ | SEQ ID NO: 44 |
| TCMCB345 24 | Ac-Nle-c[D-Asp-His-D-Nal(2')-Arg-Trp-D-Lys]-β-Pro-β-Pro-NH$_2$ | SEQ ID NO: 45 |
| TCMCB345 25 | Ac-Nle-c[Asp-Pro-D-Nal(2')-Arg-Trp-Lys]-β-Val-β-Val-NH$_2$ | SEQ ID NO: 46 |
| TCMCB345 26 | Ac-Nle-c[Asp-His-D-Nal(2')-Arg-Trp-Lys]-β-Val-β-Val-NH$_2$ | SEQ ID NO: 47 |
| TCMCB345 27 | Ac-Nle-c[D-Asp-Pro-D-Nal(2')-Arg-Trp-D-Lys]-β-Val-β-Val-NH$_2$ | SEQ ID NO: 48 |
| TCMCB345 28 | Ac-Nle-c[D-Asp-His-D-Nal(2')-Arg-Trp-D-Lys]-β-Val-β-Val-NH$_2$ | SEQ ID NO: 49 |
| TCMCB345 29 | Ac-Nle-c[Asp-Pro-D-Nal(2')-Arg-Trp-Lys]-(3-methyl)-β-Val-β-Val-NH$_2$ | SEQ ID NO: 50 |
| TCMCB345 30 | Ac-Nle-c[Asp-His-D-Nal(2')-Arg-Trp-Lys]-(3-methyl)-β-Val-β-Val-NH$_2$ | SEQ ID NO: 51 |
| TCMCB345 31 | Ac-Nle-c[D-Asp-Pro-D-Nal(2')-Arg-Trp-D-Lys]-(3-methyl)-β-Val-β-Val-NH$_2$ | SEQ ID NO: 52 |
| TCMCB345 32 | Ac-Nle-c[D-Asp-His-D-Nal(2')-Arg-Trp-D-Lys]-(3-methyl)-β-Val-β-Val-NH$_2$ | SEQ ID NO: 53 |
| TCMCB345 33 | Ac-Nle-c[Asp-Pro-D-Nal(2')-Arg-Trp-Lys]-(3-methyl)-β-Val-β-Pro-NH$_2$ | SEQ ID NO: 54 |
| TCMCB345 34 | Ac-Nle-c[Asp-His-D-Nal(2')-Arg-Trp-Lys]-(3-methyl)-β-Val-β-Pro-NH$_2$ | SEQ ID NO: 55 |
| TCMCB345 35 | Ac-Nle-c[D-Asp-Pro-D-Nal(2')-Arg-Trp-D-Lys]-(3-methyl)-β-Val-β-Pro-NH$_2$ | SEQ ID NO: 56 |
| TCMCB345 36 | Ac-Nle-c[D-Asp-His-D-Nal(2')-Arg-Trp-D-Lys]-(3-methyl)-β-Val-β-Pro-NH$_2$ | SEQ ID NO: 57 |
| TCMCB345 37 | Ac-Nle-c[Asp-Pro-D-Nal(2')-Arg-Trp-Lys]-β-Thr-β-Pro-β-Thr | SEQ ID NO: 58 |
| TCMCB345 38 | Ac-Nle-c[Asp-His-D-Nal(2')-Arg-Trp-Lys]-β-Thr-β-Pro-β-Thr | SEQ ID NO: 59 |
| TCMCB345 39 | Ac-Nle-c[D-Asp-Pro-D-Nal(2')-Arg-Trp-D-Lys]-β-Thr-β-Pro-β-Thr | SEQ ID NO: 60 |
| TCMCB345 40 | Ac-Nle-c[D-Asp-His-D-Nal(2')-Arg-Trp-D-Lys]-β-Thr-β-Pro-β-Thr | SEQ ID NO: 61 |
| TCMCB345 41 | Ac-Nle-c[Asp-Pro-D-Nal(2')-Arg-Trp-Lys]-D-Pro-D-Ala-NH$_2$ | SEQ ID NO: 62 |
| TCMCB345 42 | Ac-Nle-c[Asp-His-D-Nal(2')-Arg-Trp-Lys]-D-Pro-D-Ala-NH$_2$ | SEQ ID NO: 63 |
| TCMCB345 43 | Ac-Nle-c[D-Asp-Pro-D-Nal(2')-Arg-Trp-D-Lys]-D-Pro-D-Ala-NH$_2$ | SEQ ID NO: 64 |
| TCMCB345 44 | Ac-Nle-c[Asp-His-D-Nal(2')-Arg-Trp-Lys]-D-Pro-D-Ala-NH$_2$ | SEQ ID NO: 65 |

TABLE 3-continued

Melanocortin 3- and 4-Receptor Antagonists and Melanocortin 5 Receptor Agonists

| | | |
|---|---|---|
| TCMCB345 45 | Ac-Nle-c[Asp-Pro-D-Nal(2')-Arg-Trp-Lys]-D-Ala-D-Pro-NH$_2$ | SEQ ID NO: 66 |
| TCMCB345 46 | Ac-Nle-c[Asp-His-D-Nal(2')-Arg-Trp-Lys]-D-Ala-D-Pro-NH$_2$ | SEQ ID NO: 67 |
| TCMCB345 47 | Ac-Nle-c[D-Asp-Pro-D-Nal(2')-Arg-Trp-D-Lys]-D-Ala-D-Pro-NH$_2$ | SEQ ID NO: 68 |
| TCMCB345 48 | Ac-Nle-c[D-Asp-His-D-Nal(2')-Arg-Trp-D-Lys]-D-Ala-D-Pro-NH$_2$ | SEQ ID NO: 69 |
| TCMCB345 49 | Ac-Nle-c[Asp-Pro-D-Nal(2')-Arg-Trp-Lys]-β-Pro-β-Ala-NH$_2$ | SEQ ID NO: 70 |
| TCMCB345 50 | Ac-Nle-c[Asp-His-D-Nal(2')-Arg-Trp-Lys]-β-Pro-β-Ala-NH$_2$ | SEQ ID NO: 71 |
| TCMCB345 51 | Ac-Nle-c[D-Asp-Pro-D-Nal(2')-Arg-Trp-D-Lys]-β-Pro-β-Ala-NH$_2$ | SEQ ID NO: 72 |
| TCMCB345 52 | Ac-Nle-c[D-Asp-His-D-Nal(2')-Arg-Trp-D-Lys]-β-Pro-β-Ala-NH$_2$ | SEQ ID NO: 73 |
| TCMCB345 53 | Ac-Nle-c[Asp-Pro-D-Nal(2')-Arg-Trp-Lys]-β-Ala-β-Pro-NH$_2$ | SEQ ID NO: 74 |
| TCMCB345 54 | Ac-Nle-c[Asp-His-D-Nal(2')-Arg-Trp-Lys]-β-Ala-β-Pro-NH$_2$ | SEQ ID NO: 75 |
| TCMCB345 55 | Ac-Nle-c[D-Asp-Pro-D-Nal(2')-Arg-Trp-D-Lys]-β-Ala-β-Pro-NH$_2$ | SEQ ID NO: 76 |
| TCMCB345 56 | Ac-Nle-c[D-Asp-His-D-Nal(2')-Arg-Trp-D-Lys]-β-Ala-β-Pro-NH$_2$ | SEQ ID NO: 77 |
| TCMCB345 57 | Ac-Nle-c[Asp-Pro-D-Nal(2')-Arg-Trp-Lys]-β-Val-β-Ala-NH$_2$ | SEQ ID NO: 78 |
| TCMCB345 58 | Ac-Nle-c[Asp-His-D-Nal(2')-Arg-Trp-Lys]-β-Val-β-Ala-NH$_2$ | SEQ ID NO: 79 |
| TCMCB345 59 | Ac-Nle-c[D-Asp-Pro-D-Nal(2')-Arg-Trp-D-Lys]-β-Val-β-Ala-NH$_2$ | SEQ ID NO: 80 |
| TCMCB345 60 | Ac-Nle-c[D-Asp-His-D-Nal(2')-Arg-Trp-D-Lys]-β-Val-β-Ala-NH$_2$ | SEQ ID NO: 81 |
| TCMCB345 61 | Ac-Nle-c[Asp-Pro-D-Nal(2')-Arg-Trp-Lys]-(3-methyl)-β-Val-β-Ala-NH$_2$ | SEQ ID NO: 82 |
| TCMCB345 62 | Ac-Nle-c[Asp-His-D-Nal(2')-Arg-Trp-Lys]-(3-methyl)-β-Val-β-Ala-NH$_2$ | SEQ ID NO: 83 |
| TCMCB345 63 | Ac-Nle-c[D-Asp-Pro-D-Nal(2')-Arg-Trp-D-Lys]-(3-methyl)-β-Val-β-Ala-NH$_2$ | SEQ ID NO: 84 |
| TCMCB345 64 | Ac-Nle-c[D-Asp-His-D-Nal(2')-Arg-Trp-D-Lys]-(3-methyl)-β-Val-β-Ala-NH$_2$ | SEQ ID NO: 85 |
| TCMCB345 65 | Ac-Nle-c[Asp-Pro-D-Nal(2')-Arg-Trp-Lys]-D-Pro-D-Leu-NH$_2$ | SEQ ID NO: 86 |
| TCMCB345 66 | Ac-Nle-c[Asp-His-D-Nal(2')-Arg-Trp-Lys]-D-Pro-D-Leu-NH$_2$ | SEQ ID NO: 87 |
| TCMCB345 67 | Ac-Nle-c[D-Asp-Pro-D-Nal(2')-Arg-Trp-Lys]-D-Pro-D-Leu-NH$_2$ | SEQ ID NO: 88 |
| TCMCB345 68 | Ac-Nle-c[Asp-His-D-Nal(2')-Arg-Trp-Lys]-D-Pro-D-Leu-NH$_2$ | SEQ ID NO: 89 |
| TCMCB345 69 | Ac-Nle-c[Asp-Pro-D-Nal(2')-Arg-Trp-Lys]-D-Leu-D-Pro-NH$_2$ | SEQ ID NO: 90 |
| TCMCB345 70 | Ac-Nle-c[Asp-His-D-Nal(2')-Arg-Trp-Lys]-D-Leu-D-Pro-NH$_2$ | SEQ ID NO: 91 |
| TCMCB345 71 | Ac-Nle-c[D-Asp-Pro-D-Nal(2')-Arg-Trp-D-Lys]-D-Leu-D-Pro-NH$_2$ | SEQ ID NO: 92 |
| TCMCB345 72 | Ac-Nle-c[D-Asp-His-D-Nal(2')-Arg-Trp-D-Lys]-D-Leu-D-Pro-NH$_2$ | SEQ ID NO: 93 |
| TCMCB345 73 | Ac-Nle-c[Asp-Pro-D-Nal(2')-Arg-Trp-Lys]-β-Pro-β-Leu-NH$_2$ | SEQ ID NO: 94 |
| TCMCB345 74 | Ac-Nle-c[Asp-His-D-Nal(2')-Arg-Trp-Lys]-β-Pro-β-Leu-NH$_2$ | SEQ ID NO: 95 |
| TCMCB345 75 | Ac-Nle-c[D-Asp-Pro-D-Nal(2')-Arg-Trp-D-Lys]-β-Pro-β-Leu-NH$_2$ | SEQ ID NO: 96 |
| TCMCB345 76 | Ac-Nle-c[D-Asp-His-D-Nal(2')-Arg-Trp-D-Lys]-β-Pro-β-Leu-NH$_2$ | SEQ ID NO: 97 |
| TCMCB345 77 | Ac-Nle-c[Asp-Pro-D-Nal(2')-Arg-Trp-Lys]-β-Leu-β-Pro-NH$_2$ | SEQ ID NO: 98 |
| TCMCB345 78 | Ac-Nle-c[Asp-His-D-Nal(2')-Arg-Trp-Lys]-β-Leu-β-Pro-NH$_2$ | SEQ ID NO: 99 |
| TCMCB345 79 | Ac-Nle-c[D-Asp-Pro-D-Nal(2')-Arg-Trp-D-Lys]-β-Leu-β-Pro-NH$_2$ | SEQ ID NO: 100 |
| TCMCB345 80 | Ac-Nle-c[D-Asp-His-D-Nal(2')-Arg-Trp-D-Lys]-β-Leu-β-Pro-NH$_2$ | SEQ ID NO: 101 |
| TCMCB345 81 | Ac-Nle-c[Asp-Pro-D-Nal(2')-Arg-Trp-Lys]-β-Val-β-Leu-NH$_2$ | SEQ ID NO: 102 |
| TCMCB345 82 | Ac-Nle-c[Asp-His-D-Nal(2')-Arg-Trp-Lys]-β-Val-β-Leu-NH$_2$ | SEQ ID NO: 103 |

TABLE 3-continued

Melanocortin 3- and 4-Receptor Antagonists and Melanocortin 5 Receptor Agonists

| | | |
|---|---|---|
| TCMCB345 83 | Ac-Nle-c[D-Asp-Pro-D-Nal(2')-Arg-Trp-D-Lys]-β-Val-β-Leu-NH$_2$ | SEQ ID NO: 104 |
| TCMCB345 84 | Ac-Nle-c[D-Asp-His-D-Nal(2')-Arg-Trp-D-Lys]-β-Val-β-Leu-NH$_2$ | SEQ ID NO: 105 |
| TCMCB345 85 | Ac-Nle-c[Asp-Pro-D-Nal(2')-Arg-Trp-Lys]-(3-methyl)-β-Val-β-Leu-NH$_2$ | SEQ ID NO: 106 |
| TCMCB345 86 | Ac-Nle-c[Asp-His-D-Nal(2')-Arg-Trp-Lys]-(3-methyl)-β-Val-β-Leu-NH$_2$ | SEQ ID NO: 107 |
| TCMCB345 87 | Ac-Nle-c[D-Asp-Pro-D-Nal(2')-Arg-Trp-D-Lys]-(3-methyl)-β-Val-β-Leu-NH$_2$ | SEQ ID NO: 108 |
| TCMCB345 88 | Ac-Nle-c[D-Asp-His-D-Nal(2')-Arg-Trp-D-Lys]-(3-methyl)-β-Val-β-Leu-NH$_2$ | SEQ ID NO: 109 |

Example 13

Melanocortin 3- and 4-Receptor Agonists

Melanocortin receptor agonists are potent inhibitors of feeding/appetite and stimulate metabolism. See Table 4. These actions have been shown to be useful in diseases or conditions producing excess body weight, since melanocortin agonist treatment contributes to weight loss. Table 4 contains a list of melanocortin 3- and 4-receptor agonists useful as described herein.

TABLE 4

Melanocortin 3- and 4-Receptor Agonists

| | | |
|---|---|---|
| TCMCA34 1 | Ac-Nle-c[Asp-Pro-D-Phe-Arg-Trp-Lys]-D-Thr-D-Pro-D-Thr | SEQ ID NO: 110 |
| TCMCA34 2 | Ac-Nle-c[Asp-His-D-Phe-Arg-Trp-Lys]-D-Thr-D-Pro-D-Thr | SEQ ID NO: 111 |
| TCMCA34 3 | Ac-Nle-c[D-Asp-Pro-D-Phe-Arg-Trp-D-Lys]-D-Thr-D-Pro-D-Thr | SEQ ID NO: 112 |
| TCMCA34 4 | Ac-Nle-c[D-Asp-His-D-Phe-Arg-Trp-D-Lys]-D-Thr-D-Pro-D-Thr | SEQ ID NO: 113 |
| TCMCA34 5 | Ac-Nle-c[Asp-Pro-D-Phe-Arg-Trp-Lys]-D-Pro-D-Val-NH$_2$ | SEQ ID NO: 114 |
| TCMCA34 6 | Ac-Nle-c[Asp-His-D-Phe-Arg-Trp-Lys]-D-Pro-D-Val-NH$_2$ | SEQ ID NO: 115 |
| TCMCA34 7 | Ac-Nle-c[D-Asp-Pro-D-Nal(2')-Arg-Trp-D-Lys]-D-Pro-D-Val-NH$_2$ | SEQ ID NO: 116 |
| TCMCA34 8 | Ac-Nle-c[Asp-His-D-Nal(2')-Arg-Trp-Lys]-D-Pro-D-Val-NH$_2$ | SEQ ID NO: 117 |
| TCMCA34 9 | Ac-Nle-c[Asp-Pro-D-Phe-Arg-Trp-Lys]-D-Val-D-Pro-NH$_2$ | SEQ ID NO: 118 |
| TCMCA34 10 | Ac-Nle-c[Asp-His-D-Phe-Arg-Trp-Lys]-D-Val-D-Pro-NH$_2$ | SEQ ID NO: 119 |
| TCMCA34 11 | Ac-Nle-c[D-Asp-Pro-D-Phe-Arg-Trp-D-Lys]-D-Val-D-Pro-NH$_2$ | SEQ ID NO: 120 |
| TCMCA34 12 | Ac-Nle-c[D-Asp-His-D-Nal(2')-Arg-Trp-D-Lys]-D-Val-D-Pro-NH$_2$ | SEQ ID NO: 121 |
| TCMCA34 13 | Ac-Nle-c[Asp-Pro-D-Phe-Arg-Trp-Lys]-β-Pro-β-Val-NH$_2$ | SEQ ID NO: 122 |
| TCMCA34 14 | Ac-Nle-c[Asp-His-D-Phe-Arg-Trp-Lys]-β-Pro-β-Val-NH$_2$ | SEQ ID NO: 123 |
| TCMCA34 15 | Ac-Nle-c[D-Asp-Pro-D-Phe-Arg-Trp-D-Lys]-β-Pro-β-Val-NH$_2$ | SEQ ID NO: 124 |
| TCMCA34 16 | Ac-Nle-c[D-Asp-His-D-Phe-Arg-Trp-D-Lys]-β-Pro-β-Val-NH$_2$ | SEQ ID NO: 125 |
| TCMCA34 17 | Ac-Nle-c[Asp-Pro-D-Phe-Arg-Trp-Lys]-β-Val-β-Pro-NH$_2$ | SEQ ID NO: 126 |
| TCMCA34 18 | Ac-Nle-c[Asp-His-D-Phe-Arg-Trp-Lys]-β-Val-β-Pro-NH$_2$ | SEQ ID NO: 127 |
| TCMCA34 19 | Ac-Nle-c[D-Asp-Pro-D-Phe-Arg-Trp-D-Lys]-β-Val-β-Pro-NH$_2$ | SEQ ID NO: 128 |
| TCMCA34 20 | Ac-Nle-c[D-Asp-His-D-Nal(2')-Arg-Trp-D-Lys]-β-Val-β-Pro-NH$_2$ | SEQ ID NO: 129 |
| TCMCA34 21 | Ac-Nle-c[Asp-Pro-D-Phe-Arg-Trp-Lys]-β-Pro-β-Pro-NH$_2$ | SEQ ID NO: 130 |
| TCMCA34 22 | Ac-Nle-c[Asp-His-D-Phe-Arg-Trp-Lys]-β-Pro-β-Pro-NH$_2$ | SEQ ID NO: 131 |
| TCMCA34 23 | Ac-Nle-c[D-Asp-Pro-D-Nal(2')-Arg-Trp-D-Lys]-β-Pro-β-Pro-NH$_2$ | SEQ ID NO: 132 |
| TCMCA34 24 | Ac-Nle-c[D-Asp-His-D-Nal(2')-Arg-Trp-D-Lys]-β-Pro-β-Pro-NH$_2$ | SEQ ID NO: 133 |

TABLE 4-continued

Melanocortin 3- and 4-Receptor Agonists

| TCMCA34 25 | Ac-Nle-c[Asp-Pro-D-Phe-Arg-Trp-Lys]-β-Val-β-Val-NH$_2$ | SEQ ID NO: 134 |
| --- | --- | --- |
| TCMCA34 26 | Ac-Nle-c[Asp-His-D-Phe-Arg-Trp-Lys]-β-Val-β-Val-NH$_2$ | SEQ ID NO: 135 |
| TCMCA34 27 | Ac-Nle-c[D-Asp-Pro-Phe-Arg-Trp-D-Lys]-β-Val-β-Val-NH$_2$ | SEQ ID NO: 136 |
| TCMCA34 28 | Ac-Nle-c[D-Asp-His-D-Phe-Arg-Trp-D-Lys]-β-Val-β-Val-NH$_2$ | SEQ ID NO: 137 |
| TCMCA34 29 | Ac-Nle-c[Asp-Pro-D-Phe-Arg-Trp-Lys]-(3-methyl)-β-Val-β-Val-NH$_2$ | SEQ ID NO: 138 |
| TCMCA34 30 | Ac-Nle-c[Asp-His-D-Phe-Arg-Trp-Lys]-(3-methyl)-β-Val-β-Val-NH$_2$ | SEQ ID NO: 139 |
| TCMCA34 31 | Ac-Nle-c[D-Asp-Pro-D-Phe-Arg-Trp-D-Lys]-(3-methyl)-β-Val-β-Val-NH$_2$ | SEQ ID NO: 140 |
| TCMCA34 32 | Ac-Nle-c[D-Asp-His-D-Phe-Arg-Trp-D-Lys]-(3-methyl)-β-Val-β-Val-NH$_2$ | SEQ ID NO: 141 |
| TCMCA34 33 | Ac-Nle-c[Asp-Pro-D-Phe-Arg-Trp-Lys]-(3-methyl)-β-Val-β-Pro-NH$_2$ | SEQ ID NO: 142 |
| TCMCA34 34 | Ac-Nle-c[Asp-His-D-Phe-Arg-Trp-Lys]-(3-methyl)-β-Val-β-Pro-NH$_2$ | SEQ ID NO: 143 |
| TCMCA34 35 | Ac-Nle-c[D-Asp-Pro-D-Phe-Arg-Trp-D-Lys]-(3-methyl)-β-Val-β-Pro-NH$_2$ | SEQ ID NO: 144 |
| TCMCA34 36 | Ac-Nle-c[D-Asp-His-D-Phe-Arg-Trp-D-Lys]-(3-methyl)-β-Val-β-Pro-NH$_2$ | SEQ ID NO: 145 |
| TCMCA34 37 | Ac-Nle-c[Asp-Pro-D-Phe-Arg-Trp-Lys]-β-Thr-β-Pro-β-Thr | SEQ ID NO: 146 |
| TCMCA34 38 | Ac-Nle-c[Asp-His-D-Phe-Arg-Trp-Lys]-β-Thr-β-Pro-β-Thr | SEQ ID NO: 147 |
| TCMCA34 39 | Ac-Nle-c[D-Asp-Pro-D-Phe-Arg-Trp-D-Lys]-β-Thr-β-Pro-β-Thr | SEQ ID NO: 148 |
| TCMCA34 40 | Ac-Nle-c[D-Asp-His-D-Phe-Arg-Trp-D-Lys]-β-Thr-β-Pro-β-Thr | SEQ ID NO: 149 |
| TCMCA34 41 | Ac-Nle-c[Asp-Pro-D-Phe-Arg-Trp-Lys]-D-Pro-D-Ala-NH$_2$ | SEQ ID NO: 150 |
| TCMCA34 42 | Ac-Nle-c[Asp-His-D-Phe-Arg-Trp-Lys]-D-Pro-D-Ala-NH$_2$ | SEQ ID NO: 151 |
| TCMCA34 43 | Ac-Nle-c[D-Asp-Pro-D-Phe-Arg-Trp-D-Lys]-D-Pro-D-Ala-NH$_2$ | SEQ ID NO: 152 |
| TCMCA34 44 | Ac-Nle-c[Asp-His-D-Phe-Arg-Trp-Lys]-D-Pro-D-Ala-NH$_2$ | SEQ ID NO: 153 |
| TCMCA34 45 | Ac-Nle-c[Asp-Pro-D-Phe-Arg-Trp-Lys]-D-Ala-D-Pro-NH$_2$ | SEQ ID NO: 154 |
| TCMCA34 46 | Ac-Nle-c[Asp-His-D-Phe-Arg-Trp-Lys]-D-Ala-D-Pro-NH$_2$ | SEQ ID NO: 155 |
| TCMCA34 47 | Ac-Nle-c[D-Asp-Pro-D-Phe-Arg-Trp-D-Lys]D-Ala-D-Pro-NH$_2$ | SEQ ID NO: 156 |
| TCMCA34 48 | Ac-Nle-c[D-Asp-His-D-Phe-Arg-Trp-D-Lys]-D-Ala-D-Pro-NH$_2$ | SEQ ID NO: 157 |
| TCMCA34 49 | Ac-Nle-c[Asp-Pro-D-Phe-Arg-Trp-Lys]-β-Pro-β-Ala-NH$_2$ | SEQ ID NO: 158 |
| TCMCA34 50 | Ac-Nle-c[Asp-His-D-Phe-Arg-Trp-Lys]-β-Pro-β-Ala-NH$_2$ | SEQ ID NO: 159 |
| TCMCA34 51 | Ac-Nle-c[D-Asp-Pro-D-Phe-Arg-Trp-D-Lys]-β-Pro-β-Ala-NH$_2$ | SEQ ID NO: 160 |
| TCMCA34 52 | Ac-Nle-c[D-Asp-His-D-Phe-Arg-Trp-D-Lys]-β-Pro-β-Ala-NH$_2$ | SEQ ID NO: 161 |
| TCMCA34 53 | Ac-Nle-c[Asp-Pro-D-Phe-Arg-Trp-Lys]-β-Ala-β-Pro-NH$_2$ | SEQ ID NO: 162 |
| TCMCA34 54 | Ac-Nle-c[Asp-His-D-Phe-Arg-Trp-Lys]-β-Ala-β-Pro-NH$_2$ | SEQ ID NO: 163 |
| TCMCA34 55 | Ac-Nle-c[D-Asp-Pro-D-Phe-Arg-Trp-D-Lys]-β-Ala-β-Pro-NH$_2$ | SEQ ID NO: 164 |
| TCMCA34 56 | Ac-Nle-c[D-Asp-His-D-Phe-Arg-Trp-D-Lys]-β-Ala-β-Pro-NH$_2$ | SEQ ID NO: 165 |
| TCMCA34 57 | Ac-Nle-c[Asp-Pro-D-Phe-Arg-Trp-Lys]-β-Val-β-Ala-NH$_2$ | SEQ ID NO: 166 |
| TCMCA34 58 | Ac-Nle-c[Asp-His-D-Phe-Arg-Trp-Lys]-β-Val-β-Ala-NH$_2$ | SEQ ID NO: 167 |
| TCMCA34 59 | Ac-Nle-c[D-Asp-Pro-D-Phe-Arg-Trp-D-Lys]-β-Val-β-Ala-NH$_2$ | SEQ ID NO: 168 |
| TCMCA34 60 | Ac-Nle-c[D-Asp-His-D-Nal(2')-Arg-Trp-D-Lys]-β-Val-β-Ala-NH$_2$ | SEQ ID NO: 169 |
| TCMCA34 61 | Ac-Nle-c[Asp-Pro-D-Phe-Arg-Trp-Lys]-(3-methyl)-β-Val-β-Ala-NH$_2$ | SEQ ID NO: 170 |
| TCMCA34 62 | Ac-Nle-c[Asp-His-D-Phe-Arg-Trp-Lys]-(3-methyl)-β-Val-β-Ala-NH$_2$ | SEQ ID NO: 171 |
| TCMCA34 63 | Ac-Nle-c[D-Asp-Pro-D-Phe-Arg-Trp-D-Lys]-(3-methyl)-β-Val-β-Ala-NH$_2$ | SEQ ID NO: 172 |

TABLE 4-continued

Melanocortin 3- and 4-Receptor Agonists

| | | |
|---|---|---|
| TCMCA34 64 | Ac-Nle-c[D-Asp-His-D-Phe-Arg-Trp-D-Lys]-(3-methyl)-β-Val-β-Ala-NH$_2$ | SEQ ID NO: 173 |
| TCMCA34 65 | Ac-Nle-c[Asp-Pro-D-Phe-Arg-Trp-Lys]-D-Pro-D-Leu-NH$_2$ | SEQ ID NO: 174 |
| TCMCA34 66 | Ac-Nle-c[Asp-His-D-Phe-Arg-Trp-Lys]-D-Pro-D-Leu-NH$_2$ | SEQ ID NO: 175 |
| TCMCA34 67 | Ac-Nle-c[D-Asp-Pro-D-Phe-Arg-Trp-D-Lys]-D-Pro-D-Leu-NH$_2$ | SEQ ID NO: 176 |
| TCMCA34 68 | Ac-Nle-c[Asp-His-D-Phe-Arg-Trp-Lys]-D-Pro-D-Leu-NH$_2$ | SEQ ID NO: 177 |
| TCMCA34 69 | Ac-Nle-c[Asp-Pro-D-Phe-Arg-Trp-Lys]-D-Leu-D-Pro-NH$_2$ | SEQ ID NO: 178 |
| TCMCA34 70 | Ac-Nle-c[Asp-His-D-Phe-Arg-Trp-Lys]-D-Leu-D-Pro-NH$_2$ | SEQ ID NO: 179 |
| TCMCA34 71 | Ac-Nle-c[D-Asp-Pro-D-Phe-Arg-Trp-D-Lys]-D-Leu-D-Pro-NH$_2$ | SEQ ID NO: 180 |
| TCMCA34 72 | Ac-Nle-c[D-Asp-His-D-Phe-Arg-Trp-D-Lys]-D-Leu-D-Pro-NH$_2$ | SEQ ID NO: 181 |
| TCMCA34 73 | Ac-Nle-c[Asp-Pro-D-Phe-Arg-Trp-Lys]-β-Pro-β-Leu-NH$_2$ | SEQ ID NO: 182 |
| TCMCA34 74 | Ac-Nle-c[Asp-His-D-Phe-Arg-Trp-Lys]-β-Pro-β-Leu-NH$_2$ | SEQ ID NO: 183 |
| TCMCA34 75 | Ac-Nle-c[D-Asp-Pro-D-Phe-Arg-Trp-D-Lys]-β-Pro-β-Leu-NH$_2$ | SEQ ID NO: 184 |
| TCMCA34 76 | Ac-Nle-c[D-Asp-His-D-Nal(2')-Arg-Trp-D-Lys]-β-Pro-β-Leu-NH$_2$ | SEQ ID NO: 185 |
| TCMCA34 77 | Ac-Nle-c[Asp-Pro-D-Phe-Arg-Trp-Lys]-β-Leu-β-Pro-NH$_2$ | SEQ ID NO: 186 |
| TCMCA34 78 | Ac-Nle-c[Asp-His-D-Phe-Arg-Trp-Lys]-β-Leu-β-Pro-NH$_2$ | SEQ ID NO: 187 |
| TCMCA34 79 | Ac-Nle-c[D-Asp-Pro-D-Phe-Arg-Trp-D-Lys]-β-Leu-β-Pro-NH$_2$ | SEQ ID NO: 188 |
| TCMCA34 80 | Ac-Nle-c[D-Asp-His-D-Phe-Arg-Trp-D-Lys]-β-Leu-β-Pro-NH$_2$ | SEQ ID NO: 189 |
| TCMCA34 81 | Ac-Nle-c[Asp-Pro-D-Phe-Arg-Trp-Lys]-β-Val-β-Leu-NH$_2$ | SEQ ID NO: 190 |
| TCMCA34 82 | Ac-Nle-c[Asp-His-D-Phe-Arg-Trp-Lys]-β-Val-β-Leu-NH$_2$ | SEQ ID NO: 191 |
| TCMCA34 83 | Ac-Nle-c[D-Asp-Pro-D-Phe-Arg-Trp-D-Lys]-β-Val-β-Leu-NH$_2$ | SEQ ID NO: 192 |
| TCMCA34 84 | Ac-Nle-c[D-Asp-His-D-Phe-Arg-Trp-D-Lys]-β-Val-β-Leu-NH$_2$ | SEQ ID NO: 193 |
| TCMCA34 85 | Ac-Nle-c[Asp-Pro-D-Phe-Arg-Trp-Lys]-(3-methyl)-β-Val-β-Leu-NH$_2$ | SEQ ID NO: 194 |
| TCMCA34 86 | Ac-Nle-c[Asp-His-D-Phe-Arg-Trp-Lys]-(3-methyl)-β-Val-β-Leu-NH$_2$ | SEQ ID NO: 195 |
| TCMCA34 87 | Ac-Nle-c[D-Asp-His-D-Phe-Arg-Trp-D-Lys]-(3-methyl)-β-Val-β-Leu-NH$_2$ | SEQ ID NO: 196 |
| TCMCA34 88 | Ac-Nle-c[D-Asp-His-D-Phe-Arg-Trp-D-Lys]-(3-methyl)-β-Val-β-Leu-NH$_2$ | SEQ ID NO: 197 |

Example 14

Lipopolysaccharide Cachexia Assay

In the experiments described herein, a series of melanocortin receptor antagonist peptides were examined in a bacterial endotoxin inducing cachexia assay. For this assay, a rat is challenged with a single peripheral injection of lipopolysaccharide (LPS). LPS is a heat-stable lipo-polysaccharide, the major component of the outer membrane (capsule) of gram negative bacteria. In non-capsulated strains, it appears as a cell surface protein. LPS produces a strong immune response, including secretion of the proinflammatory cytokines Tumor Necrosis Factor α (TNFα) and interleukin-1 (IL-1). Proinflammatory cytokines are known factors that induce cachexia.

Rats are maintained on a 12-hour light/dark cycle. Animals are handled daily for a minimum of 5 consecutive days to acclimate them to the handling required for the experiment. This is critical for feeding experiments, because stressed rats do not eat. On the day of the experiment, individually housed animals receive intraperitoneal (IP) injections of LPS dissolved in 0.5% low-endotoxin BSA, 0.9% saline or 0.5% BSA in 0.9% saline alone, and returned in their home cage. Melanocortin receptor antagonist peptides were administered (IP or by gavage, depending on the type of study) one hour after the LPS injection. The extent of cachexia is measured by the reduction in food intake, measured every two hours. The cachexia typically lasts only a single day. However, rats lose up to 5% of their body weight during a 12-hour light cycle, making up this loss plus food needed for normal growth during the 12-hour dark cycle. Thus, failure to eat appropriately during a single dark cycle is determinable from the animal's weight and any changes thereof.

Example 15

Summary of Metabolically Stabilized Melanocortin Antagonist

The number of new therapeutic agents has declined steadily over the past 30 years, despite the increasing use of combinatorial chemistry and high throughput screening by pharmaceutical company. Horrobin, *J. Roy. Soc. Med.* 93: 341-345 (2000); Scannell et al., *Nature Rev. Drug Discov.* 11: 191-200 (2012). These techniques can generate literally thousands of compounds with enhanced receptor affinity. However, major reasons for drug candidate failure are not addressed by merely focusing an enhanced receptor affinity. Huggins et al., *J. Med. Chem.* 55: 1424-1444 (2012).

Small molecules (often peptide mimetics) were supposed to correct the pharmacokinetic defects inherent in therapeutic peptides. Small molecules are typically produced by combinatorial chemistry, combined with high throughput assay screening of target receptor binding. Increasingly, however, merely using enhanced binding affinity as a metric of success in a drug development strategy does not result in enhanced specificity or reduced toxicity. Horrobin, *J. Roy. Soc. Med.* 93: 341-345 (2000). The enhanced specificity and reduced toxicity are characteristics of biological peptides. Cirillo et al., *Curr. Med. Chem.* 18: 2854-2866 (2011); Sun, *Modern Chem. Applications* 1:1-2 (2013). However, peptides used as pharmaceuticals can lack gastrointestinal (GI) transport and organ uptake to reach the target receptor. Herrera-Ruiz and Knipp, *J. Pharm. Sci.* 92: 691-714 (2003); Huggins et al., *J. Med. Chem.* 55: 1424-1444 (2012).

Over the past 30 years, there have been examples of peptides, both synthetic and natural, with blood brain barrier penetrating-ability due to unknown mechanisms. Rodriguez et al., *Ann. NY Acad. Sci.* 689: 537-539 (1993); Sefler et al., *J. Med. Chem.* 38: 249-257 (1995); Sutton et al., *Peptides* 29: 104-111 (2008). It was hypothesized that there might be a common factor or mechanism mediating this transport, and that it could be possible to pre-hoc produce epithelial barrier penetrating peptides: e.g., peptides with oral and blood brain barrier penetrating ability.

Lipinski's "Rule of 5" is a series of metrics defining physical characteristics of molecules with GI tract or blood brain barrier paracellular (between cell) transport (e.g., molecular weights of no greater than 500 g/mol). Lipinski et al., *Adv. Drug Deliv. Rev.* 46: 3-26 (2001). These "rules" suggest that peptides (all with molecular weights greater than 1000 Da) were moving through epithelial barriers by a different, probably transcellular, mechanism. Movement by an oligopeptide transport system is a probable explanation.

Small (oligo) peptide transport systems have been shown to be present on many epithelial barriers, including the GI tract and the blood brain barrier. Herrera-Ruiz et al., *AAPS Pharm Sci* 3: E9 (2001); Smith et al., *Adv. Drug Deliv. Rev.* 56: 1765-1791 (2004). There have been successful attempts to use these transporters to carry poorly absorbed therapeutic agents, including peptides, across the GI tract. Yang et al., *Pharm. Res.* 16: 1331-1343 (1999); Kikuchi et al., *J. Pharm. Sci.* 98: 1775-1787 (2009). However, these drugs were of rather low molecular weight (~500 Da). A major benefit in using peptide (active) transporters to carry therapeutic agents across epithelial barriers (i.e., the intestine for oral activity) is that there is a good degree of trans-species similarity, compared to paracellular (passive) transport. Cao et al., *Pharm. Res.* 23: 1675-1686 (2006). Peptide transporters are the mechanism through which many of the breakdown products of proteins are absorbed and distributed throughout the body. Because this is a fundamental property of living organisms, it is highly conserved.

By testing a series of melanocortin peptides with progressive derivatizations, oral and blood-brain barrier transport activity in peptides of greater than 1000 molecular weight were obtained. These effects were amino acid specific and stereospecific, and were independent of the total sum of charged and lipophilic residues. These effects are in stark variance with Lipinski's Rule of 5. However, these results are consistent with a ligand-receptor interaction mediating the transcellular movement of these peptides.

A series of melanocortin receptor antagonist peptides were examined in a bacterial toxin inducing cachexia assay. In this assay, a rat was challenged with a single peripheral injection of lipopolysaccharide (LPS), a bacterial toxin that rapidly induces acute cachexia. The extent of cachexia was measured as a reduction in food intake, measured every two hours. The cachexia typically lasts only a single day.

Melanocortin antagonists have been shown to be potent anti-cachexia agents, with the ability to reverse cachexia-induced anorexia and restore lean body mass. Marks et al., *Cancer Res.* 61: 1432-1438 (2001); DeBoer, *Curr. Opin. Clin. Nutr. Metab. Care* 10: 457-462 (2007). Bacterial toxin cachexia lends itself to a rapid assay procedure for evaluating the activity of anti-cachexia drugs given by various routes of administration. A critical aspect to melanocortin antagonist anti-cachexia activity is access to the central nervous system (blood-brain barrier transport). Many peptide and small molecule melanocortin antagonists that have excellent anti-cachexia activity when administered intraventricular (IVt) are unable to affect feeding when given peripherally. U.S. Pat. No. 7,342,089.

Previous studies demonstrated the importance of metabolically stable multi-residue C-terminal extensions to suppress the undesirable cardiovascular side effects of melanocortin peptides. Nordheim et al., *Peptides* 27: 438-443 (2006); Greenfield et al., *N. Engl. J. Med.* 360: 44-52 (2009); and U.S. Patent Application Publication No. US 2012/0220525, which is hereby incorporated by reference. One of the molecules produced using this strategy was Ac-Nle-c[Asp-Pro-D-Nal(2')-Arg-Trp-Lys]-D-Thr-D-Pro-Thr-OH (TCMCB01). While showing little cardiovascular activity, it only produced an anti-cachexia effect when given by IVt administration; there was no blood-brain barrier transport. A series of other metabolically stable oligopeptide extensions in the TCMCB01 molecule were examined.

The initial molecule in the synthesis strategy was: Ac-Nle-c[Asp-Pro-D-Nal(2')-Arg-Trp-Lys]-D-Pro-D-Val-NH$_2$ (TCMCB02) and contains a metabolically stable C-terminal di-peptide extension (D-Pro-D-Val-amide). While this molecule produced anti-cachexia following peripheral administration (i.e., blood-brain barrier transport activity), it had no oral activity. Therefore, the role of other regions of the molecule, i.e. away from the C-terminal di-peptide, were examined for mediating epithelial transport.

For example, the importance of the Pro substitution for His within the cyclized pharmacophore of melanocortin antagonists has been queried. Sutton et al., *Peptides* 29: 104-111 (2008). The TCMCB02 candidate was compared to its His-substituted derivative: Ac-Nle-c[Asp-His-D-Nal(2')-Arg-Trp-Lys]-D-Pro-D-Val-amide (TCMCB03). This molecule had superior anti-cachexia activity following ICV administration, indicating that it was a bettor antagonist at the central melanocortin system. However, TCMCB03 did not possess as good peripheral (intraperitoneal/IP administration) anti-cachexia activity; it had less blood-brain barrier transport activity. This demonstrated that the structure of the peptide being transported (the "load") by the C-terminal di-peptide is as important as the "vehicle." A potential explanation for this effect is that substituting Pro for His decreases intramolecular free rotation, since Pro is an imidic acid: its α-carbon has a secondary amino group forming a peptide bond. These data are consistent with suggestions that a reduction in free rotation enhances the trans-epithelial movement of peptides. Vabeno et al., *Bioorg. Med. Chem.*

13: 1977-1988 (2005); Hess et al., *J. Med. Chem.* 51: 1026-1034 (2008). Cyclization is another approach that can decrease the degree of free rotation typically inherent in a small peptide, and can enhance active peptide transport. Vabeno et al., *Bioorg. Med. Chem.* 13: 1977-1988 (2005).

The basis for cyclizing melanocortins was that a reverse turn conformation was required for receptor binding. Sawyer et al., *Proc. Nat. Acad. Sci. USA* 79: 1751-1755 (1982); Sawyer et al., *J. Med. Chem.* 25: 1022-1027 (1982). Initially, a D-amino acid substitution in the middle of the melanocortin pharmacophore enhanced biological activity; presumably because a D-residue will reduce the tendency of an L-amino acid sequence to form an α-helix, but stabilize a β-turn. Sawyer et al., *Proc. Nat. Acad. Sci. USA* 77: 5754-5758 (1980). Cyclized melanocortins were the next step; first di-sulfide bridging, then a lactam bridge. It was hypothesized that using D-amino acid residues to form the lactam bridge in cyclic MCs would further stabilize the cyclic structure, producing superior biological activity. The D-Asp$^5$, D-Lys$^{10}$ derivative of TCMCB02; Ac-Nle-c[D-Asp-Pro-D-Nal(2')-Arg-Trp-D-Lys]-D-Pro-D-Val-NH$_2$ (TCMCB04) was synthesized and tested.

Given ICV, this derivative had superior ICV anti-cachectic activity (stimulation of feeding in the LPS-induced cachexia model) compared to TCMCB02. However, the derivatization eliminated blood-brain barrier transport; IP administration of the peptide produced no anti-cachexia activity.

The TCMCB04 data demonstrated the stereospecificity of the mechanism responsible for blood-brain barrier transport; stereospecificity is further evidence against paracellular transport. Finally, when taken with the TCMCB03 data (His$^6$ vs. Pro$^6$), it was apparent that relatively minor alterations in the structure of the molecule being transported produce profound changes in transport properties.

A series of derivatives were designed, seeking to combine the steric properties of L-amino acids with the resistance to enzymatic degradation of D-residues. Amino or imidic acid peptide residues with their α-amino and/or carboxyl groups displaced to the β-carbon maintain their side-chain steric structure, but are stable to enzymatic degradation. Lew et al., *FASEB J.* 15: 1664-1666 (2001); Nachman et al., *Peptides* 30:608-615 (2009).

Derivatives of TCMCB02 were synthesized, replacing the C-terminal di-peptide with its β amino acid equivalents: Ac-Nle-c[Asp-Pro-D-Nal(2')-Arg-Trp-Lys]-β$^3$-Pro-β$^2$-Val-NH$_2$ (TCMCB05) or Ac-Nle-c[Asp-Pro-D-Nal(2')-Arg-Trp-Lys]-β$^3$-Pro-β$^3$-Val-NH$_2$ (TCMCB06). Following ICV administration, both TCMCB05 and TCMCB06 had molar activity equivalent to TCMCB02 in LPS-induced cachexia. However, only TCMCB05 had peripheral anti-cachexia activity following LPS administration and provided evidence for β-residue subtype specific blood-brain barrier transport properties in the di-peptide extension (amino group on β carbon preferred over the carboxyl on the β carbon). The ability to differentiate between β amino acid subtypes is a characteristic of an oligopeptide transport mechanism. Brodin et al., *Pharmacol. Toxicol.* 90: 285-296 (2002). TCMCB05, however, was not orally active as an anti-cachexia agent.

In order to increase transport activity in the peptides, the di-peptide sequence specificity for transport properties was investigated. The sequence of the C-terminal di-peptide in TCMCB02, was reversed, producing the derivative Ac-Nle-c[Asp-Pro-D-Nal(2')-Arg-Trp-Lys]-D-Val-D-Pro-NH$_2$ (TCMCB07). The TCMCB07 peptide had about 10-times more activity following peripheral administration than TCMCB02. In addition, TCMCB02 was orally active as an anti-cachexia agent.

TCMCB07 and TCMCB07A are the same peptide except that TCMCB07 has a C-terminal amide moiety and TCMCB07A does not. Peripheral administration of TCMCB07 or TCMCB07A produces equivalent stimulation of feeding in LPS-induced cachexia. Thus, the C-terminal amide moiety has no effect on transport, but may stabilize the peptide from degradation.

Reversing the C-terminal di-peptide sequence (e.g., Pro-Val to Val-Pro) improved transport in the D-residue di-peptide derivatives. Accordingly, β-residue extensions with a reversed sequence (i.e., β-Pro-β-Val changed to β-Val-β-Pro) were investigated. The reversed di-peptide sequence of TCMCB05, i.e., Ac-Nle-c[Asp-Pro-D-Nal(2')-Arg-Trp-Lys]-β$^2$-Val-β$^3$-Pro-NH$_2$ (TCMCB08); had good blood-brain barrier transport, but not as much oral activity as TCMCB07. The reversed sequence of TCMCB06, Ac-Nle-c[Asp-Pro-D-Nal(2')-Arg-Trp-Lys]-β$^3$-Val-β$^3$-Pro-NH$_2$ (TCMCB09), was inactive peripherally.

The rapid appearance in blood of orally administered proline-rich peptides was some of the first evidence for active transport of peptides through the GI tract, and an Xaa-Pro dipeptide is a substrate for the PEPY1. Given these data, the C-terminal di-Pro derivative of TCMCB02 was synthesized and tested: Ac-Nle-c[Asp-Pro-D-Nal(2')-Arg-Trp-Lys]-β$^3$-Pro-β$^3$-Pro-NH$_2$ (TCMCB10). While maintaining direct inhibitory effects (ICV administration in LPS cachexia) on the central melanocortin system, TCMCB10 showed no peripheral activity/a failure to cross the blood-brain barrier.

TABLE 5

Summary of Metabolically Stabilized Melanocortin Antagonist

| | | | |
|---|---|---|---|
| TCMCB01 | Ac-Nle-c[Asp-Pro-D-Nal(2')-Arg-Trp-Lys]-D-Thr-D-Pro-D-Thr-OH | Antag. | SEQ ID NO: 15 |
| TCMCB02 | Ac-Nle-c[Asp-Pro-D-Nal(2')-Arg-Trp-Lys]-D-Pro-D-Val-NH$_2$ | Antag. | SEQ ID NO: 16 |
| TCMCB03 | Ac-Nle-c[Asp-His-D-Nal(2')-Arg-Trp-Lys]-D-Pro-D-Val-NH$_2$ | Antag. | SEQ ID NO: 17 |
| TCMCB04 | Ac-Nle-c[D-Asp-Pro-D-Nal(2')-Arg-Trp-D-Lys]-D-Pro-D-Val-NH$_2$ | Antag. | SEQ ID NO: 18 |
| TCMCB05 | Ac-Nle-c[Asp-Pro-D-Nal(2')-Arg-Trp-Lys]-β$^3$-Pro-β$^2$-Val-NH$_2$ | Antag. | SEQ ID NO: 19 |
| TCMCB06 | Ac-Nle-c[Asp-Pro-D-Nal(2')-Arg-Trp-Lys]-β$^3$-Pro-β$^3$-Val-NH$_2$ | Antag. | SEQ ID NO: 20 |
| TCMCB07 | Ac-Nle-c[Asp-Pro-D-Nal(2')-Arg-Trp-Lys]-D-Val-D-Pro-NH$_2$ | Antag. | SEQ ID NO: 21 |
| TCMCB07A | Ac-Nle-c[Asp-Pro-D-Nal(2')-Arg-Trp-Lys]-D-Val-D-Pro-OH | Antag. | SEQ ID NO: 198 |
| TCMCB08 | Ac-Nle-c[Asp-Pro-D-Nal(2')-Arg-Trp-Lys]-β$^2$-Val-β$^3$-Pro-NH$_2$ | Antag. | SEQ ID NO: 199 |
| TCMCB09 | Ac-Nle-c[Asp-Pro-D-Nal(2')-Arg-Trp-Lys]-β$^3$-Val-β$^3$-Pro-NH$_2$ | Antag. | SEQ ID NO: 200 |

TABLE 5-continued

Summary of Metabolically Stabilized
Melanocortin Antagonist

| | | | |
|---|---|---|---|
| TCMCB10 | Ac-Nle-c[Asp-Pro-D-Nal(2')-Arg-Trp-Lys]-β³-Pro-β³-Pro-NH₂ | Antag. | SEQ ID NO: 201 |

TABLE 6

Summary of Activities of Metabolically
Stabilized Melanocortin Antagonist

| Cmpd | Melanocortin Antagonist | Oral Activity | Periph. Activity | Anti-cachectic Activity |
|---|---|---|---|---|
| TCMCB01 | Ac-Nle-c[Asp-Pro-D-Nal(2')-Arg-Trp-Lys]-D-Thr-D-Pro-D-Thr-OH | − | − | + |
| TCMCB02 | Ac-Nle-c[Asp-Pro-D-Nal(2')-Arg-Trp-Lys]-D-Pro-D-Val-NH₂ | − | + | + |
| TCMCB03 | Ac-Nle-c[Asp-His-D-Nal(2')-Arg-Trp-Lys]-D-Pro-D-Val-NH₂ | − | − | ++ |
| TCMCB04 | Ac-Nle-c[D-Asp-Pro-D-Nal(2')-Arg-Trp-D-Lys]-D-Pro-D-Val-NH₂ | − | − | ++ |
| TCMCB05 | Ac-Nle-c[Asp-Pro-D-Nal(2')-Arg-Trp-Lys]-β³-Pro-β²-Val-NH₂ | − | + | ++ |
| TCMCB06 | Ac-Nle-c[Asp-Pro-D-Nal(2')-Arg-Trp-Lys]-β³-Pro-β³-Val-NH₂ | − | − | ++ |
| TCMCB07 | Ac-Nle-c[Asp-Pro-D-Nal(2')-Arg-Trp-Lys]-D-Val-D-Pro-NH₂ | + | ++ | +++ |
| TCMCB07A | Ac-Nle-c[Asp-Pro-D-Nal(2')-Arg-Trp-Lys]-D-Val-D-Pro-OH | + | ++ | +++ |
| TCMCB08 | Ac-Nle-c[Asp-Pro-D-Nal(2')-Arg-Trp-Lys]-β²-Val-β³-Pro-NH₂ | −+ | ++ | +++ |
| TCMCB09 | Ac-Nle-c[Asp-Pro-D-Nal(2')-Arg-Trp-Lys]-β³-Val-β³-Pro-NH₂ | − | − | +++ |
| TCMCB10 | Ac-Nle-c[Asp-Pro-D-Nal(2')-Arg-Trp-Lys]-β³-Pro-β³-Pro-NH₂ | − | − | +++ |

Example 16

Evidence for Intestinal and Blood-Brain Barrier Active Transport: Oligopeptide Transporters About 60 years ago, the prevailing view that dietary protein absorption occurred after these molecules were broken down to their constituent amino acids was challenged by the evidence for rapid intestinal absorption of di and tri-peptides. Prockop et al., *Lancet* 2: 527-528 (1962); Brandsch et al., *J. Pharm. Pharmacol.* 60: 543-585 (2008). In subsequent decades, the presence of several peptide transport systems for di- and tri-peptides was well documented. Most of this work has focused on the PEPT1 and PEPT2 transport systems, since PEPT1 appears to be the predominant system mediating intestinal absorption of protein-derived peptides. Brodin et al., *Pharmacol. Toxicol.* 90: 285-296 (2002); Brandsch et al., *J. Pharm. Pharmacol.* 60: 543-585 (2008).

The discovery that peptide mimetic antibiotics undergo intestinal absorption via PEPT1 stimulated work on the use of the PEPT1 transport system to enhance the intestinal absorption of drugs with poor oral bioavailability. Sugawara et al., *J. Pharm. Sci.* 89: 781-789 (2000); Terada et al., *Pflug. Arch. Eur. J. Physiol.* 440: 679-684 (2000); Vabeno et al., *Bioorg. Med. Chem.* 13: 1977-1988 (2005); Brandsch et al., *J. Pharm. Pharmacol.* 60: 543-585 (2008); Kikuchi et al., *J. Pharm. Sci.* 98: 1775-1787 (2009). However, the evidence suggested that only molecular complexes of a relatively small size, on the order of di or tri-peptides, could utilize this system. The subsequent discovery of other oligopeptide transport systems did not produce the intense scrutiny of structural transport requirements to which the PEPT family was subjected. Herrera-Ruiz and Knipp, *J. Pharm. Sci.* 92: 691-714 (2003); Smith et al., *Adv. Drug Deliv. Rev.* 56: 1765-1791 (2004).

The stereospecific, di-peptide sequence specific, and β-residue subtype specific nature of oral activity in the melanocortin analogs are requirements that effectively eliminate physical chemical properties as factors mediating movement through epithelial barriers. These structural requirements, however, point to a trans-cellular small peptide transporter. The transporter is similar, but different, in the blood brain barrier (a PEPT2-containing organ) versus the gastrointestinal tract.

There are parallels between the results described herein and what is known about the intestinal epithelial peptide transport system, PEPT1. The peptides described herein and PEPT1 show stereospecificity, sequence specificity, and β-amino acid subtype specificity. Addison et al., *Clin. Sci. Mol. Med.* 49: 313-322 (1975); Adibi, *Am. J. Physiol.* 272: E723-736 (1997); Brandsch, *Amino Acids* 31: 119-136 (2006). Further, there is much greater activity for a di-peptide sequence where there is a proline at the C-terminus and a aliphatic non-polar residue (e.g., Gly, Val, Leu) at the penultimate position, i.e., Val-Pro would have about 10-times more transport activity than Pro-Val. Brandsch, *Amino Acids* 31: 119-136 (2006). This is consistent with comparisons of melanocortin analogs described herein with D-Pro-Val vs. D-Val-D-Pro C-terminal extensions. However, there are also differences, because many molecule described herein comprise blocked amino and carboxyl termini, as well as a D-amino acid residues in the di-peptide transport sequence. These structural factors are reported to be unfavored for PEPT1 transport. Terada et al., *Pflug. Arch. Eur. J. Physiol.* 440: 679-684 (2000).

Structural requirements are described herein that permit oligopeptide transport for much larger molecular weights than have previously reported (e.g., greater than 1200 Da). These studies with melanocortins could facilitate the development of orally active synthetic peptide analogs of natural peptides with molecular weights in excess of 2000 Da. Minor changes in the transported drug's structure produce major changes in transport properties, even though the di-peptide is largely unchanged.

Example 17

Physicochemical Evidence for TCMCB07 Transport through the Rat Blood Brain Barrier Urethane-anesthetized rats had polyethylene (PE)-tubing cannulas placed in their femoral artery and vein. Each rat was then placed in a small animal stereotaxic apparatus, their head fixed in the lateral plane with ear bars, and their head placed in a 45-50° downward angle by placing their nose below an adjustable tooth bar. This position placed the animal's cistern magna at the highest vertical position of its body. The dural covering of the dorsal cistern magna was exposed.

A stainless steel cannula, with one end attached to PE-tubing, was placed in a stereotaxic tower cannula holder (open end down). The free end of the PE-tubing was attached to a 100 μL gas-tight Hamilton syringe with a 28-gauge needle. The cannula was adjusted to a position that approximated the middle of the exposed cistern magna, and the cannula lowered until it touched the dura mater. A vertical stereotaxic reading was recorded, and the cannula slowly lowered until it pierced the dural membrane. The dura has a degree of flexibility such that the cannula can depress it before it pierces it. After it was pierced, the dural rises to its original position, placing the cannula tip within the cistern magna space. The position of the cannula tip was again noted on the vertical axis of the tower. Typically, the cannula tip was 1.6-1.8 mm below the original dura-touch position. The cannula tip was then adjusted, if needed, to 1.8 mm below the dura, and the cannula sealed to the dura using skin glue. Samples of cisternal cerebrospinal (CSF) fluid were removed through cannula and PE-tubing by slowly drawing on the Hamilton syringe.

For the experimental procedure, baseline samples of blood and CSF were taken ("0" time points), followed by the IV administration of 750 nmol/kg TCMCB07. Samples of CSF (50 μL) and blood (1 mL) were collected at the following time points: 0, 5, 15, 30, and 90 minutes. CSF samples were diluted with acetonitrile-HCL to a concentration of 20% acetonitrile, and chromatographed on a microparticulate C-18 reversed-phase high performance liquid chromatography (HPLC) column with a 20-40% acetonitrile-aqueous HCL gradient over 20 minutes. Blood was collected with heparin from the arterial line, and the plasma was isolated by centrifugation. Both CSF and plasma were stored at −80° C. until analyzed by (HPLC) with spectrofluoremetric monitoring at 230 nm excitation and 237 nm emission (the fluorescence maximum for the Nal residue). The spectrofluorometer effluent was collected every 30 seconds, and samples representing fluorometer peaks potentially positive for the Nal residue were subjected to mass spectrometry molecular mass analysis.

Figure 13:
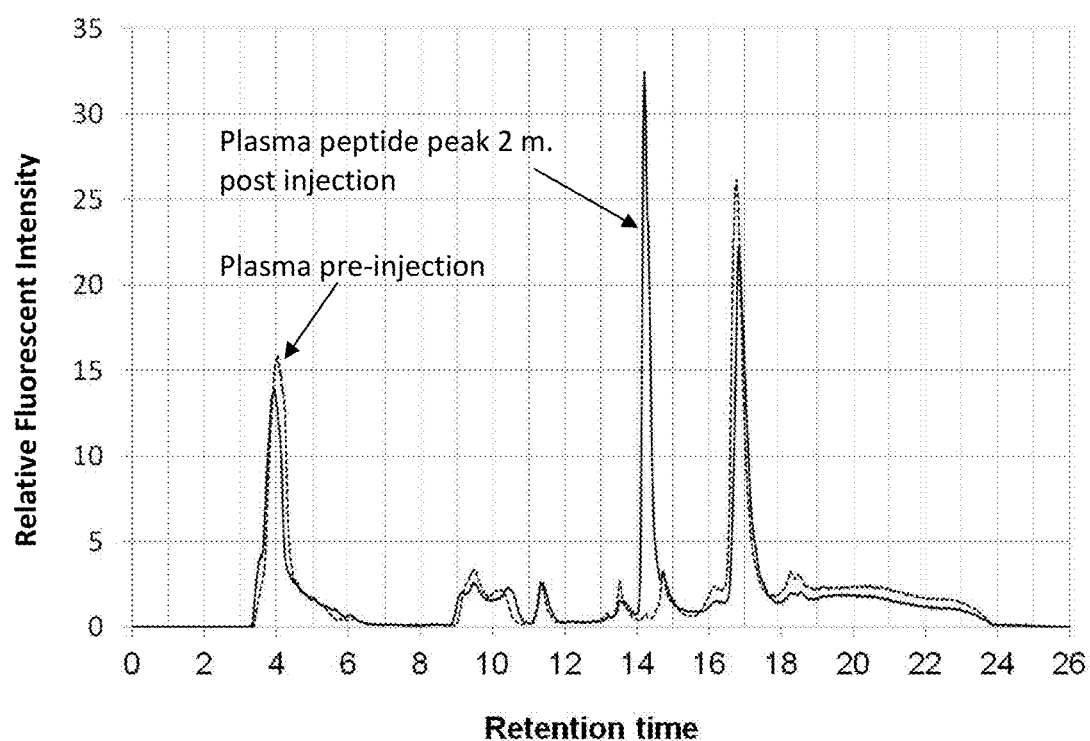
FIG. 13. High performance liquid chromatograms of rat plasma. Time points are pre-intravenous administration and 2 minutes post administration of 750 nmol/kg TCMCB07. A naphthylalanine (Nal residue)-positive fluorescence peak appears at the retention time (14.5 minutes) of TCMCB07. Concentration of TCMCB07 in plasma 2 minutes post-intravenous administration is 7 nmol/mL.
Figure 14:
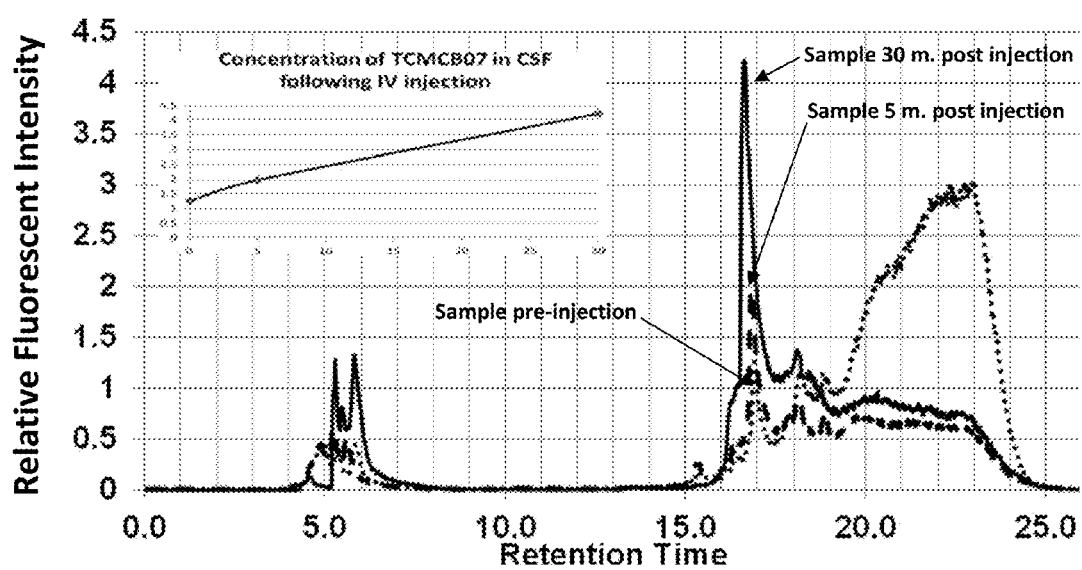
FIG. 14. High performance liquid chromatograms of rat cerebrospinal fluid. Time points: pre administration, 5 and 30 minutes post administration of intravenous TCMCB07 (750 nmol/kg). A naphthylalanine (Nal residue)-positive fluorescence peak appears at a retention time of 12.9 minutes, slightly earlier than TCMCB07 (14.5 minutes). This suggests that the peak is a metabolic product of the drug, a predictable effect for a peptide. The small peak at the 12.9-minute retention time in the pre-administration sample represents a co-eluting component of cerebrospinal fluid. Inserted graph (upper left) shows the increased cerebrospinal fluid concentration (represented as peak height) of the proposed TCMCB07 metabolite over time.

FIGS. 13 and 14 show high performance liquid chromatograms of plasma (FIG. 13) and CSF (FIG. 14), pre- and post-IV administration of TCMCB07 (750 nmol/kg). A naphthylalanine (Nal residue)-positive fluorescence peak is seen in plasma at the exact retention time of TCMCB07 (FIG. 13). The CSF had a Nal-positive fluorescence peak with a slightly earlier retention time than TCMCB07 (FIG. 14). The peak height increases over time after IV drug administration, suggesting it is a TCMCB07 metabolite.

Subsequent analysis of the collected HPLC-spectrofluorometer effluent by mass spectrometry confirmed the presence of TCMCB07 in CSF at the predicted HPLC retention time, even though an obvious Nal-fluorescence positive peak could not be detected. However, mass spectrometry is about 10.000-fold more sensitive than fluorescence.

Figure 15:
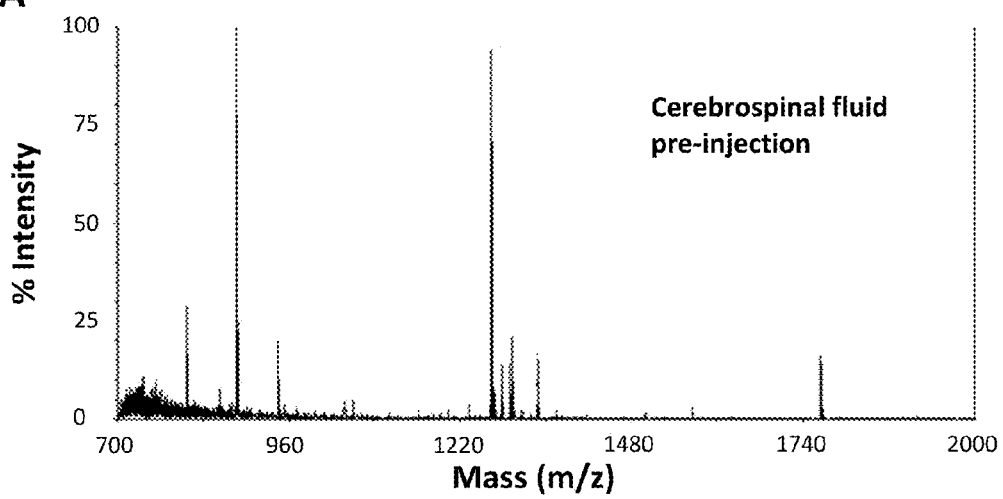
FIG. 15. Mass spectrometry analysis of the collected eluent from the peak with a retention time of 12.9 minutes. The arrows indicate the occurrence of a peptide in the post-injection samples, but not in the pre-injection sample. This peak has an atomic weight of 1,209 Daltons, 21 Daltons less than cyclized TCMCB07, at 1,230 Da.
Figure 15:
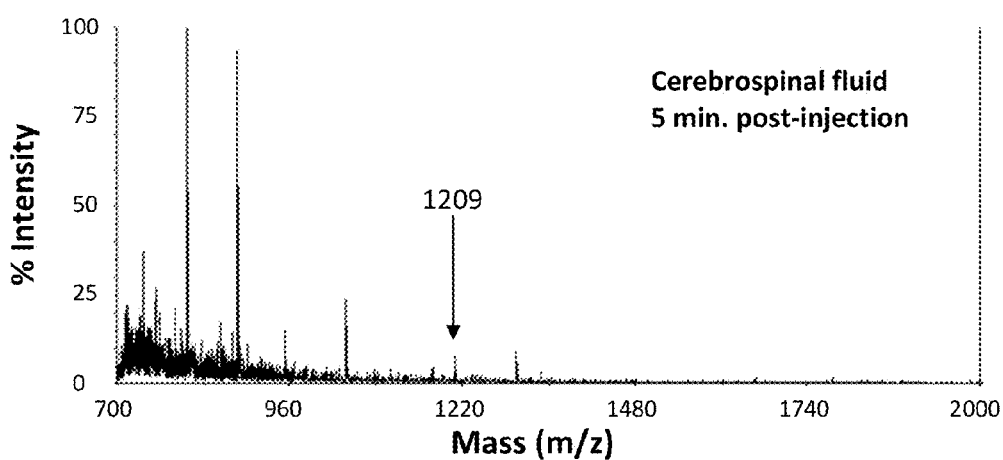
Figure 15:
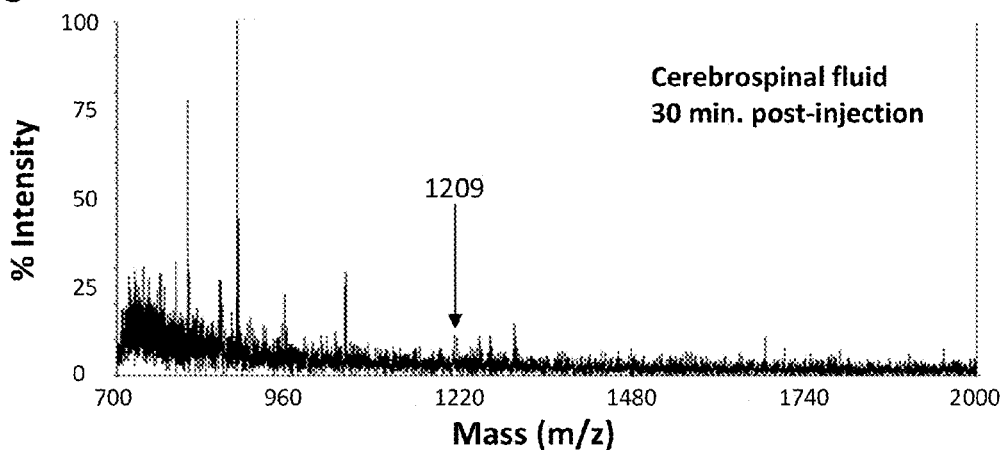

The presumed TCMCB07 metabolite at 12.9 minutes retention time showed a molecular mass of 1209.0 Daltons, 22 Daltons less than TCMCB07. This peptide was only present in CSF after IV administration of TCMCB07; i.e., not present in "0" time CSF samples (FIG. 15). This suggests that the Nal-positive peak at 12.9 minutes retention time is a TCMCB07 breakdown product.

These results provide direct physical evidence of TCMCB07 transport through the blood-brain-barrier that is consistent with the biological evidence of TCMCB07 therapeutic effects observed in cachexia, as described herein.

What is claimed is:

1. A non-naturally occurring melanocortin analog comprising a metabolically stable C-terminal extension that minimizes or reduces side effects and that facilitates traversal of epithelium membranes, blood-brain barrier membranes, or both membranes, comprising:

the sequence according to Formula I: $X^1X^2X^3R^1R^2R^3R^4R^5R^6R^7Y^1Y^2Y^3$, wherein:

the melanocortin analog residues comprise:

R1 is absent or is selected from the group consisting of cysteine, norleucine, acetylated norleucine, acetylated cysteine, methylated D-phenylalanine, succinic acid, o-phthalic acid, tyrosine, aspartic acid, glutaric acid, CO-cis-CH=CH—CO, an n-pentanoyl group, and an n-hexanoyl group;

R2 is absent or is selected from the group consisting of proline, aspartic acid, glutamic acid, glycine, cysteine, norleucine, arginine, succinic acid, glutaric acid, CO-cis-CH=CH—CO, an n-pentanoyl group, and an n-hexanoyl group;

R3 is selected from the group consisting of histidine, histidine methylated at positions 1 or 3, D-proline, L-proline and succinic acid;

R4 is selected from the group consisting of histidine, D-phenylalanine, L-phenylalanine, D-Nal(2'), pCl-D-Phe, and (o-Phe)Phe;

R5 is selected from the group consisting of arginine, homoarginine, ornithine, alanine, proline, Pip, Nip, Tic, Phg, Sar, and Azt;

R6 is selected from D-tryptophan, L-tryptophan, D-Nal (2'), L-Nal(2'), Tic, and Bip;

R7 is absent or is selected from the group consisting of glycine, glutamic acid, cysteine, lysine, and 2,3-diamino-propionic acid;

wherein if R2 is an n-pentanoyl group or an n-hexanoyl group, then $R^1$, $X^1$, $X^2$ and $X^3$ are absent;

$X^1$ is selected from the group consisting of D-cysteine, L-cysteine, D-threonine, D-proline, L-proline, β-homo proline, D-alanine, L-alanine, β-alanine, D-valine, L-valine, β-valine, 3-methyl-β-valine, D-leucine, L-leucine, β-leucine, D-isoleucine, L-isoleucine, β-isoleucine, and a piperazin-2-one ring;

$X^2$ is absent or is selected from the group consisting of D-threonine, D-proline, L-proline, β-homo proline, D-alanine, L-alanine, β-alanine, D-valine, L-valine, β-valine, 3-methyl-β-valine, D-leucine, L-leucine, β-leucine, D-isoleucine, L-isoleucine, β-isoleucine, and a piperazin-2-one ring; and $X^3$ is absent or is selected from the group consisting of D-cysteine, L-cysteine, D-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, and a piperazin-2-one ring;

$Y^1$ is selected from the group consisting of D-alanine, L-alanine, D-valine, L-valine, D-leucine, L-leucine, D-isoleucine, an L-isoleucine;

$Y^2$ is selected from the group consisting of D-proline and L-proline; and $Y^3$ is absent;

the melanocortin analog is cyclized through a moiety selected from the group consisting of:

a disulfide bond between $R^1$ or $R^2$ and $R^7$ or $X^1$ when $R^1$ or $R^2$ is cysteine and $R^7$ or $X^1$ is cysteine;

a lactam bridge between $R^1$ and $R^7$ when $R^1$ is norleucine and $R^7$ is glutamic acid;

a side-chain lactam bridge between $R^2$ and $R^7$ when $R^2$ is glutamic acid or aspartic acid and $R^7$ is lysine;

a lactam closure between $R^1$ and $R^7$ when $R^1$ is succinic acid or o-phthalic acid and $R^7$ is lysine; and a lactam closure between $R^2$ and $R^7$ when $R^2$ is succinic acid and $R^7$ is 2,3-diamino-propionic acid;

the N-terminus is modified by acylation; and the C-terminus is modified by amidation.

2. A non-naturally occurring melanocortin analog comprising any one of the sequences of SEQ ID NOs: 21, 30, 31, 32, 33, 66, 67, 68, 69, 90, 91, 92, 93, 118, 119, 120, 121, 154, 155, 156, 157, 178, 179, 180 or 181.

3. The non-naturally occurring melanocortin analog of claim 1, wherein the melanocortin analog is effective in modulating one or more of cachexia, lethargy, appetite, sleep, arousal, libido, locomotion, cardiovascular anomalies, vasodilatation, hypertension, hypotension, sodium regulation, pain, pain perception, increasing endogenous opioid activity, or decreasing opioid tolerance.

4. A pharmaceutical composition comprising the non-naturally occurring melanocortin analog of claim 1.

5. The pharmaceutical composition of claim 4, further comprising a pharmaceutical salt.

6. The pharmaceutical composition of claim 4, wherein the side effects are reduced compared to a natural melanocortin.

7. A method of treating a disorder in a subject in need thereof comprising administering a non-naturally occurring melanocortin analog of claim 1.

8. The method of claim 7, wherein the administration route is intraperitoneal, intravenous, parenteral, subcutaneous, intramuscular, intracerebroventricular, or orally.

9. The method of claim 8, wherein the non-naturally occurring melanocortin analog crosses the blood-brain-barrier.

10. The method of claim 7, wherein the side effects are reduced compared to a natural melanocortin.

11. A kit for treating cachexia in a subject in need thereof, comprising individual containers containing the pharmaceutical composition of claim 4, a device for administering the pharmaceutical composition, a reagent for diluting the pharmaceutical composition, and instructions for use.

12. The non-naturally occurring melanocortin analog of claim 1, comprising the sequence of SEQ ID NO: 21.

13. A pharmaceutical composition comprising the non-naturally occurring melanocortin analog of claim 1 or a pharmaceutically acceptable salt thereof and, optionally, one or more pharmaceutically acceptable carriers.

* * * * *